US012741939B2

(12) United States Patent
Crosbie et al.

(10) Patent No.: US 12,741,939 B2
(45) Date of Patent: Sep. 22, 2026

(54) COMPOSITIONS AND METHODS FOR TREATING MUSCULAR DYSTROPHIES

(71) Applicant: The Regents of the University of California, Oakland, CA (US)

(72) Inventors: Rachelle H. Crosbie, Los Angeles, CA (US); Cynthia Shu, Los Angeles, CA (US); Varghese John, Los Angeles, CA (US); Jesus Campagna, Los Angeles, CA (US); Barbara Jagodzinska, Los Angeles, CA (US); Liubov Parfenova, Los Angeles, CA (US); Ekaterina Mokhonova, Los Angeles, CA (US)

(73) Assignee: The Regents of the University of California, Oakland, CA (US)

(*) Notice: Subject to any disclaimer, the term of this patent is extended or adjusted under 35 U.S.C. 154(b) by 473 days.

(21) Appl. No.: 18/025,747

(22) PCT Filed: Sep. 8, 2021

(86) PCT No.: PCT/US2021/049362
§ 371 (c)(1),
(2) Date: Mar. 10, 2023

(87) PCT Pub. No.: WO2022/055926
PCT Pub. Date: Mar. 17, 2022

(65) Prior Publication Data

US 2023/0348394 A1 Nov. 2, 2023

Related U.S. Application Data

(60) Provisional application No. 63/148,823, filed on Feb. 12, 2021, provisional application No. 63/077,329, filed on Sep. 11, 2020.

(51) Int. Cl.
*C07D 215/36* (2006.01)
*C07D 213/89* (2006.01)
*C07D 215/54* (2006.01)
*C07D 401/12* (2006.01)
*C07D 413/12* (2006.01)

(52) U.S. Cl.
CPC ......... *C07D 215/36* (2013.01); *C07D 213/89* (2013.01); *C07D 215/54* (2013.01); *C07D 401/12* (2013.01); *C07D 413/12* (2013.01)

(58) Field of Classification Search
CPC ................ C07D 215/36; C07D 215/54; C07D 213/89; C07D 401/12; C07D 413/12
See application file for complete search history.

(56) References Cited

U.S. PATENT DOCUMENTS

| | | | | |
|---|---|---|---|---|
| 10,662,192 B2* | 5/2020 | Hadida-Ruah | ....... | C07D 209/96 |
| 2018/0362467 A1 | 12/2018 | Bettoun et al. | | |
| 2021/0238162 A1* | 8/2021 | Cadilla | .................... | A61P 9/00 |

FOREIGN PATENT DOCUMENTS

| | | | |
|---|---|---|---|
| RU | 2462458 C2 | 9/2012 |
| WO | WO-94/04535 A1 | 3/1994 |
| WO | WO-2007/008541 A2 | 1/2007 |
| WO | WO-2008/059214 A1 | 5/2008 |
| WO | WO-2009/021750 A2 | 2/2009 |
| WO | WO-2012/098070 A1 | 7/2012 |
| WO | WO-2012/106343 A2 | 8/2012 |
| WO | WO-2014/007620 A2 | 1/2014 |
| WO | WO-2017/103851 A1 | 6/2017 |
| WO | WO-2018/174288 A1 | 9/2018 |
| WO | WO-2019/084499 A1 | 5/2019 |
| WO | WO-2019/236677 A1 | 12/2019 |
| WO | WO-2022/055926 A1 | 3/2022 |
| WO | WO-2024/229205 A1 | 11/2024 |

OTHER PUBLICATIONS

Ervasti, Biochimica et Biophysica Acta 1772, (2007), 108-117. (Year: 2007).*
Bhatia, Pharmacologyonline 1: 272-299 (2011). (Year: 2011).*
CAS Registry No. 1100333-55-8. Entered STN: Feb. 3, 2009.
CAS Registry No. 1100337-17-4. Entered STN: Feb. 3, 2009.
CAS Registry No. 1105188-53-1. Entered STN: Feb. 13, 2009.
CAS Registry No. 1105189-97-6. Entered STN: Feb. 13, 2009.
Database PubChem Substance, Accession No. RN 1100333-54-7, "2-[[2-{4-Fluorophenyl)-2-oxoethyl]thio]-6 ,7-dimethyl-3-quinolinecarbonitrile" Entered STN: Feb. 3, 2009.
Database PubChem Substance, Accession No. RN 943076-33-3, "2-[ [2-(4-methoxyphenyl)-2-oxoethyl] thio] 6,7-dimethyl-3-quinolinecarbonitrile" Entered STN: Jul. 22, 2007.
Partial Supplementary European Search Report for EP Application No. 21867476.0 dated Sep. 17, 2024.
PubChem SID 105219246, 11 (2-[2-(4-Methoxyphenyl)-2-oxoethyl]sulfan yl6,7-dimethylquinoline-3-carbonitrile) created Feb. 22, 2011.
PubChem CID 855355, "6,8-Dimethyl-2-phenacylsulfanylquinoline-3-carbonitrile : C20H16N20S : CID 855355—PubChem" created Jul. 9, 2005.
CAS Registry No. 1100314-65-5 Entered STN: Feb. 3, 2009.
CAS Registry No. 1100314-67-7 Entered STN: Feb. 3, 2009.
CAS Registry No. 1100315-65-8 Entered STN: Feb. 3, 2009.
CAS Registry No. 1100315-66-9 Entered STN: Feb. 3, 2009.
CAS Registry No. 1100315-67-0 Entered STN: Feb. 3, 2009.
CAS Registry No. 1100315-69-2 Entered STN: Feb. 3, 2009.
CAS Registry No. 1100319-20-7 Entered STN: Feb. 3, 2009.
CAS Registry No. 1100332-85-1 Entered STN: Feb. 3, 2009.
CAS Registry No. 1100332-86-2 Entered STN: Feb. 3, 2009.
CAS Registry No. 1100333-54-7 Entered STN: Feb. 3, 2009.
CAS Registry No. 1105189-92-1 Entered STN: Feb. 13, 2009.
CAS Registry No. 333323-40-3 Entered STN: Apr. 27, 2001.
CAS Registry No. 333323-41-4 Entered STN: Apr. 27, 2001.
CAS Registry No. 333329-68-3 Entered STN: Apr. 27, 2001.
CAS Registry No. 333329-94-5 Entered STN: Apr. 27, 2001.
CAS Registry No. 333329-95-6 Entered STN: Apr. 27, 2001.
CAS Registry No. 333329-96-7 Entered STN: Apr. 27, 2001.
CAS Registry No. 335219-45-9 Entered STN: May 11, 2001.
CAS Registry No. 335219-46-0 Entered STN: May 11, 2001.

(Continued)

*Primary Examiner* — D Margaret M Seaman
(74) *Attorney, Agent, or Firm* — Foley Hoag LLP; David P. Halstead; David S. Surry

(57) ABSTRACT

The present disclosure relates to compounds that increase sarcospan expression. The disclosure further relates to methods of treating a disease related to diminution or dysfunction of a dystrophin-related complex in a subject in need thereof.

10 Claims, 18 Drawing Sheets

(56) References Cited

OTHER PUBLICATIONS

CAS Registry No. 335219-47-1 Entered STN: May 11, 2001.
CAS Registry No. 335219-81-3 Entered STN: May 11, 2001.
CAS Registry No. 335220-17-2 Entered STN: May 11, 2001.
CAS Registry No. 335220-19-4 Entered STN: May 11, 2001.
CAS Registry No. 338432-81-8 Entered STN: May 25, 2001.
CAS Registry No. 338432-83-0 Entered STN: May 25, 2001.
CAS Registry No. 351361-09-6 Entered STN: Aug. 14, 2001.
CAS Registry No. 351361-12-1 Entered STN: Aug. 14, 2001.
CAS Registry No. 443742-86-7 Entered STN: Aug. 13, 2002.
CAS Registry No. 443743-28-0 Entered STN: Aug. 13, 2002.
CAS Registry No. 443744-97-6 Entered STN: Aug. 13, 2002.
CAS Registry No. 459434-47-0 Entered STN: Oct. 7, 2002.
CAS Registry No. 482653-38-3 Entered STN: Jan. 29, 2003.
CAS Registry No. 482653-39-4 Entered STN: Jan. 29, 2003.
CAS Registry No. 485335-84-0 Entered STN: Feb. 4, 2003.
CAS Registry No. 485335-85-1 Entered STN: Feb. 4, 2003.
CAS Registry No. 552816-61-2 Entered STN: Jul. 23, 2003.
CAS Registry No. 552816-80-5 Entered STN: Jul. 23, 2003.
CAS Registry No. 552816-82-7 Entered STN: Jul. 23, 2003.
CAS Registry No. 571959-65-4 Entered STN: Aug. 24, 2003.
CAS Registry No. 602263-55-8 Entered STN: Oct. 10, 2003.
CAS Registry No. 602264-15-3 Entered STN: Oct. 10, 2003.
CAS Registry No. 602264-16-4 Entered STN: Oct. 10, 2003.
CAS Registry No. 602264-17-5 Entered STN: Oct. 10, 2003.
CAS Registry No. 602264-19-7 Entered STN: Oct. 10, 2003.
CAS Registry No. 602264-97-1 Entered STN: Oct. 10, 2003.
CAS Registry No. 602265-05-4 Entered STN: Oct. 10, 2003.
CAS Registry No. 602265-06-5 Entered STN: Oct. 10, 2003.
CAS Registry No. 602265-07-6 Entered STN: Oct. 10, 2003.
CAS Registry No. 602265-08-7 Entered STN: Oct. 10, 2003.
CAS Registry No. 602265-09-8 Entered STN: Oct. 10, 2003.
CAS Registry No. 602294-26-8 Entered STN: Oct. 10, 2003.
CAS Registry No. 602294-28-0 Entered STN: Oct. 10, 2003.
CAS Registry No. 602294-30-4 Entered STN: Oct. 10, 2003.
CAS Registry No. 602295-54-5 Entered STN: Oct. 10, 2003.
CAS Registry No. 602295-57-8 Entered STN: Oct. 10, 2003.
CAS Registry No. 602295-58-9 Entered STN: Oct. 10, 2003.
CAS Registry No. 602295-59-0 Entered STN: Oct. 10, 2003.
CAS Registry No. 602295-60-3 Entered STN: Oct. 10, 2003.
CAS Registry No. 602295-61-4 Entered STN: Oct. 10, 2003.
CAS Registry No. 602324-04-9 Entered STN: Oct. 10, 2003.
CAS Registry No. 602324-05-0 Entered STN: Oct. 10, 2003.
CAS Registry No. 602324-57-2 Entered STN: Oct. 10, 2003.
CAS Registry No. 602324-58-3 Entered STN: Oct. 10, 2003.
CAS Registry No. 602324-59-4 Entered STN: Oct. 10, 2003.
CAS Registry No. 602325-33-7 Entered STN: Oct. 10, 2003.
CAS Registry No. 602325-34-8 Entered STN: Oct. 10, 2003.
CAS Registry No. 602325-35-9 Entered STN: Oct. 10, 2003.
CAS Registry No. 602325-36-0 Entered STN: Oct. 10, 2003.
CAS Registry No. 602325-37-1 Entered STN: Oct. 10, 2003.
CAS Registry No. 602325-38-2 Entered STN: Oct. 10, 2003.
CAS Registry No. 603075-22-5 Entered STN: Oct. 13, 2003.
CAS Registry No. 603079-22-7 Entered STN: Oct. 13, 2003.
CAS Registry No. 603079-37-4 Entered STN: Oct. 13, 2003.
CAS Registry No. 603079-62-5 Entered STN: Oct. 13, 2003.
CAS Registry No. 943074-76-8 Entered STN: Jul. 22, 2007.
CAS Registry No. 943075-46-5 Entered STN: Jul. 22, 2007.
CAS Registry No. 943075-54-5 Entered STN: Jul. 22, 2007.
CAS Registry No. 943075-62-5 Entered STN: Jul. 22, 2007.
CAS Registry No. 943076-33-3 Entered STN: Jul. 22, 2007.
CAS Registry No. 943076-65-1 Entered STN: Jul. 22, 2007.
CAS Registry No. 943076-86-6 Entered STN: Jul. 22, 2007.
CAS Registry No. 943077-03-0 Entered STN: Jul. 22, 2007.
CAS Registry No. 943077-14-3 Entered STN: Jul. 22, 2007.
CAS Registry No. 943084-59-1 Entered STN: Jul. 22, 2007.
CAS Registry No. 943084-72-8 Entered STN: Jul. 22, 2007.
CAS Registry No. 943085-28-7 Entered STN: Jul. 22, 2007.
CAS Registry No. 943085-35-6 Entered STN: Jul. 22, 2007.
CAS Registry No. 943085-59-4 Entered STN: Jul. 22, 2007.
CAS Registry No. 943085-83-4 Entered STN: Jul. 22, 2007.
CAS Registry No. 943093-87-6 Entered STN: Jul. 22, 2007.
Commercial Compound CID 56814734, "N-[4-(1,4-diazepane-1-carbonyl)pyridin-2-yl]-2-oxo-2H-chromene-3-carboxamide", Chemical suppliers Reaxys dated Dec. 2, 2020.
International Search Report and Written Opinion for Application No. PCT/US24/27387 dated Jul. 29, 2024.
PubChem CID 167989645, "N-[4-methyl-3-(morpholine-4-carbonyl)phenyl]-2-oxo-1H-quinoline-3-carboxamide", created Apr. 25, 2023.
PubChem CID 2970812, "N-[4-(4 morpholinylcarbonyl)phenyl]-2-oxo-2H-chromene-3-carboxamide", created Jul. 29, 2005.
CAS Registry No. 1794433-37-6; Entered STN: Jul. 5, 2015.
CAS Registry No. 842960-38-7; Entered STN: Mar. 6, 2005.
International Search Report and Written Opinion for International Application No. PCT/US2021/049362 dated Nov. 15, 2021.
Extended European Search Report for EP Application No. 21867476.0 dated Dec. 12, 2024.
PubChem CID 33959909, "7-methoxy-2-methyl-N-[4-(methylcarbamoyl)phenyl]quinoline-3-carboxamide," created May 29, 2009.
PubChem CID 33959914, "6-chloro-2-methyl-N-[4-(methylcarbamoyl)phenyl]quinoline-3-carboxamide," created May 29, 2009.
PubChem CID 33960006, "2,6-dimethyl-N-[4-(methylcarbamoyl)phenyl]quinoline-3-carboxamide," created May 29, 2009.
CAS Registry No. 1287719-35-0 Entered STN: May 1, 2011.
CAS Registry No. 1288334-59-7 Entered STN: May 1, 2011.
CAS Registry No. 1290417-03-6 Entered STN: May 1, 2011.
CAS Registry No. 1294888-83-7 Entered STN: May 1, 2011.
CAS Registry No. 1299645-51-4 Entered STN: May 1, 2011.
CAS Registry No. 1363813-11-9 Entered STN: May 1, 2011.
CAS Registry No. 2183230-98-8 Entered STN: May 1, 2011.
CAS Registry No. 443744-94-3 Entered STN: Aug. 13, 2002.

* cited by examiner 200,000
molecules screened
hSSPN promoter
EGFP
hSSPN-EGFP
C2C12
n=1
1000
hits rescreened
hSSPN promoter
EGFP
hSSPN-EGFP
C2C12
n=3
hSSPN promoter
luciferase
hSSPN-luciferase
C2C12
n=3
63
confirmed hits
21
hits in
Pharmacophore 1
(PC1)
7
hits in
Pharmacophore 2
(PC2)
35
"other" hits SSPN mRNA (R.U.)
0
1
2
3
4
Vehicle
OT-4
OT-6
OT-7
OT-8
OT-9
OT-13
OT-14
OT-15
OT-16
OT-20
OT-23
OT-28
OT-29
OT-40
OT-43
OT-44
OT-49
OT-50
OT-51
OT-52
OT-53
OT-54
OT-55
Other a
SSPM m RNA (R.U.)
3.0
2.0
1.0
0.0
Veh
PC1-19
PC1-33
PC1-36
PC1-39
PC1-41
PC1-42
OT-9
OT-20
OT-40
0.5 μM
1 μM
5.5 μM
15 μM
25 μM
50 μM
b
OT-9 (μM)
Vehicle
2.5
5
10
SSPN
GAPDH
-25kDa
-35kDa
c
PC1-36 (μM)
Vehicle
5
10
SSPN
GAPDH
-25kDa
-35kDa
SSPM protein (R.U.)
Veh
2.5
5
10
OT-9 (μM)
SSPM protein (R.U.)
4
3
2
1
0
Veh
5
10
PC1-36 (μM)

a
-DG (glycan)
-DG (core)
Extracellular matrix
Laminin
DGs
Matriglycan
Sarcolemma
SGs
SSPN
Dystrophin/Utrophin
Cortical actin cytoskeleton
b
C2C12 membrane
Veh
OT-9
α-DG (glycan)
α-DG (core) short exposure
α-DG (core) long exposure
-130 kDa
-130 kDa
-130 kDa
c
α-dystroglycan (glycan)
Protein (R.U.)
2.5
2.0
1.5
1.0
0.5
0.0
*
Veh
OT-9
d
α-dystroglycan (core)
Protein (R.U.)
2.5
2.0
1.5
1.0
0.5
0.0
*
Veh
OT-9
e
mdx membrane
Veh
OT-9
UTRN
-250 kDa
f
Protein (R.U.)
2.5
2.0
1.5
1.0
0.5
0.0
*
Veh
OT-9

FIG. 7

| Plate# | SSMD* | Plate# | SSMD* | Plate# | SSMD* | Plate# | SSMD* | Plate# | SSMD* | Plate# | SSMD* | Plate# | SSMD* |
|---|---|---|---|---|---|---|---|---|---|---|---|---|---|
| 1 | 1.1 | 77 | 2.16 | 153 | 1.12 | 229 | 1.34 | 305 | 1.52 | 381 | 1.71 | 457 | 2.16 |
| 2 | 1 | 78 | 1.2 | 154 | 207 | 230 | 1.31 | 306 | 1.47 | 382 | 2.28 | 458 | 1.6 |
| 3 | 1 | 79 | 1.01 | 155 | 1.34 | 231 | 1 | 307 | 1.81 | 383 | 1.79 | 459 | 1.62 |
| 4 | 1.01 | 80 | 1.33 | 156 | 2 | 232 | 1.09 | 308 | 2.74 | 384 | 2.59 | 460 | 1.98 |
| 5 | 1.85 | 81 | 1.23 | 157 | 2.37 | 233 | 1.7 | 309 | 1.68 | 385 | 2.59 | 461 | 2.5 |
| 6 | 1.04 | 82 | 1.53 | 158 | 2.16 | 234 | 1.37 | 310 | 1.34 | 386 | 2.19 | 462 | 1.75 |
| 7 | 1.68 | 83 | 1.24 | 159 | 2.15 | 235 | 1.97 | 311 | 1.97 | 387 | 1.83 | 463 | 2.37 |
| 8 | 1.21 | 84 | 1.19 | 160 | 1.39 | 236 | 1.24 | 312 | 1.68 | 388 | 2.02 | 464 | 1.98 |
| 9 | 1.54 | 85 | 1.37 | 161 | 1.63 | 237 | 1.35 | 313 | 1.68 | 389 | 2.66 | 465 | 1.93 |
| 10 | 1.28 | 86 | 1.24 | 162 | 1.23 | 238 | 1.07 | 314 | 1.88 | 390 | 2.03 | 466 | 2.69 |
| 11 | 1.11 | 87 | 1.14 | 163 | 1.13 | 239 | 1.08 | 315 | 203 | 391 | 2.15 | 467 | 1.67 |
| 12 | 1 | 88 | 1.1 | 164 | 1.51 | 240 | 1.08 | 316 | 224 | 392 | 2.41 | 468 | 267 |
| 13 | 1.49 | 89 | 1 | 165 | 1.18 | 241 | 1.03 | 317 | 228 | 393 | 3.07 | 469 | 236 |
| 14 | 1 | 90 | 1.15 | 166 | 1.17 | 242 | 1.04 | 318 | 1.73 | 394 | 3.1 | 470 | 236 |
| 15 | 1.17 | 91 | 1.14 | 167 | 2.05 | 243 | 1.1 | 319 | 1.56 | 395 | 222 | 471 | 1.66 |
| 16 | 1.66 | 92 | 1.05 | 168 | 2.55 | 244 | 1 | 320 | 2.68 | 396 | 224 | 472 | 1.34 |
| 17 | 1.22 | 93 | 1.33 | 169 | 1.25 | 245 | 1.1 | 321 | 2.41 | 397 | 3.27 | 473 | 248 |
| 18 | 1 | 94 | 1.67 | 170 | 221 | 246 | 1.55 | 322 | 1.73 | 398 | 1.96 | 474 | 211 |
| 19 | 1.53 | 95 | 1.42 | 171 | 279 | 247 | 1.07 | 323 | 3.3 | 399 | 263 | 475 | 278 |
| 20 | 1 | 96 | 1.05 | 172 | 1.53 | 248 | 1.03 | 324 | 2.42 | 400 | 1.5 | 476 | 3.62 |
| 21 | 1.14 | 97 | 1.49 | 173 | 263 | 249 | 1.8 | 325 | 2.01 | 401 | 2.75 | 477 | 241 |
| 22 | 1.32 | 98 | 1.19 | 174 | 1.85 | 250 | 1.08 | 326 | 1.77 | 402 | 1.31 | 478 | 3.22 |
| 23 | 1.22 | 99 | 1.05 | 175 | 262 | 252 | 1.59 | 327 | 2.42 | 403 | 232 | 479 | 1.05 |
| 24 | 1 | 100 | 1.25 | 176 | 1.82 | 252 | 1.65 | 328 | 228 | 404 | 281 | 480 | 216 |
| 25 | 1.08 | 101 | 1.53 | 177 | 233 | 253 | 1.08 | 329 | 205 | 405 | 247 | 481 | 1 |
| 26 | 1.5 | 102 | 1.12 | 178 | 216 | 254 | 2.05 | 330 | 3.35 | 406 | 224 | 482 | 1.26 |

FIG. 7 (cont.)

| | | | | | | | | | | | | | |
|---|---|---|---|---|---|---|---|---|---|---|---|---|---|
| 27 | 1.17 | 103 | 1.29 | 179 | 1.68 | 255 | 1.56 | 331 | 1.53 | 407 | 283 | 483 | 1.1 |
| 28 | 1 | 104 | 1.72 | 180 | 2.38 | 256 | 1.18 | 332 | 1.48 | 408 | 271 | 484 | 1.25 |
| 29 | 1.36 | 105 | 1.42 | 181 | 1.49 | 257 | 1.54 | 333 | 1.51 | 409 | 1,09 | 485 | 1.67 |
| 30 | 223 | 106 | 1.81 | 182 | 1.77 | 258 | 1.54 | 334 | 1.83 | 410 | 1.03 | 486 | 1.4 |
| 31 | 279 | 107 | 1.42 | 183 | 2.03 | 259 | 1 | 335 | 1.07 | 411 | 1 | 487 | 1.4 |
| 32 | 1.68 | 108 | 1.74 | 184 | 2.56 | 260 | 1.04 | 336 | 238 | 412 | 1.01 | 488 | 1 |
| 33 | 1.01 | 109 | 1.27 | 185 | 2.95 | 261 | 1.04 | 337 | 1.62 | 413 | 1.33 | 489 | 1.36 |
| 34 | 2.37 | 110 | 1.01 | 186 | 1.28 | 262 | 1.14 | 338 | 1.62 | 414 | 1.35 | 490 | 1.27 |
| 35 | 1.65 | 111 | 1.62 | 187 | 1.62 | 263 | 1.26 | 339 | 2.31 | 415 | 1.65 | 491 | 1.07 |
| 36 | 203 | 112 | 1.03 | 188 | 1.11 | 264 | 1.44 | 340 | 1.2 | 416 | 1.98 | 492 | 1.46 |
| 37 | 1.85 | 113 | 1.46 | 189 | 1.02 | 265 | 1.53 | 341 | 1.58 | 417 | 1.66 | 493 | 1.1 |
| 38 | 1.32 | 114 | 1 | 190 | 1.38 | 266 | 1.82 | 342 | 1.77 | 418 | 1.75 | 494 | 1.56 |
| 39 | 1.49 | 115 | 1.4 | 191 | 1.43 | 267 | 1.4 | 343 | 1 | 419 | 1.62 | 495 | 1.26 |
| 40 | 1.49 | 116 | 1.22 | 192 | 1.61 | 268 | 1.47 | 344 | 1.17 | 420 | 1.7 | 496 | 1.54 |
| 41 | 221 | 117 | 1.32 | 193 | 2.07 | 269 | 1.5 | 345 | 1.12 | 421 | 21 | 497 | 1.81 |
| 42 | 221 | 118 | 1.05 | 194 | 1.05 | 270 | 1.86 | 346 | 1.37 | 422 | 209 | 498 | 1.3 |
| 43 | 1.46 | 119 | 1.59 | 195 | 1.31 | 271 | 1.84 | 347 | 1.85 | 423 | 1.77 | 499 | 1.5 |
| 44 | 1.38 | 120 | 1.12 | 196 | 1.03 | 272 | 1.41 | 348 | 1.49 | 424 | 1.6 | 500 | 1.91 |
| 45 | 1 | 121 | 1.86 | 197 | 1.13 | 273 | 1.65 | 349 | 1.73 | 425 | 1.5 | 501 | 1.44 |
| 46 | 1 | 122 | 1.68 | 198 | 1.4 | 274 | 2.36 | 350 | 1.58 | 426 | 1.4 | 502 | 1.66 |
| 47 | 1.02 | 123 | 1 | 199 | 1.21 | 275 | 2.13 | 351 | 1.92 | 427 | 1.45 | 503 | 201 |
| 48 | 1.17 | 124 | 2.24 | 200 | 1.42 | 276 | 2.38 | 352 | 2.32 | 428 | 1.89 | 504 | 1.45 |
| 49 | 1 | 125 | 1.61 | 201 | 1 | 277 | 1.22 | 353 | 211 | 429 | 1.7 | 505 | 1.75 |
| 50 | 1.18 | 126 | 1.27 | 202 | 1.13 | 278 | 1.73 | 354 | 1.77 | 430 | 1.57 | 506 | 1.64 |
| 51 | 1 | 127 | 1.04 | 203 | 1.19 | 279 | 2.36 | 355 | 219 | 431 | 1.56 | 507 | 2.1 |
| 52 | 1.01 | 128 | 1.39 | 204 | 1.44 | 280 | 2.31 | 356 | 270 | 431 | 1.88 | 508 | 1.9 |
| 53 | 1.39 | 129 | 1.98 | 205 | 1.43 | 281 | 225 | 357 | 1.55 | 433 | 1.88 | 509 | 2.13 |

FIG. 7 (cont.)

| | | | | | | | | | | | | | |
|---|---|---|---|---|---|---|---|---|---|---|---|---|---|
| 54 | 1.4 | 130 | 1 | 206 | 1.52 | 282 | 259 | 358 | 1.38 | 434 | 1.82 | 510 | 1.72 |
| 55 | 1.10 | 131 | 1.46 | 207 | 1.03 | 283 | 248 | 359 | 1.49 | 435 | 21 | 511 | 268 |
| 56 | 1.08 | 132 | 1.23 | 208 | 1.2 | 284 | 223 | 360 | 1.49 | 436 | 1.8 | 512 | 1.37 |
| 57 | 1 | 133 | 1.2 | 209 | 1.25 | 285 | 22 | 361 | 1.59 | 437 | 1.53 | 513 | 1.09 |
| 58 | 1.52 | 134 | 1.68 | 210 | 1.01 | 286 | 1.96 | 362 | 1.69 | 438 | 213 | 514 | 1.63 |
| 59 | 1 | 135 | 1.36 | 211 | 1.06 | 287 | 202 | 363 | 1.47 | 439 | 1.48 | 515 | 1.05 |
| 60 | 1.48 | 136 | 24 | 212 | 1.17 | 288 | 248 | 364 | 1.65 | 440 | 211 | 516 | 1 |
| 61 | 3.02 | 137 | 1.01 | 213 | 1.33 | 289 | 28 | 365 | 245 | 441 | 1.43 | 517 | 1.23 |
| 62 | 1.29 | 138 | 1.18 | 214 | 1.63 | 290 | 25 | 366 | 1.95 | 442 | 236 | 518 | 1.22 |
| 63 | 1.24 | 139 | 1.09 | 215 | 1.27 | 291 | 294 | 367 | 1.69 | 443 | 1.86 | 519 | 1.02 |
| 64 | 1.02 | 140 | 1.64 | 216 | 1 | 292 | 241 | 368 | 1.8 | 444 | 3.29 | 520 | 1 |
| 65 | 1.04 | 141 | 1.5 | 217 | 1.81 | 293 | 256 | 369 | 22 | 445 | 1.23 | 521 | 1.33 |
| 66 | 1 | 142 | 1 | 218 | 1.35 | 294 | 231 | 370 | 207 | 446 | 1.19 | 522 | 204 |
| 67 | 1.29 | 143 | 1 | 219 | 1.45 | 295 | 1.35 | 371 | 262 | 447 | 1.59 | 523 | 1.08 |
| 68 | 1.12 | 144 | 1.09 | 220 | 1.72 | 296 | 1.33 | 372 | 24 | 448 | 1.73 | 524 | 216 |
| 69 | 1 | 145 | 1.06 | 221 | 1.97 | 297 | 1.02 | 373 | 277 | 449 | 1.93 | 525 | 1.76 |
| 70 | 1.38 | 146 | 1.63 | 222 | 1.2 | 298 | 1.78 | 374 | 1.78 | 450 | 1.32 | 526 | 1.04 |
| 71 | 208 | 147 | 1.28 | 223 | 1.49 | 299 | 1.19 | 375 | 1.71 | 451 | 1.58 | 527 | 1.88 |
| 72 | 1.87 | 148 | 1.34 | 224 | 1.23 | 300 | 1.77 | 376 | 213 | 452 | 273 | 528 | 1.64 |
| 73 | 1.3 | 149 | 1.84 | 225 | 1.41 | 301 | 1.92 | 377 | 1.49 | 453 | 228 | 529 | 1.74 |
| 74 | 1.11 | 150 | 1.3 | 226 | 1.33 | 302 | 1.73 | 378 | 1.49 | 454 | 1.78 | 530 | 242 |
| 75 | 1.32 | 151 | 1.08 | 227 | 1.38 | 303 | 1.93 | 379 | 224 | 455 | 1.73 | 531 | 1.41 |
| 76 | 2.14 | 152 | 1.03 | 228 | 1.33 | 304 | 1.71 | 380 | 1.87 | 456 | 1.57 | 532 | 1.29 |

a
Vehicle
1 µM OT-9
5 µM OT-9
10 µM OT-9
b
Fusion index
1.00
0.95
0.90
0.85
0.80
*
Veh
1
5
10
OT-9 (µM)
c
MYOG mRNA (R.U.)
2.0
1.5
1.0
0.5
0.0
*
*
Veh
1
5
10
OT-9 (µM)

a
Sarcospan
extracellular
NH2
COO-
b
SSPN protein (R.U.)
2.0
1.5
1.0
0.5
D0
D1
D2
D3
D4
D5
day of differentiation
c
SSPN protein (R.U.)
1.5
1.0
0.5
0.0
Vehicle
GW5074
d
SSPN protein (R.U.)
2.5
2.0
1.5
1.0
0.5
0.0
12-well
384-well
OT-9
Veh
0.5 μM
1 μM
2.5 μM
5.5 μM
7.5 μM
10 μM

FIG. 13

| Compound | Incubation Time (minutes) | % Compound Remaining | | | Half-Life (minutes) | | |
|---|---|---|---|---|---|---|---|
| | | 1st | 2nd | Mean | 1st | 2nd | Mean |
| OT-9 | 0 | 100.0 | 100.0 | 100 | 470.7 | 452.4 | 462 |
| | 30 | 94.0 | 89.5 | 92 | | | |
| | 60 | 84.7 | 86.3 | 86 | | | |
| | 120 | 78.3 | 78.1 | 78 | | | |
| | 1440 | 11.6 | 10.5 | 11 | | | |
| PC1-36 | 0 | 100.0 | 100.0 | 100 | 644.4 | 643.2 | 644 |
| | 30 | 94.8 | 88.2 | 92 | | | |
| | 60 | 71.0 | 69.6 | 70 | | | |
| | 120 | 43.7 | 48.5 | 46 | | | |
| | 1440 | 17.3 | 17.2 | 17 | | | |

FIG. 14

| Compound | Incubation Time (minutes) | % Compound Remaining | | | Half-Life (minutes) | | |
|---|---|---|---|---|---|---|---|
| | | 1st | 2nd | Mean | 1st | 2nd | Mean |
| **OT-9** | 0 | 100.0 | 100.0 | 100 | 50.1 | 48.1 | 49 |
| | 30 | 28.3 | 33.8 | 31 | | | |
| | 60 | 9.8 | 10.1 | 10 | | | |
| | 120 | 3.6 | 2.5 | 4 | | | |
| | 240 | 2.7 | 2.1 | 2 | | | |
| | 1440 | 0.6 | 0.5 | 1 | | | |
| **PC1-36** | 0 | 100.0 | 100.0 | 100 | 131.5 | 140.4 | 136 |
| | 30 | 81.5 | 79.7 | 81 | | | |
| | 60 | 66.8 | 55.9 | 61 | | | |
| | 120 | 37.1 | 46.4 | 46 | | | |
| | 240 | 27.5 | 29.0 | 28 | | | |
| | 1440 | 0.8 | 1.0 | 1 | | | |

COMPOSITIONS AND METHODS FOR TREATING MUSCULAR DYSTROPHIES

RELATED APPLICATIONS

This application is the § 371 National Stage of PCT/US21/49362, filed on Sep. 8, 2021, which claims the benefit of U.S. Provisional Application No. 63/077,329, filed Sep. 11, 2020, and U.S. Provisional Application No. 63/148,823, filed Feb. 12, 2021, the contents of each of which are fully incorporated by reference herein.

GOVERNMENT SUPPORT

This invention was made with government support under HL126204, AR048179, and AR065972, awarded by the National Institutes of Health. The government has certain rights in the invention.

BACKGROUND

Muscular dystrophies span approximately thirty inherited disorders characterized by weakness and wasting away of muscle tissue, with or without the breakdown of nerve tissue. There are nine main types of muscular dystrophy, each of which involve an eventual loss of strength, increasing disability, and possible physical deformity. Duchenne muscular dystrophy (DMD), is the most well-known type of muscular dystrophy, affecting a proximately 1 in every 5,700 male births worldwide. DMD is caused by loss of sarcolemma adhesion to the extracellular matrix.

The development of therapies for DMD is gaining momentum with the recent accelerated approval of eteplirsen in 2016 and the increased private sector funding of rare disease programs. However, the existing FDA approved drugs for DMD are not sufficient to substantially slow disease progression. While corticosteroids dampen inflammation and ex end ambulation by several years, they do not address adhesion complex and membrane stability deficiencies. The antisense oligonucleotide exon skipping therapy eteplirsen increases truncated dystrophin protein production, but is only applicable to the approximately 14% of DMD patients with mutations amenable to exon 51 skipping. There remains a need to identify more robust treatments for muscular dystrophy and other muscle wasting diseases.

SUMMARY OF THE INVENTION

In certain embodiments, the present disclosure provides compounds represented by formula (I) or a pharmaceutically acceptable salt thereof:

(I)

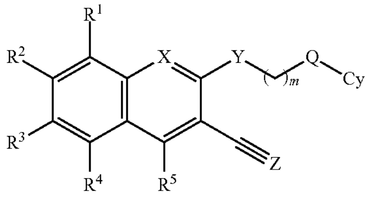

wherein

X is $CR^7$ or N;

Y is S, O or $SO_2$;

Z is N or $CR^6$;

$R^1$, $R^2$, $R^3$, $R^4$, $R^5$ and $R^7$ are each independently H, alkyl, alkoxy, halo, nitrile, amino or aminoalkyl;

$R^6$ is H or alkyl;

Q is C═O, SO or $SO_2$;

Cy is aryl or heteroaryl; and m is 1-3.

In certain embodiments, the present disclosure provides compounds represented by formula (II) or a pharmaceutically acceptable salt thereof:

(II)

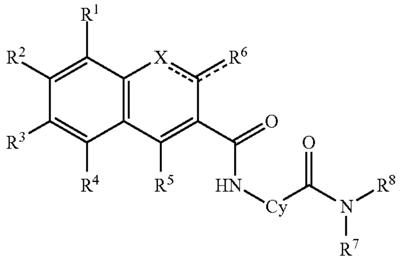

wherein

X is O, N or $NR^9$;

$R^1$, $R^2$, $R^3$, $R^4$ and $R^5$ are each independently H, alkyl, alkoxy, halo, nitrile, amino or aminoalkyl;

$R^6$ is H, ═O or alkyl;

Cy is aryl or heteroaryl;

$R^7$ and $R^8$ are each independently H or alkyl, or taken together with the atom to which they are attached form a heterocyclyl; and $R^9$ is H or alkyl.

In certain embodiments, the present disclosure provides methods of treating or preventing a disease related to dysfunction of a dystrophin-related complex.

BRIEF DESCRIPTION OF THE DRAWINGS

FIG. 7. Plate quality. Robust strictly standardized mean difference (SSMD*) was used to assess plate quality and for hit selection.

FIG. 13. Half-life of 1 μM of OT-9 and PC1-36 in CD-1 mouse plasma.

FIG. 14. Half-life of 1 μM of OT-9 and PC1-36 in PBS pH 7.4.

DETAILED DESCRIPTION OF THE INVENTION

Figure 1A:
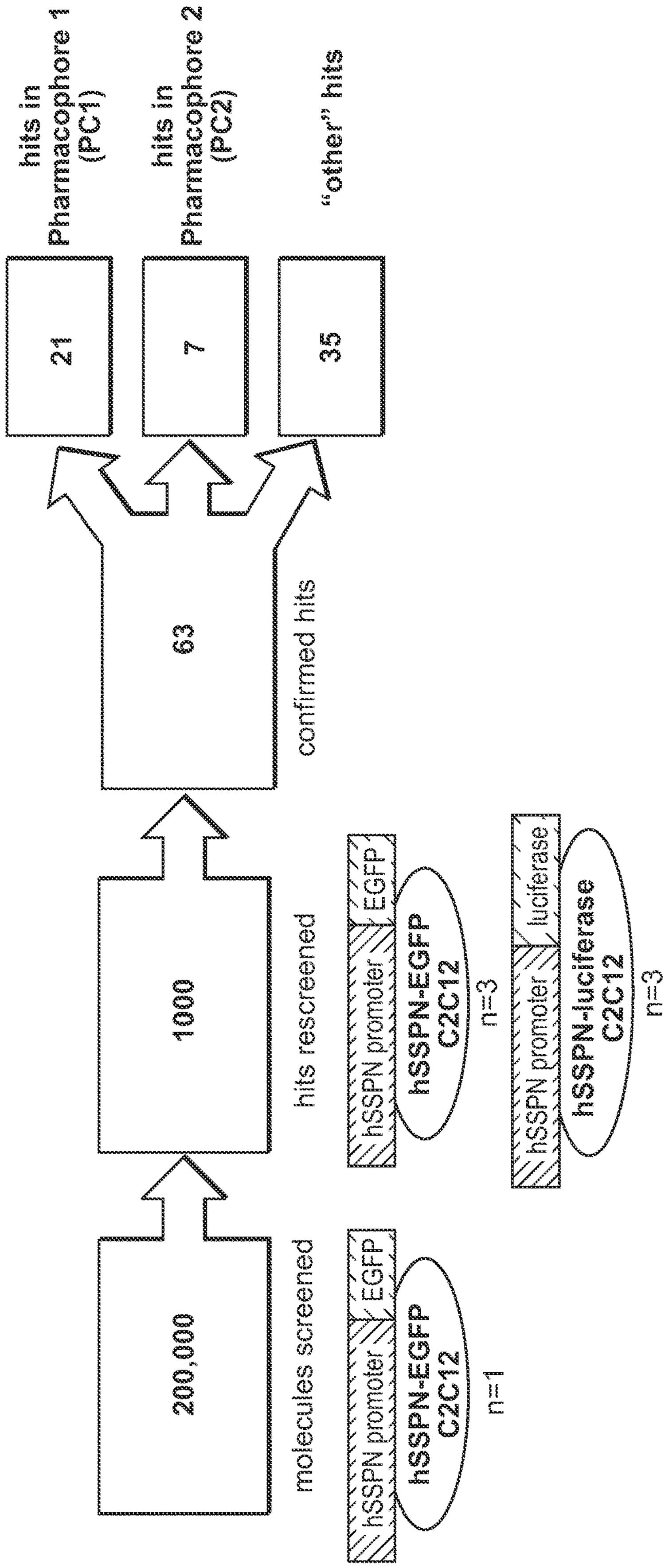
FIG. 1. Pipeline for high-throughput screening for sarcospan (SSPN) modulators. (a) Large chemical libraries were screened using the hSSPN-EGFP C2C12 reporter cell line (n=1). The top 1000 hits were rescreened in both hSSPN-EGFP and hSSPN-luciferase C2C12 reporter cell lines (n=3 each). 63 of the 1000 compounds increased reporter expression in both cell lines and were therefore considered confirmed hits. The confirmed hits were sorted into 3 groups based on common structural features: pharmacophore 1 (PC1), pharmacophore 2 (PC2), and other, which had no unifying structural theme. Dystrophin-deficient H2K mdx cells were treated with 5.5 μM of (b) pharmacophore 1 (PC1) or (c) other compounds for 48 hours. All cells were treated at day 2 of differentiation and harvested 48 hours post-treatment. Gene expression was normalized to housekeeping gene β-actin and vehicle-treated cells (0.5% DMSO). Data represents individual replicates and mean value. n=3-8. SSPN, sarcospan; R.U., relative units. $*p<0.05$, $p<0.01$, $*p<0.001$, $****p<0.0001$.

The heterogeneity of mutations and difficulty of delivery to muscle are major challenges to the development of therapies to treat DMD. There is an urgent need for improved therapies that can overcome these challenges. Sarcospan (SSPN) reduces the pathology of muscular dystrophy in the DMD murine model by increasing membrane localization of the utrophin-glycoprotein complex (UGC) and α7β1D-integrin adhesion complexes, effectively increasing laminin binding to compensate for the loss of dystrophin.

Development of small molecule therapies that increase SSPN expression may lead to standalone or combinatorial therapies to treat DMD and other forms of muscular dystrophy caused by deficits in membrane proteins. Small molecule therapies are ideal due to their ability to bypass the limitations of delivery and immune responses seen with viral and cell-based methods.

In certain embodiments, the present disclosure provides compounds represented by formula (I) or a pharmaceutically acceptable salt thereof:

(I)

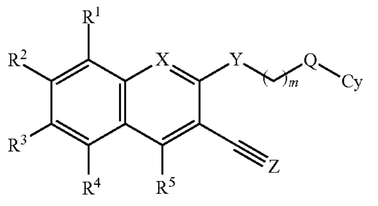

wherein

X is $CR^7$ or N;

Y is S, O or $SO_2$;

Z is N or $CR^6$;

$R^1$, $R^2$, $R^3$, $R^4$, $R^5$ and $R^7$ are each independently H, alkyl, alkoxy, halo, nitrile, amino or aminoalkyl;

$R^6$ is H or alkyl;

Q is C=O, SO or $SO_2$;

Cy is aryl or heteroaryl; and m is 1-3.

In certain embodiments, the present disclosure provides compounds represented by formula (II) or a pharmaceutically acceptable salt thereof:

(II)

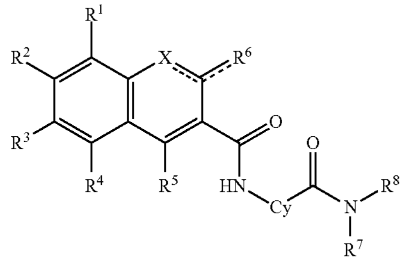

wherein

X is O, N or $NR^9$;

$R^1$, $R^2$, $R^3$, $R^4$ and $R^5$ are each independently H, alkyl, alkoxy, halo, nitrile, amino or aminoalkyl;

$R^6$ is H, =O or alkyl;

Cy is aryl or heteroaryl;

$R^7$ and $R^8$ are each independently H or alkyl, or taken together with the N atom to which they are attached form a heterocyclyl; and $R^9$ is H or alkyl.

In certain embodiments, the compound is selected from:

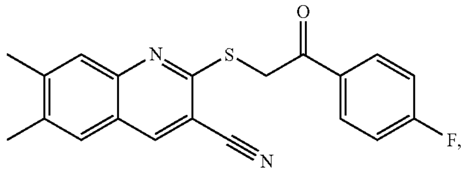

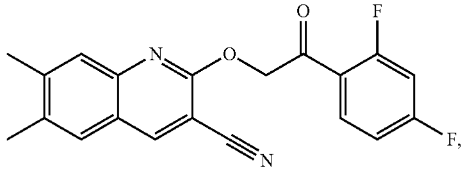

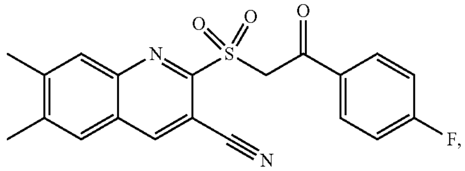

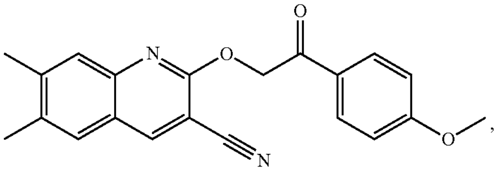

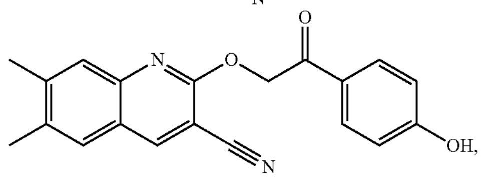

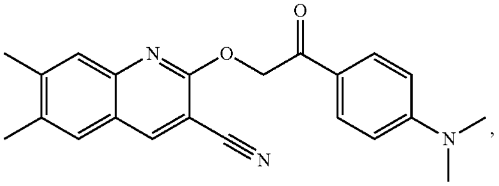

-continued
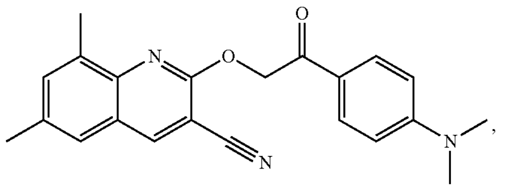
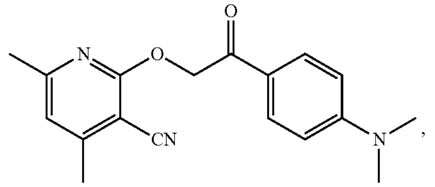
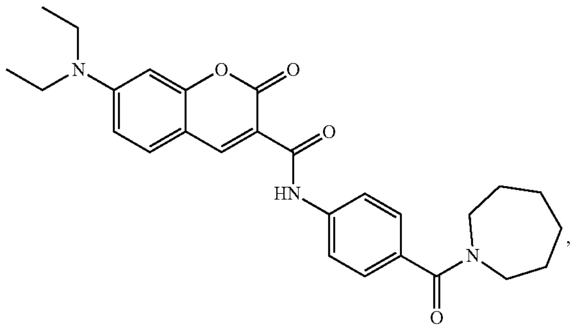
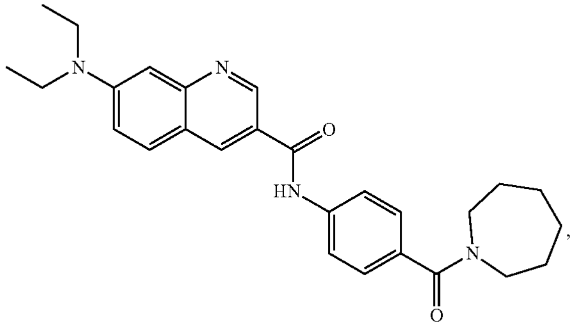
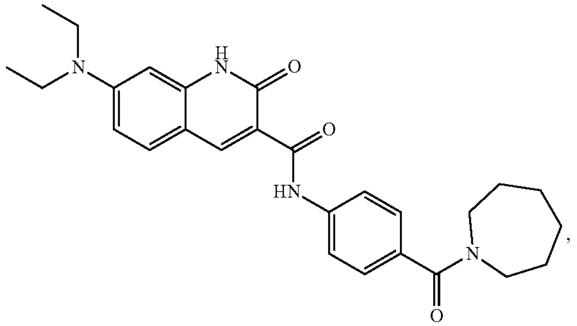
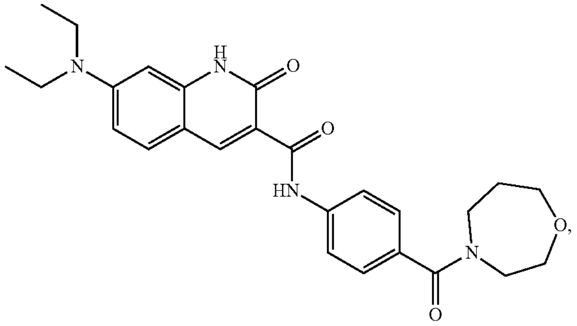
-continued
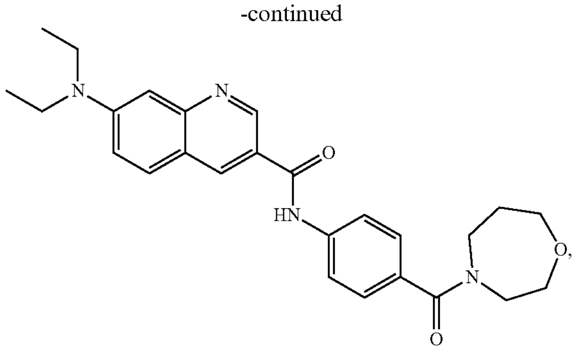
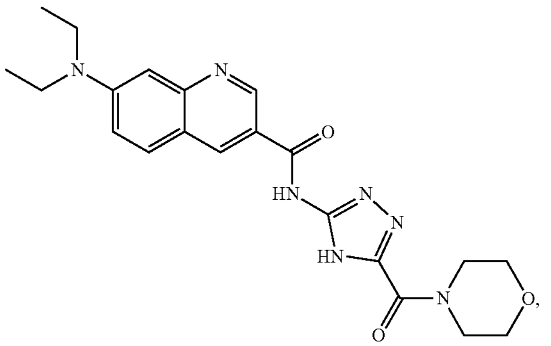
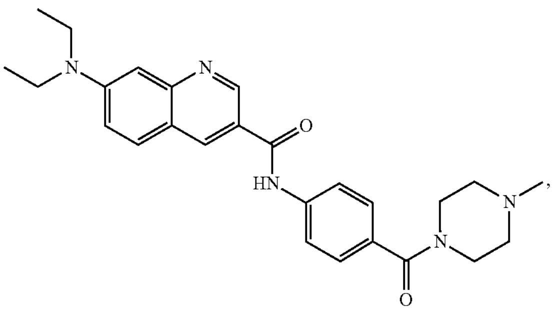
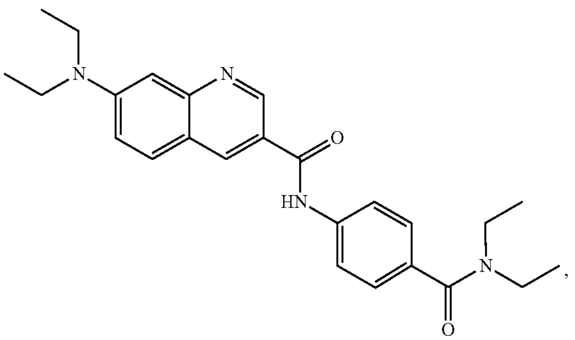
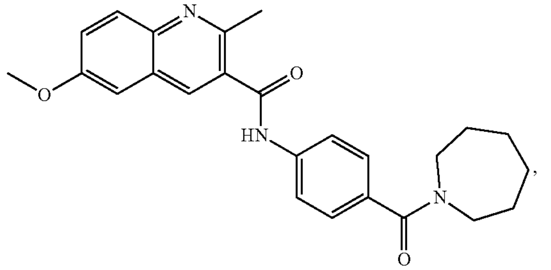

-continued

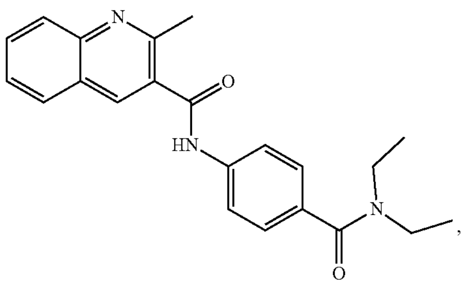

,

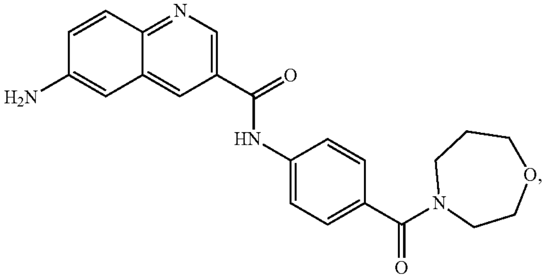

,

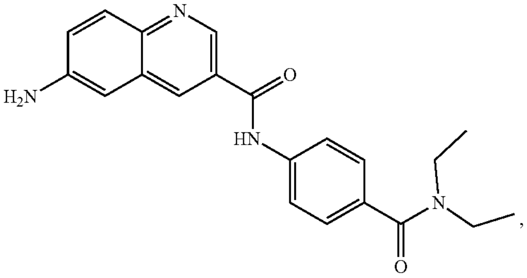

,

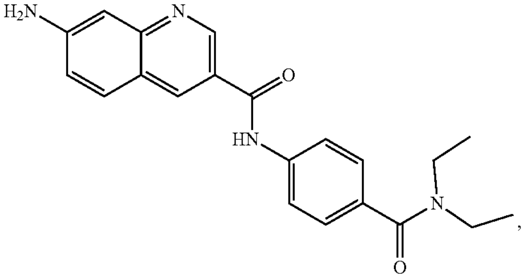

,

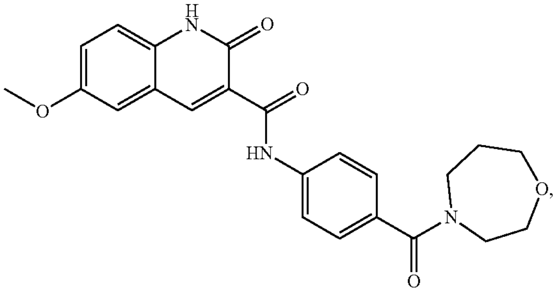

,

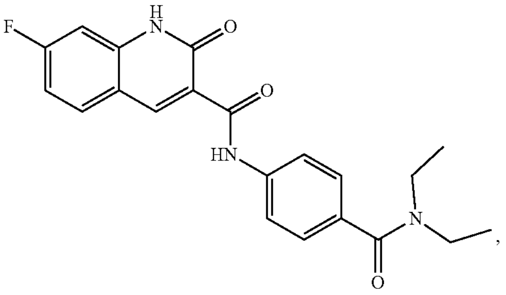

,

-continued

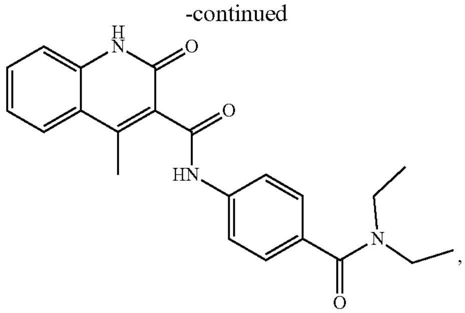

,

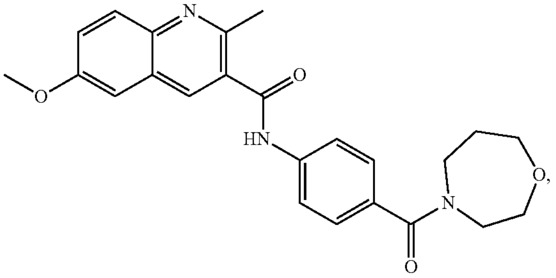

,

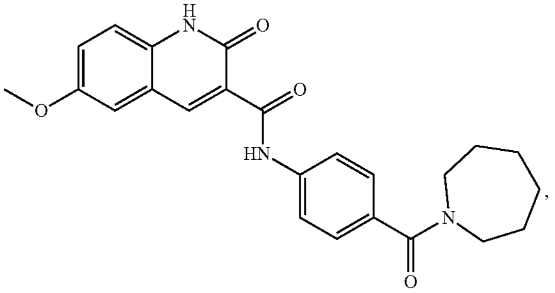

,

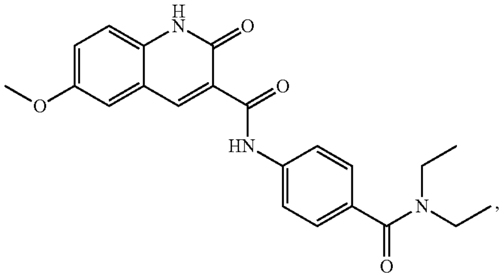

, and

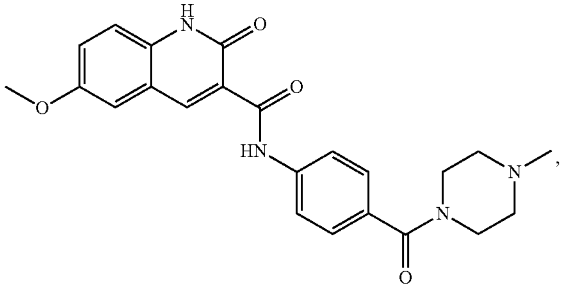

, or a pharmaceutically acceptable salt.

In another aspect, the present disclosure provides a composition comprising a compound of the disclosure and a pharmaceutically acceptable excipient.

In yet another aspect, the present disclosure provides methods of treating or preventing a disease related to dysfunction of a dystrophin-related complex in a subject in need thereof, comprising administering a compound of the disclosure or a pharmaceutically acceptable salt thereof to the subject.

In certain embodiments, the disease related to dysfunction of a dystrophin-related complex is a muscular dystrophy.

Pharmaceutical Compositions

The compositions and methods of the present invention may be utilized to treat an individual in need thereof. In certain embodiments, the individual is a mammal such as a human, or a non-human mammal. When administered to an animal, such as a h man, the composition or the compound is preferably administered as a pharmaceutical compositing comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrog n-free, or substantially pyrogen-free. The excipients can be chosen, for example, to effect dela ed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as a lotion, cream, or ointment.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-micro-emulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for e ample, drenches as in aqueous or non-aqueous solutions or suspensions, tablets, capsules (incl ding sprinkle capsules and gelatin capsules), boluses, powders, granules, pastes for application to the tongue); absorption through the oral mucosa (e.g., sublingually); subcutaneously; transdermally (for example as a patch applied to the skin); and topically (for example, as a cream, ointment or spray applied to the skin). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a tale, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pill and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow-release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans; and other mammals such as equines, cattle, swine, sheep, cats, and dogs; poultry; and pets in general.

In certain embodiments, compounds of the invention may be used alone or conjointly administered with another type of therapeutic agent.

The present disclosure includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts. In certain embodiments, contemplated salts of t e invention include, but are not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, 1-ascorbic acid, 1-aspartic acid, benzenesulfonic acid, benzoic acid, (+)-camphoric acid, (+)-camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, d-glucoheptonic acid, d-gluconic acid, d-glucuronic acid, glutamic acid, glutaric acid, glycerophosphoric acid, glycolic acid, hippuric acid, hydrobromic acid, hydrochloric acid, isobutyric acid, lactic acid, lactobionic acid, lauric acid, maleic acid, 1-malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, 1-pyroglutamic acid, salicylic acid, sebacic acid, stearic acid, succinic acid, sulfuric acid, 1-tartaric acid, thiocyanic acid, p-toluenesulfonic acid, trifloroacetic acid, and undecylenic acid acid salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well-known and commonly used in the art.

The methods and techniques of the present disclosure are generally performed, unless otherwise indicated, according to conventional methods well known in the art and as described in various general and more specific references that are cited and discussed throughout this specification. See, e.g., "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y. (1999); and Gilbert et al., "Developmental Biology, 6th ed.", Sinauer Associates, Inc., Sunderland, MA (2000).

Chemistry terms used herein, unless otherwise defined herein, are used according to conventional usage in the art, as exemplified by "The McGraw-Hill Dictionary of Chemical Terms", Parker S., Ed., McGraw-Hill, San Francisco, C.A. (1985).

All of the above, and any other publications, patents and published patent applications referred to in this application are specifically incorporated by reference herein. In case of conflict, the present specification, including its specific definitions, will control.

The term "agent" is used herein to denote a chemical compound such as an organic or inorganic compound, a mixture of chemical compounds), a biological macromolecule (such as a nucleic acid, an antibody, including parts thereof as well as humanized, chimeric and human antibodies and monoclonal antibodies, a protein or portion thereof, e.g., peptide, a lipid, a carbohydrate), or an extract made from biological materials such as bacteria, plants, fungi, or animal (particularly mammalian) cells or tissues. Agents include, for example, agents whose structure is known, and those whose structure is not known. The ability of such agents to inhibit AR or promote AR degradation may render them suitable as "therapeutic agents" in the methods and compositions of this disclosure.

A "patient," "subject," or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

"Treating" a condition or patient refers to taking steps to obtain beneficial or desired results, including clinical results. As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the co position. Thus, prevention of cancer includes, for example, reducing the number of detectable cancerous growths in a population of patients receiving a prophylactic treatment relative to n untreated control population, and/or delaying the appearance of detectable cancerous growths in a treated population versus an untreated control population, e.g., by a statistically and/or clinically significant amount.

"Administering" or "administration of" a substance, a compound or an agent to a subject can be carried out using one of a variety of methods known to those skilled in the art. For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods.

Appropriate methods of administering a substance, a compound or an agent to a subject will also depend, for example, on the age and/or the physical condition of the subject and the chemical and biological properties of the compound or agent (e.g., solubility, digestibility, bioavailability, stability and toxicity). In some embodiments, a compound or an agent is administered orally, e.g., to a subject by ingestion. In some embodiments, the orally administered compound or agent is in an extended release or slow-release formulation, or administered using a device for such slow or extended release.

As used herein, the phrase "conjoint administration" refers to any form of administration of two or more different therapeutic agents such that the second agent is administered while the previously administered therapeutic agent is still effective in the body (e.g., the two agents are simultaneously effective in the patient, which may include synergistic effects of the two agents). For example, the different therapeutic compounds can be administered either in the same formulation or in separate formulations, either concomitantly or sequentially. Thus, an individual who receives such treatment can benefit from a combined effect of different therapeutic agents.

A "therapeutically effective amount" or a "therapeutically effective dose" of a drug or agent is an amount of a drug or an agent that, when administered to a subject will have the intended therapeutic effect. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, and the nature and extent of the condition being treated, such as cancer or MDS. The skilled worker can readily determine the effective amount for a given situation by routine experimentation.

As used herein, the terms "optional" or "optionally" mean that the subsequently described event or circumstance may occur or may not occur, and that the description includes instances where the event or circumstance occurs as well as instances in which it does not. For example, "optionally substituted alkyl" refers to the alkyl may be substituted as well as where the alkyl is not substituted.

It is understood that substituents and substitution patterns on the compounds of the present invention can be selected by one of ordinary skilled person in the art to result chemically stable compounds which can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, the term "optionally substituted" refers to the replacement of one to six hydrogen radicals in a given structure with the radical of a specified substituent including, but not limited to: hydroxyl, hydroxyalkyl, alkoxy, halogen, alkyl, nitro, silyl, acyl, acyloxy, aryl, cycloalkyl, heterocyclyl, amino, aminoalkyl, cyano, haloalkyl, haloalkoxy, —OCO—$CH_2$—O-alkyl, —OP(O)(O-alkyl)$_2$ or —$CH_2$—OP(O)(O-alkyl)$_2$. Preferably, "optionally substituted" refers to the replacement of one to four hydrogen radicals in a given structure with the substituents mentioned above. More preferably, one to three hydrogen radicals are replaced by the substituents as mentioned above. It is understood that the substituent can be further substituted.

As used herein, the term "alkyl" refers to saturated aliphatic groups, including but not limited to $C_1$-$C_{10}$ straight-chain alkyl groups or $C_1$-$C_{10}$ branched-chain alkyl groups. Preferably, the "alkyl" group refers to $C_1$-$C_6$ straight-chain alkyl groups or $C_1$-$C_6$ branched-chain alkyl groups. Most preferably, the "alkyl" group refers to $C_1$-$C_4$ straight-chain alkyl groups or $C_1$-$C_4$ branched-chain alkyl groups. Examples of "alkyl" include, but are not limited to, methyl, ethyl, 1-propyl, 2-propyl, n-butyl, sec-butyl, tert-butyl, 1-pentyl, 2-pentyl, 3-pentyl, neo-pentyl, 1-hexyl, 2-hexyl, 3-hexyl, 1-heptyl, 2-heptyl, 3-heptyl, 4-heptyl, 1-octyl, 2-octyl, 3-octyl or 4-octyl and the like. The "alkyl" group may be optionally substituted.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkyl" refers to saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_{1-30}$ for straight chains, $C_{3-30}$ for branched chains), and more preferably 20 or fewer.

Moreover, the term "alkyl" as used throughout the specification, examples, and claims is intended to include both unsubstituted and substituted alkyl groups, the latter of which refers to alkyl moieties having substituents replacing a hydrogen on one or more carbons of the hydrocarbon backbone, including haloalkyl groups such as trifluoromethyl and 2,2,2-trifluoroethyl, etc.

The term "$C_{x-y}$" or "$C_x$-$C_y$", when used in conjunction with a chemical moiety, such as, acyl, acyloxy, alkyl, alkenyl, alkynyl, or alkoxy is meant to include groups that contain from x to y carbons in the chain. $C_0$alkyl indicates a hydrogen where the group is in a terminal position, a bond if internal. A $C_{1-6}$alkyl group, for example, contains from one to six carbon atoms in the chain.

The term "alkylamino", as used herein, refers to an amino group substituted with at least one alkyl group.

The term "alkylthio", as used herein, refers to a thiol group substituted with an alkyl group and may be represented by the general formula alkylS—.

The term "amide", as used herein, refers to a group

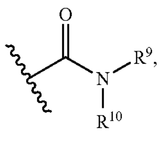

wherein $R^9$ and $R^{10}$ each independently represent a hydrogen or hydrocarbyl group, or $R^9$ and $R^{10}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

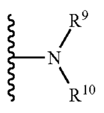
or
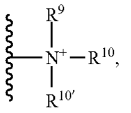

wherein $R^9$, $R^{10}$, and $R^{10'}$ each independently represent a hydrogen or a hydrocarbyl group, or $R^9$ and $R^{10}$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

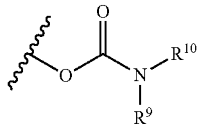
or
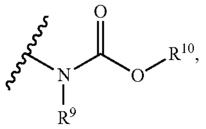

wherein $R^9$ and $R^{10}$ independently represent hydrogen or a hydrocarbyl group.

The term "carbocyclylalkyl", as used herein, refers to an alkyl group substituted with a carbocycle group.

The term "carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

The term "carbocyclylalkyl", as used herein, refers to an alkyl group substituted with a carbocycle group.

The term "carbonate" is art-recognized and refers to a group $—OCO_2—$.

The term "carboxy", as used herein, refers to a group represented by the formula $—CO_2H$.

The term "ester", as used herein, refers to a group $—C(O)OR^9$ wherein $R^9$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to our heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The term "heterocyclylalkyl", as used herein, refers to an alkyl group substituted with a heterocycle group.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "hydrocarbyl", as used herein, refers to a group that is bonded through a carbon atom that does not have a =O or =S substituent, and typically has at leas one carbon-hydrogen bond and a primarily carbon backbone, but may optionally include heteroatoms. Thus, groups like methyl, ethoxyethyl, 2-pyridyl, and even trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "sulfate" is art-recognized and refers to the group $-OSO_3H$, or a pharmaceutically acceptable salt thereof.

The term "sulfonamide" is art-recognized and refers to the group represented by the general formulae

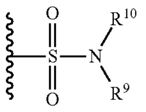

or

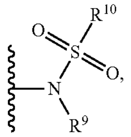

wherein $R^9$ and $R^{10}$ independently represents hydrogen or hydrocarbyl.

The term "sulfoxide" is art-recognized and refers to the group-S(O)—.

The term "sulfonate" is art-recognized and refers to the group $SO_3H$, or a pharmaceutically acceptable salt thereof.

The term "sulfone" is art-recognized and refers to the group $-S(O)_2-$.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

The term "thioalkyl", as used herein, refers to an alkyl group substituted with a thiol group.

The term "thioester", as used herein, refers to a group $-C(O)SR^9$ or $-SC(O)R^9$ wherein $R^9$ represents a hydrocarbyl.

The term "thioether", as used herein, is equivalent to an ether, wherein the oxygen is replaced with a sulfur.

The term "urea" is art-recognized and may be represented by the general formula

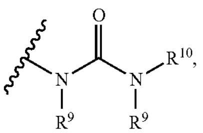

wherein $R^9$ and $R^{10}$ independently represent hydrogen or a hydrocarbyl.

The term "modulate" as used herein includes the inhibition or suppression of a function or activity (such as cell proliferation) as well as the enhancement of a function or activity.

The phrase "pharmaceutically acceptable" is art-recognized. In certain embodiments, the term includes compositions, excipients, adjuvants, polymers and other materials and/or dosage forms which are, within the scope of sound medical judgment, suitable f r use in contact with the tissues of human beings and animals without excessive toxicity, irritation, allergic response, or other problem or complication, commensurate with a reasonable benefit/risk ratio.

"Pharmaceutically acceptable salt" or "salt" is used herein to refer to an acid addition salt or a basic addition salt which is suitable for or compatible with, the treatment of patients.

The term "pharmaceutically acceptable acid addition salt" as used herein means any non-toxic organic or inorganic salt of any base compounds represented by Formula I. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of compounds of Formula I are more soluble in water and various hydrophilic organic solvents, and generally demonstrate higher melting points in comparison to their free base forms. The select on of the appropriate salt will be known to one skilled in the art. Other non-pharmaceutically acceptable salts, e.g., oxalates, may be used, for example, in the isolation of compounds of Formula I for laboratory use, or for subsequent conversion to a pharmaceutically acceptable acid addition salt.

The term "pharmaceutically acceptable basic addition salt" as used herein means any non-toxic organic or inorganic base addition salt of any acid compounds represented by Formula I or any of their intermediates. Illustrative inorganic bases which form suitable salts include lithium, sodium, potassium, calcium, magnesium, or barium hydroxide. Illustrative organic bases which form suitable salts include aliphatic, alicyclic, or aromatic organic amines such as methylamine, trimethylamine and picoline or ammonia. The selection of the appropriate salt will be known to a person skilled in the art.

Many of the compounds useful in the methods and compositions of this disclosure have at least one stereogenic center in their structure. This stereogenic center may be present in a R or a S configuration, said R and S notation is used in correspondence with the rules described in Pure Appl. Chem. (1976), 45, 11-30. The disclosure contemplates all stereoisomeric forms such as enantiomeric and diastereoisomeric forms of the compounds, salts, prodrugs or mixtures thereof (including all possible mixtures of stereoisomers). See, e.g., WO 01/062726.

Furthermore, certain compounds which contain alkenyl groups ay exist as Z (zusammen) or E (entgegen) isomers. In each instance, the disclosure includes both mixture and separate individual isomers.

Some of the compounds may also exist in tautomeric forms. Such forms, although not explicitly indicated in the formulae described herein, are intended to be included within the scope of the present disclosure.

"Prodrug" or "pharmaceutically acceptable prodrug" refers to a compound that is metabolized, for example hydrolyzed or oxidized, in the host after administration to form the compound of the present disclosure (e.g., compounds of formula I). Typical examples of prodrugs include compounds that have biologically labile or cleavable (protecting) groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. Examples of prodrugs using ester or phosphoramidate as biologically labile or cleavable (protecting) groups are disclosed in U.S. Pat. Nos. 6,875,751, 7,585,851, and 7,964,580, the disclosures of which are incorporated herein by reference. The prodrugs of this disclosure are metabolized to produce a compound of Formula I. The present disclosure includes within its scope, prodrugs of the compounds described herein. Conventional procedures for the selection and preparation of suitable prodrugs are described, for example, in "Design of Prodrugs" Ed. H. Bundgaard, Elsevier, 1985.

The phrase "pharmaceutically acceptable carrier" as used herein jeans a pharmaceutically acceptable material, composition or vehicle, such as a liquid or solid filter, diluent, excipient, solvent or encapsulating material useful for formulating a drug for medicinal or therapeutic use.

The term "Log of solubility", "Log S" or "log S" as used herein is used in the art to quantify the aqueous solubility of a compound. The aqueous solubility f a compound significantly affects its absorption and distribution characteristics. A low solubility often goes along with a poor absorption. Log S value is a unit stripped logarithm (base 10) of the solubility measured in mol/liter.

EXAMPLES

The invention now being generally described, it will be more readily understood by reference to the following examples which are included merely for purposes of illustration of certain aspects and embodiments of the present invention, and are not intended to limit the invention.

Methods

Reporter Cell Lines

The human sarcospan EGFP reporter C2C12 cell line (hSSPN-EGFP) was used as described by Shu et al., Skelet Muscle. 2019; 9(1):32. Using an identical approach, a human sarcospan luciferase (hSSPN-luc) C2C12 cell line was created and used in secondary screening.

Small Molecules

Screening libraries were provided by the Molecular Screen Shar d Resource at the University of California Los Angeles. Commercially available compounds used in follow-up studies were purchased from Asinex and Life Chemicals Inc.

High-Throughput Screening hSSPN-EGFP myoblasts were seeded at 500 cells per well in 50 μl of growth medium in 384-well black, clear bottom microplates (Greiner) using a Multidrop 384 (Thermo Fisher Scientific) and incubated for 3 days to allow cells to reach confluency. Upon reaching confluency, the growth medium was replaced with 50 μl of differentiation medium consisting of DMEM with 2% horse serum (Sigma-Aldrich) using an EL406 combination washer dispenser (Biotek). At day 2 of differentiation, the medium on the cells was aspirated, left with a residual volume of 10 μl, and replaced with 30 μl of fresh differentiation medium. 0.5 μl of small molecule in DMSO or DMSO alone (for vehicle and positive control wells) was added to each well using a Biomek Fx (Beckman). To ensure proper mixing of the DMSO, 50 μl of additional differentiation medium was added to all wells except the positive control treated wells, which instead received 50 μl of medium containing insulin transferrin selenium (ITS) (Gibco) to reach a final concentration of 1% ITS. The final concentration of compound in each treated well was 5.5 μM in 0.55% DMSO and 0.55% DMSO only for vehicle and positive control treated wells. After 48 hrs of incubation, the medium was replaced with Fluorobrite DMEM (Gibco) and each plate was imaged using ImageXpress Micro Confocal High Content Imaging System (Molecular Devices). The fluorescence intensity of imaged cells was determined using a custom module analysis in MetaXpress Analysis software (Molecular Devices). Analysis setting were as follows: top hat (size: 12, filter shape: circle), adaptive threshold (source: top hat, minimum width: 10, maximum width: 800, intensity above local background: 500), filter mask (filter type: minimum area filter, minimum value: 500).

Luciferase Assay hSSPN-luciferase myoblasts were cultured as described above. After 48 hrs of treatment, plates were allowed to equilibrate to RT. The cell culture medium in each well was aspirated using an EL406 combination washer dispenser. Bright-Glo luciferase assay system reagent (Promega) and differentiation medium were added to cells at a 1:2 dilution using a Multidrop 384. After a 3-minute incubation at RT, luminescence signal was quantified using an Envision plate reader (PerkinElmer). The relative luminescence units were analyzed to determine fold change of treated over vehicle treated cells.

Cell Culture

C2C12 cells (American Type Culture Collection) were grown at 37° C. with 5% $CO_2$ in growth medium containing DMEM (Gibco) with 20% FBS (Sigma-Aldrich). Upon reaching 90-100% confluency, myoblasts were induced to differentiate by replacing the medium with differentiation medium consisting of DMEM with 2% horse serum (Sigma-Aldrich). Conditionally immortalized H2K WT and mdx myoblasts with a nonsense mutation in exon 23 of dystrophin were a gift from Terrance Partridge, Ph.D. (Children's National Medical Center, Washington, D.C.). See, Morgan et al., Dev Biol. 1994; 162(2):486-98 Myoblasts were allowed to proliferate on 0.01% gelatin (Sigma-Aldrich) coated plates at 33° C. with 5% $CO_2$ with growth medium containing DMEM, 20% HI-FBS (Invitrogen), 2% L-glutamine (Sigma-Aldrich), 2% chicken embryo extract (Accurate Chemical), 1% penicillin-streptomycin (Sigma-Aldrich), and 20 U/ml of fresh interferon gamma (Gibco). For differentiation, H2K myoblasts were seeded on plates coated with 0.1 mg/ml matrigel (Corning) diluted in DMEM and grown in proliferation conditions. Upon reaching 90-100% confluency, cells were grown at 37° C. with 5% $CO_2$ in differentiation medium containing DMEM with 5% horse serum (Sigma-Aldrich), 2% L-glutamine, and 1% penicillin-streptomycin using established protocols.

Gene Expression Analysis

RNA from myotubes treated for 48 hrs was extracted from cells using Trizol-based (Thermo Fisher Scientific) phase separation, Chomczynski et al., Biotechniques. 1993; 15(3): 532-4, 6-7. RNA concentrations were determined using a NanoDrop 1000 (Thermo Fisher Scientific) and 750 ng of RNA in a 20 μl reaction was reverse transcribed using iScript cDNA synthesis (Bio-Rad) with the following cycling conditions: 25° C. for 5 mins, 42° C. for 30 mins, 85° C. for 5 mins. For mouse qPCR, SsoFast EvaGreen Supermix Bio-Rad), 400 nM of each optimized forward and reverse primer (SSPN F: 5' TGCTAGTCAGAGATACTCCGTTC 3', SSPN R: 5' GTCCTCTCGTCAACTTGGTATG 3', BACT F: 5' GAGCACCCTGTGCTGCTCACCG 3', BACT R: 5' CAATGCCTGTGGTACGACCA 3'), and cDNA corresponding to 37.5 ng RNA were used to amplify cDNA measured by QuantStudio 5 Real-Time PCR System (Thermo Fisher Scientific) with the following reaction conditions: 55° C. for 2 mins, 95° C. for 2 mins, 40 cycles of 95° C. for 10 seconds and 62° C. for 30 seconds, and dissociation stage. For qPCR of human samples, TaqMan assays were used to quantify SSPN (assay ID Hs01025520m_1) and ACTB (assay ID Hs01060665_g1) with the following reaction conditions: 50° C. for 2 mins, 95° C. for 10 mins, 40 cycles of 95° C. for 15 seconds and 62° C. for 1 minute. Each sample was run in triplicate. Data was analyzed using the ddCT method and normalized to reference gene ACTB with vehicle-treated samples serving as the calibrator (relative expression of vehicle control=1).

Immunoblotting

Myotubes treated for 48 hrs were lysed using RIPA buffer (Thermo Fisher Scientific) containing Halt Protease Inhibitor Cocktail (Thermo Fisher Scientific). Cell lysates in RIPA buffer were rocked for 1 hr at 4° C. and centrifuged at 1,000 RPM for 30 mins at 4° C. The supernatant was collected, quantified for protein concentration using the DC protein assay (Bio-Rad), and normalized to 2 mg/ml in water and Laemmli sample buffer with a final concentration of 10% glycerol (Sigma-Aldrich), 5% beta-mercaptoethanol (Sigma-Aldrich), 3% sodium dodecyl sulfate (Sigma-Aldrich), and 0.05% bromophenol blue (Sigma-Aldrich). For SDS-PAGE, samples were heated to 95° C. for 2 mins before loading 40 μg onto 4-12% tris-glycine or bis-tris polyacrylamide gels (Novex), electrophoresed for 2 hrs at 100 volts at RT, and transferred to a nitrocellulose membrane for 2 hrs at 100 volts at 4° C. Ponceau S staining was performed to visualize protein loading and verify protein transfer. Membranes were blocked with 5% non-fat dried milk in tris-buffered saline pH 7.4 with 0.1% tween-20 (Sigma-Aldrich) (TBST) for 1 hr at RT and incubated on a rocker overnight at 4° C. with t e following primary antibodies diluted in blocking buffer containing 5% non-fat dry milk (Carnation) unless otherwise noted: SSPN (sc-393187, Santa Cruz Biotechnology, 1:200), glycosylated alpha-dystroglycan (IIH6 C4, Developmental Studies Hybridoma Bank, 1:100 in 1% milk, core alpha-dystroglycan (Beadle Lab, 1:1000 in 1% milk), UTRN (MANCHO3, Developmental Studies Hybridoma Bank, 1:100), and GAPDH (Mab374, Millipore, 1:10,000). Following three 10-minute TBST washes, the membranes were incubated in goat anti-mouse IgG HRP (ab6789, Abcam, 1:5000 for all, 1:10,000 for GAPDH in 5% milk) or goat anti-rabbit IgG HRP (ab6721, Abcam, 1:10, 000 in 1% milk) for 1 hr at RT. The membranes were then washed three times for 10 mins each with TBST, incubated in SuperSignal West Pico Chemiluminescent Substrate (Thermo Fisher Scientific) for 5 mins at RT on an orbital shaker, and exposed to autoradiography films (Agfa). Autoradiography films were developed using a SRX-101 tabletop processor (Konica Minolta), scanned to a digital file, and analyzed by densitometry of bands using ImageJ version 1.51s. Target protein bands were normalized to loading control GAPDH with vehicle-treated cells serving as the calibrator sample (relative protein levels of vehicle control=1).

C2C12 SSPN-HiBiT Assay in 12-Well Plate Format

C2C12 SSPN-HiBiT myoblasts were seeded at 25,000 cells per well in 2 ml of growth media in 12 well-plates and incubated for 3 days. Upon reaching confluency, the growth media was replaced with 2 ml of differentiation media. At day 2 of differentia ion, the media on the cells was replaced with 2 ml of differentiation media containing compounds at a final concentration of 5.5 μM in 0.06% DMSO. For vehicle control-treated cells, 0.06% DMSO was added to the cells. After 48 hrs the cells were washed with PBS and frozen for 2-24 hrs. The plates containing cells were thawed on ice and 100 μl of ice-cold modified RIPA buffer containing 1% Triton X-100, 0.05% DOC, 0.05% SDS, and Halt Protease Inhibitor was added to each well. Cells were scratched, transferred into 1.5 ml tubes, and centrifuged for 20 min at 16,000×g at 4° C. The cell lysates were transferred into new tubes. DC assay was performed on cell lysates to determine protein concentration. White walled, white bottom 384-well microplates (Greiner) were prefilled with 15 μl of PBS and 15 μl of cell lysates were added to each well in triplicate. Then 30 μl Nano-Glo HiBiT Lytic Detection working solution was added to each well and incubated for 30 min at RT with shaking. The luminescence was measured on the EnVision plate reader and the signal was normalized to protein concentration and signal from vehicle-treated controls.

C2C12 SSPN-HiBiT Assay in 384-Well Microplate Format

C2C12 SSPN-HiBiT myoblasts were seeded at 500 cells per well in 50 μl of growth media in 384-well white, clear bottom microplates (Greiner) and incubated for 3 days. Upon reaching confluency, the growth media was replaced with 50 μl of differentiation media consisting of phenol-red free DMEM with 2% horse serum (Sigma-Aldrich) using an EL406 combination washer dispenser (Biotek). At day 2 of differentiation, the media on the cells was aspirated, left with a residual volume of 10 μl, and replaced with 30 μl of fresh differentiation media. 0.5 μl of small molecule in DMSO or DMSO alone (for vehicle and positive control wells) were added to each well using a Biomek Fx (Beckman). To ensure proper mixing of the DMSO, 50 μl of additional differentiation media was added to all wells except the positive control treated wells. The final concentration of compound in each treated well was 0.5-10 μM in 0.55% DMSO and 0.55% DMSO only for vehicle. After 48 hrs of incubation, the plate was washed with phenol red-free DMEM, aspirated, and left with a residual volume of 5 μl using EL406 combination washer dispenser. After the wash, 25 μl of differentiation media containing 12 μM DRAQ5 nuclear stain was added to reach a final concentration 10 μM in each well and incubated for 15 min at 37° C. with 5% $CO_2$. The cells were imaged using ImageXpress Micro Confocal High Content Imaging System (Molecular Devices). The nuclei count of imaged cells were determined using a custom module analysis in MetaXpress Analysis software (Molecular Devices). After imaging and analysis, the plate was aspirated, left with a residual volume of 5 μl and placed at −80° C. for 2-24 hrs. The plate was thawed at RT and 25 μl of PBS was added, followed by 30 μl of Nano-Glo HiBiT Lytic Detection working solution prepared according manufacturer recommendations. Luminescence was measured using the EnVision plate reader and the signal of each well was normalized to nuclei count and signal from vehicle-treated controls.

Analysis of Cell Surface Proteins

After 48 hours of treatment, myotubes were washed with ice cold PBS containing 0.1 g/L of both $CaCl_2$ (0.9 mM) and $MgCl_2$ (1.05 mM) (Corning) three times and incubated in 0.5 mg/ml of EZ-Link Sulfo-NHS-SS-Biotin (Thermo Fisher Scientific) at 4° C. with gentle rotation for 30 mins to label cell surface proteins. All steps were performed at 4° C. unless otherwise mentioned. The cells were washed three times with ice cold 100 mM glycine in PBS for 5 mins with gentle rotation to remove non-reacted biotin. Following a PBS wash, the cells were lysed in solubilization buffer composed of 50 mM Tris-HCl pH 7.8, 500 mM NaCl, 1% digitonin (Biosynth), and Halt protease and phosphatase inhibitors. The samples were rotated 4° C. for 10 mins and centrifuged at 4° C. at 14,000 rpm for 20 mins to pellet debris. The DC assay (Bio-Rad) was used to determine the protein concentration of the supernatant (total lysate). Pierce High Capacity Neutravidin Agarose (Thermo Fisher Scientific) beads were washed with solubilization buffer before being combined with equal concentrations of total lysate and incubated at 4° C. overnight with rotation. The beads were centrifuged at 4° C. at 2,500 rpm for 5 mins and washed with solubilization buffer containing 0.1% digitonin. This was repeated for a total of 4 washes. The biotinylated cell surface proteins were cleaved from biotin-avidin using 2× Laemmli sample buffer (LSB) with 50 mM DTT, rotated at RT for 60 mins, and heated at 95° C. for 5 mins. The samples were centrifuged at 2,500 rpm at 4° C. for 5 mins and the supernatant (membrane fraction) was collected for immunoblot analysis.

Membrane Stability Assay

The membrane stability assay was modified from previously described methods [32]. The solutions for osmotic shock were prepared from a base solution containing 5 mM HEPES, 5 mM KCl, 1 mM $MgCl_2$, 5 mM NaCl, 1.2 mM $CaCl_2$, and 1 mM glucose. Sucrose was added to the base solutions to reach osmolarities of 50, 80, 100, 280, and 300 mosmol. The actual osmolarity was determined using a VAPRO vapor pressure osmometer (Wescor Inc.) Myotubes were treated for 48 hours and at day 4 of differentiation were subjected to 20 mins of osmotic shock at 37° C. using 28.5 to 223.5 milliosmole (mosmol) solutions. The supernatant was collected and centrifuged to separate cell debris. Adherent cells were trypsinized and pelleted before lysis with water and 3 freeze-thaw cycles. The Creatine Kinase Assay (Sekisui Diagnostics) was used to measure creatine kinase (CK) levels in both the supernatant and lysate fractions. In a 96-well plate, 4 μl of each sample and 140 μl of reagent was loaded per well in triplicate. The U/L of CK was calculated as follows: (mOD/min)(total volume in mL)(dilution factor)/(6.22M-1 cm-1)(light path in cm)(sample volume in mL). The percent CK release was calculated as follows: $CK_{extracellular}/(CK_{extracellular}+CK_{intracellular})*100$.

siRNA-Mediated Knockdown

Lipofectamine RNAiMAX Transfection Reagent (Life Technologies) was used to transfect H2K mdx myotubes with 24 or 48 nM of Silencer Select SSPN siRNA (siRNA ID s68932, Life Technologies) or MISSION siRNA Fluorescent Universal Negative Control #1, Cyanine 3 (Sigma Aldrich) diluted in Opti-MEM Reduced Serum Medium (Thermo Fisher Scientific). The transfection reagent and diluted siRNA were added to 1 ml of growth medium per well in a 24-well cell culture plate.

Myotube Fusion Index

Myoblasts in a 96-well plate were treated for 72 hrs beginning at day 2 of differentiation were fixed with 4% paraformaldehyde for 20 mins, permeabilized with 0.2% Triton X-100 (Sigma) for 10 mins, and blocked with 1% BSA for 30 mins. Myosin heavy chain (MHC) was detected using 10 μg/ml MF-20 (Developmental Hybridoma Studies Bank) in 1% BSA overnight and 10 μg/ml goat anti-mouse Alexa Fluor Plus 594 (Thermo Fisher Scientific) in 1% BSA for 1 hr. PBS washes were performed between each step above. Nuclei were stained with 5 μg/ml Hoechst (Thermo Fisher Scientific) for 20 mins before imaging. Each treatment was performed in three wells and three fields per well were captured. ImageJ was used to count the number of total nuclei and nuclei within a MHC positive cell. Fusion index was calculated as nuclei in a MHC positive cell/total nuclei.

Half-Life Analysis

Half-life analysis was performed by Eurofins Panlabs Inc. using 1 μM of compound with a final DMSO concentration of 0.5%. PBS or plasma from CD-1 mice was pre-warmed to 37° C. for 5 mins before addition of the test compounds and continued incubation at 37° C. At 0, 30, 60, 120, 240, and 1440 mins an aliquot of solution containing compounds was mixed with acetonitrile/methanol, mixed, and centrifuged. The supernatants were used for HPLC-MS/MS analysis.

In Vivo Treatment

For the preliminary safety assessment of OT-9, we performed IP injections in 6 month old C57/Bl6 males. The mice were injected with 100 μl of vehicle (5% DMSO (Sigma), 95% PBS), 100 μl of 30 mg/kg of OT-9 in vehicle, or 100 μl of 50 mg/kg of OT-9 in vehicle (n=1 mouse per treatment). The mice were observed for 72 hours, then sacrificed for visual evaluation of injection site and internal organs (data not shown). For assessment of activity, 20-weeks old male mdx littermates were injected in both tibialis anterior muscles with vehicle (5% DMSO, 95% PBS) or 86 μg of OT-9. Two mice were injected in both TAs with vehicle and three mice were injected in both TAs with 20 μl of OT-9 (9.4 mM solution containing 86 μg of OT-9).

After 4 hours, the muscles were harvested and processed for gene expression analysis. For assessment of activity of OT-9m after local administration, 19-22-weeks old mdx males were injected in both tibialis anterior muscles with vehicle (5% DMSO, 95% PBS) or 3 mg/kg and 10 mg/kg of OT-9m. After 4 hours, the muscles were harvested and processed for gene expression analysis. For assessment of activity of OT-9m after systemic administration, 13-weeks old mdx males were injected subcutaneously with vehicle (4% PEG-200 in hydroxypropyl-b-cyclodextrin) or 20 mg/kg/day of OT-9m. After 13 days of treatment, the muscles were harvested and processed for gene expression analysis.

Data Analysis

Robust strictly standardized mean difference (SSMD*) was used to assess plate quality and for hit selection.

$$SSMD^* = X_P - X_N / 1.4826\sqrt{s_P^2 + s_N^2},$$

where $X_P$, $X_N$, $S_P$, and $S_N$ are the medians and median absolute deviations of the positive and negative controls, respectively.[33] For plate quality, SSMD*≥1 indicates a good quality moderate positive control. For initial hit selection, a 1.4-fold increase over vehicle and SSMD*>0.25 was considered a hit. Statistical analysis was performed using Prism version 7.0 (GraphPad Software) for Mac OS X using the two-tailed, non-parametric Kolmogorov-Smirnov test. Data are reported as mean+SEM. A p-value of <0.05 was considered statistically significant. *p<0.05, p<0.01, *p<0.001, ****p<0.0001.

Results

We previously created and validated a muscle cell-based high-throughput assay to identify small molecule enhancers of human SSPN gene expression. Shu et al., Skelet Muscle. 2019; 9(1):32. Using the assay, we screened clinical compounds and demonstrated that the assay is capable of identifying small molecules that increase SSPN gene and protein expression in both wild-type and dystrophin deficient myotubes. Id. In this current study, we screened large chemical libraries with the goal of identifying compounds that can be developed into new chemical entity enhancers of SSPN. The curated libraries were develop d to maximize drug-likeness based on Lipinski's rule of 5, which defines parameters that ca be used to predict optimal oral bioavailability in humans.

High-Throughput Screening of 200,000 Small Molecules

High-throughput screening of over 200,000 small molecules from curated libraries was conducted using a cell-based assay for human SSPN gene expression. The reporter cells used in the assay were C2C12 murine myoblasts stably transfected with a construct containing the human SSPN promoter region followed by the coding sequence for enhanced green fluorescent protein (hSSPN-EGFP). Using the hSSPN-EGFP assay, we screened compounds at a concentration of 5.5 μM (n=1) (FIG. 1*a*). Plate quality was calculated using robust strictly standardized mean difference (SSMD*) (FIG. 7). To rule out assay-specific false positives, we counterscreened using a stably transfected reporter cell line containing a luciferase reporter for human SSPN promoter activity (hSSPN-luc). The top 1000 hits were rescreened in both hSSPN-EGFP (n=3) and hSSPN-luciferase promoter reporter myotubes (n=3). Of the 1000 hits, 63 compounds increased reporter expression in both reporter cell lines and were therefore considered confirmed hits. The confirmed hits were sorted into three groups based on common structural features: pharmacophore 1, pharmacophore 2, and the other category, which had no unifying structural features. Pharmacophore 2 compounds consisted of fat, multi-ring structures known to intercalate into DNA, which was considered a liability. We therefore focused on the pharmacophore 1 and other class of compounds.

Hit-to-Lead Selection Using Dystrophin Deficient Murine Muscle Cells

Figure 1B:
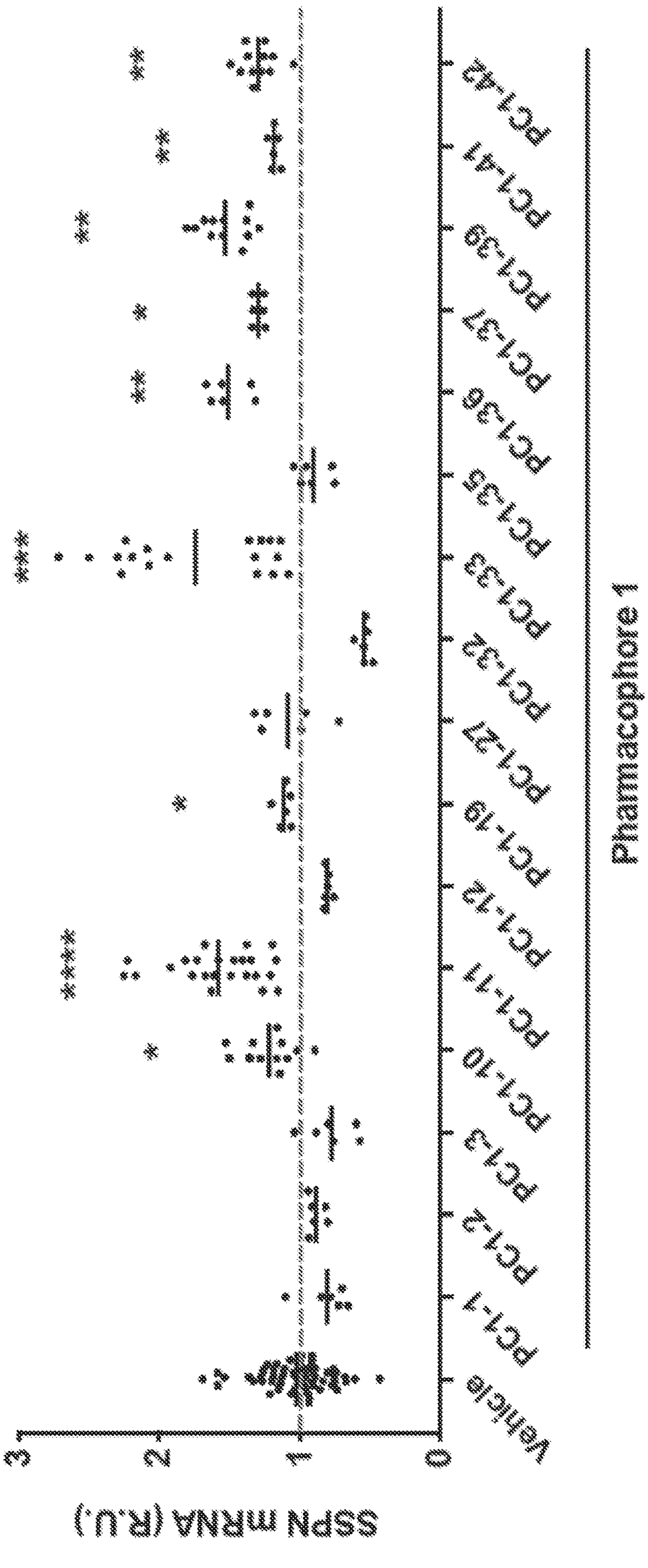
Figure 1C:
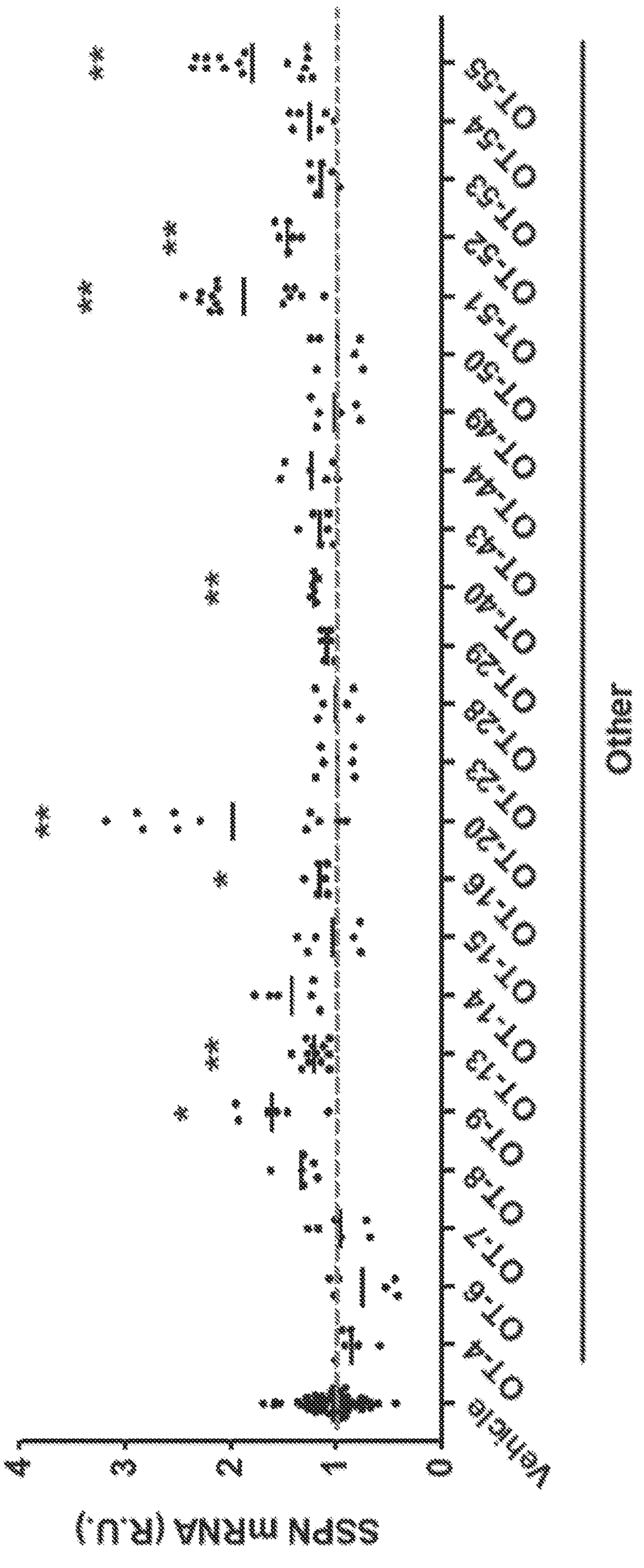

For the initial hit-to-lead selection, all commercially available confirmed hits were tested at a concentration of 5.5 μM in dystrophin-deficient mdx myotubes to determine if the compounds were active in a relevant disease model. Within the pharmacophore 1 group, nine of the sixteen hits increased SSPN gene expression between 1.1 to 1.8-fold relative to the vehicle control (FIG. 1*b*). With the other group, eight of the twenty-three other its increased SSPN gene expression between 1.2 to 2.0-fold (FIG. 1*c*). The initial hit-to-lead selection demonstrated that sequential screening with two separate reporter cell lines enables identification of compounds that increase SSPN mRNA levels in both wild-type and dystrophin-deficient murine muscle cells.

Figure 2:
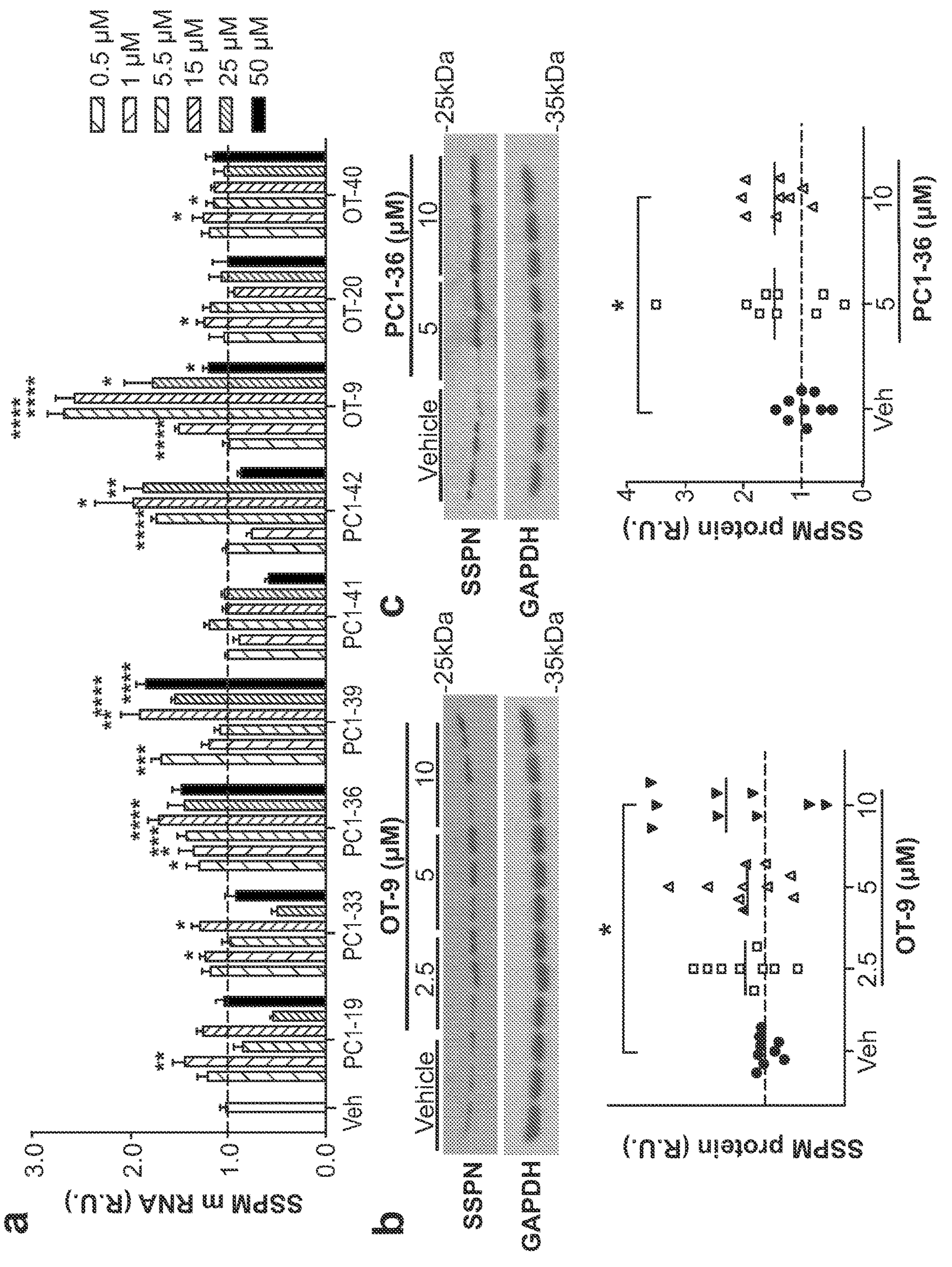
FIG. 2. Confirmed hits increase sarcospan gene and protein expression in mdx myotubes. (a) Relative sarcospan gene expression in dystrophin-deficient H2K mdx cells treated with 0.5 to 50 μM of pharmacophore 1 or other compounds for 48 hours. Gene expression was normalized to housekeeping gene β-Actin and vehicle-treated cells (0.2% DMSO). Data are represented as mean+SEM. n=3-6. (b-c) Sarcospan immunoblot of dystrophin-deficient H2K mdx cells treated with 2.5 to 10 μM of compounds for 48 hours. All cells were treated at day 2 of differentiation and harvested 48 hours post-treatment. Sarcospan protein levels were quantified in ImageJ and normalized to GAPDH and vehicle-treated cells (0.2% DMSO). Cell lysates were probed between 2-4 times in independent western blots. Representative blots shown. Quantification shown below immunoblots includes all experiments. Data represents individual replicates and mean value. n=3 per concentration. SSPN, sarcospan; R.U., relative units. *p<0.05, p<0.01, *p<0.001, ****p<0.0001.

After excluding compounds that were unstable in solution or that produced highly variable results, nine compounds remained. These nine compounds were tested at six different concentrations ranging from 0.5 to 50 μM in mdx myotubes to determine the activity across a broad range of concentrations. All the compounds except PC1-41 demonstrated activity with at least one concentration (FIG. 2*a*). PC1-36, PC1-42, and OT-9 induced a concentration-dependent response that peaked at 5.5 μM. To determine if the increase in SSPN RNA was also evident at the protein level, we treated mdx myotubes with 2.5 to 10 μM of OT-9, PC1-36, and PC1-42 and analyzed total protein lysates by immunoblotting with SSPN antibodies. We found that PC1-42 did not induce an increase in SSPN protein (data not shown). Compounds of the invention OT-9 and PC1-36 increased SSPN protein levels in the mdx myotubes by 1.5-fold, demonstrating that these compounds increased both SSPN gene and protein abundance in dystrophin-deficient muscle cells (FIG. 2*b-c*).

Figure 8:
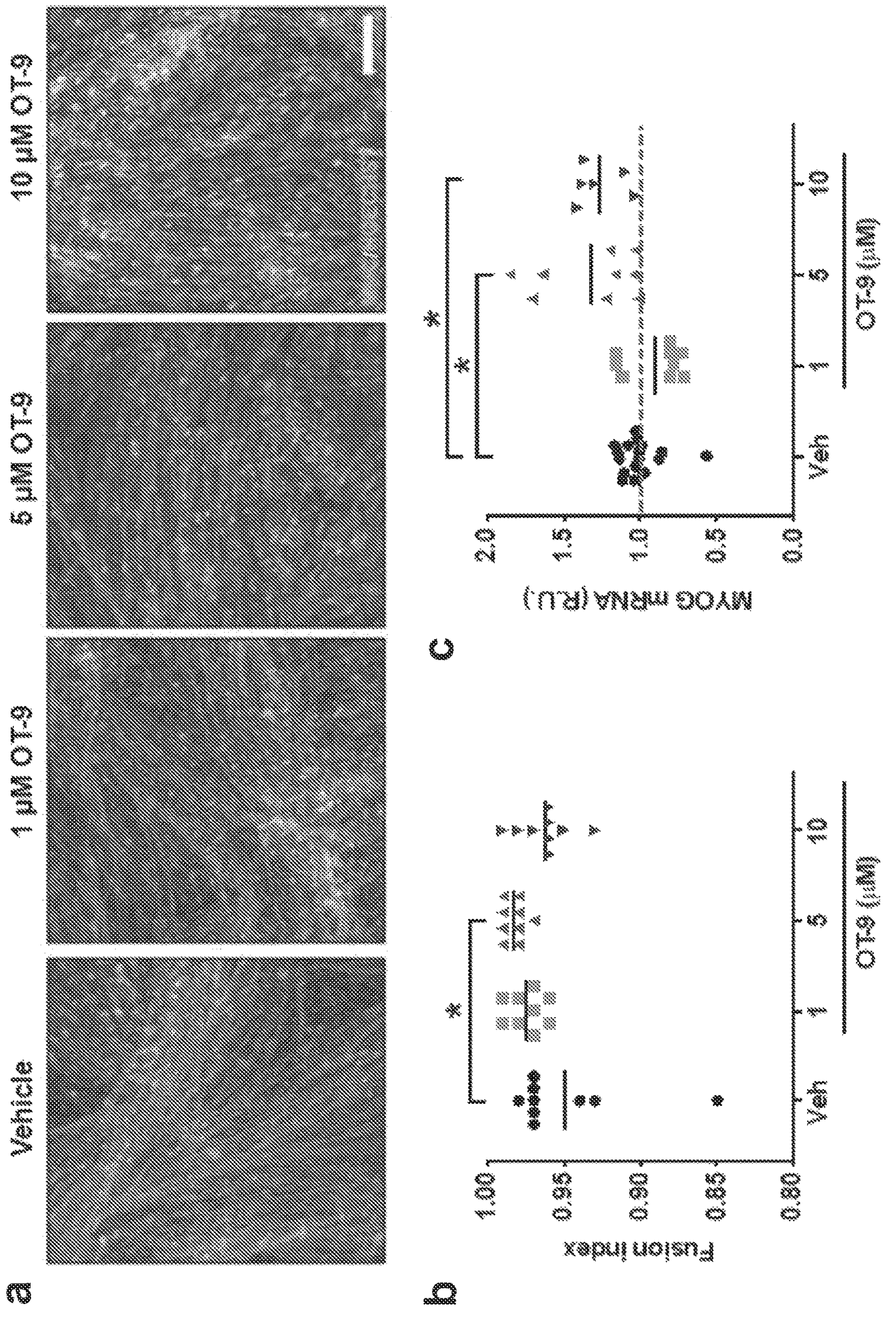
FIG. 8. OT-9 increases differentiation in mdx myotubes. mdx myotubes were treated with 1, 5, and 10 μM of OT-9 on day 2 and assayed on day 4 of differentiation. (a-b) OT-9 induces slight increase in H2K mdx myotube differentiation as measured by fusion index and (c) Myogenin gene expression. Data represents individual replicates and mean value. n=3. Scale bar=200 μm. MYOG, myogenin; R.U., relative units. *p<0.05, **p<0.01.

Previously, we profiled SSPN gene expression in differentiating myotubes and found that SSPN mRNA begins to increase on day three and reaches 10-fold increased levels on day five of differentiation, indicating that SSPN levels increase as cells differentiate [26]. To determine if the compound-induced increase in SSPN expression was due to enhanced differentiation, we treated mdx myotubes with OT-9 and assessed fusion index and expression of the myogenic transcription factor MYOG, markers of differentiation. OT-9 induced a slight increase in fusion index and MYOG gene expression in mdx myotubes, suggesting that the increase in SSPN may increase the rate of differentiation or that OT-9 may, in part, work through differentiation pathways (FIG. 8).

Figure 3:
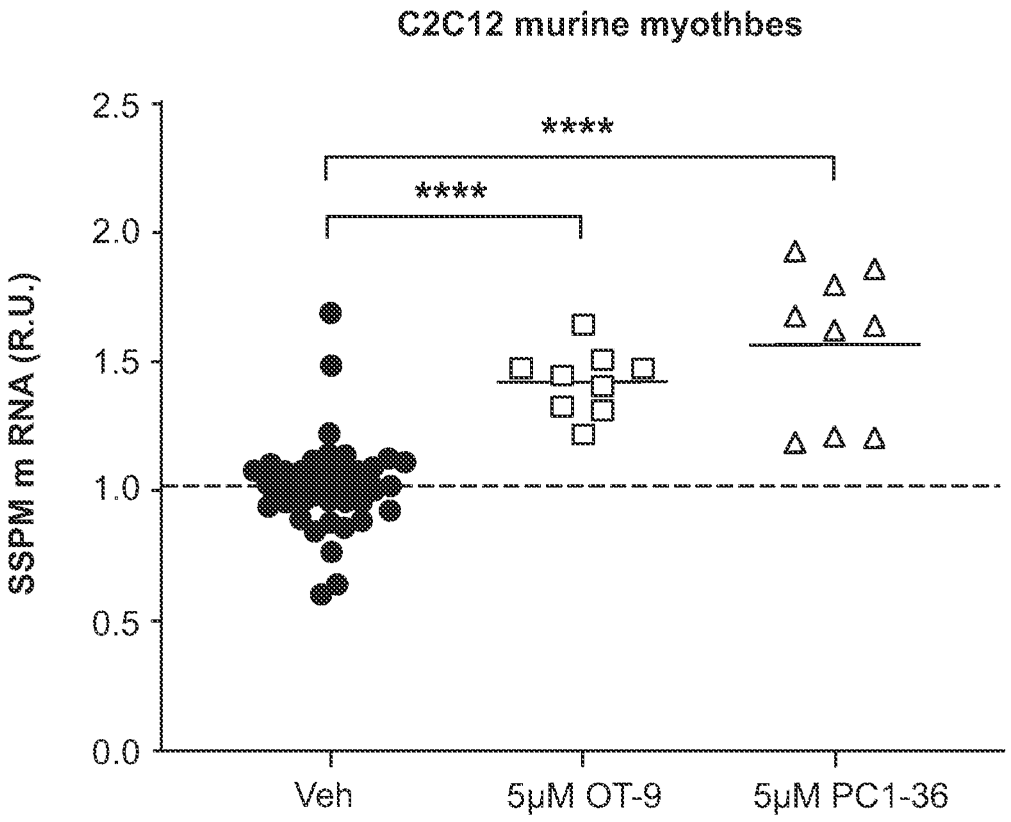
FIG. 3. OT-9 increases sarcospan gene expression in mouse WT myotubes. C2C12 myotubes treated for 48 hours with 5 μM of OT-9 and PC1-36 exhibit an increase in sarcospan gene expression. Gene expression was normalized to β-actin and vehicle-treated cells (0.1% DMSO). Data represents individual replicates and mean value. n=3-27. SSPN, sarcospan; R.U., relative units. ****p<0.0001.
Figure 9:
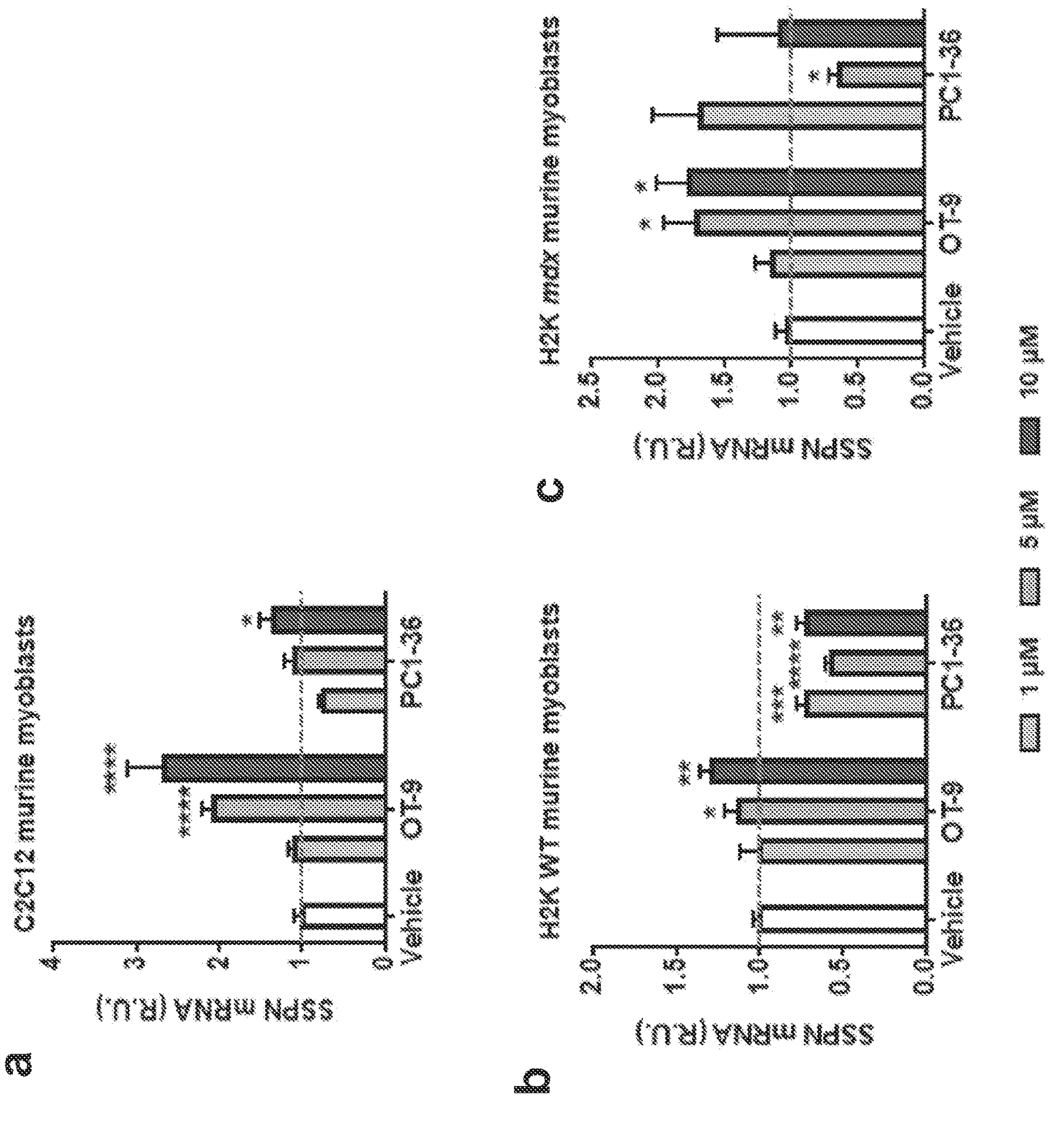
FIG. 9. OT-9 is effective in multiple myoblast lines. (a) C2C12, (b) EH2K WT, and (c) H2K mdx myoblasts are responsive to OT-9, but not PC1-36. Myoblasts were treated for 24 hours with 1, 5, and 10 μM of OT-9 or PC1-36. Gene expression was normalized to β-actin and vehicle-treated cells (0.1% DMSO). Data represents individual replicates and mean value. n=3-6. SSPN, sarcospan; R.U., relative units. *p<0.05, p<0.01, *p<0.001, ****p<0.0001.

To validate that the confirmed hits were not acting only in dystrophic cell lines in a cell line-specific manner, we tested OT-9 and PC1-36 in wild-type C2C12 myotubes. We found that both compounds increased SSPN mRNA levels in C2C12 myotubes. (FIG. 3). Treatment of C2C12, H2K WT, and H2K mdx murine myoblasts revealed that OT-9, but not PC1-36, increased SSPN mRNA levels in all myoblast lines. The unique ability of OT-9 to increase SSPN in myoblasts, suggests that OT-9 and PC1-36 may have different biological targets (FIG. 9).

Figure 10:
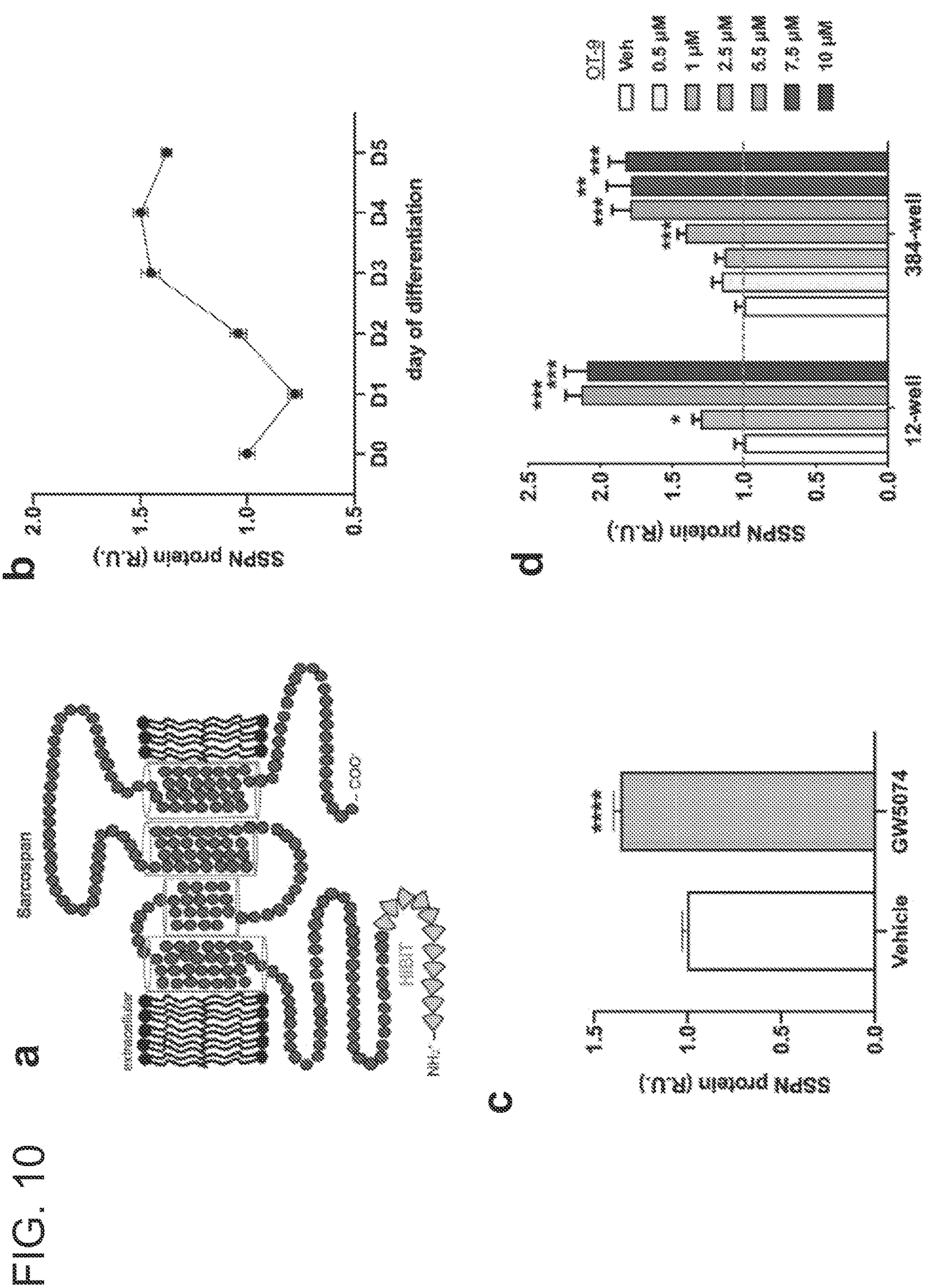
FIG. 10. Creation and validation of C2C12 SSPN-HiBiT protein reporter assay. 10(*a*) Schematic of the topology of sarcospan in the sarcolemma with the 11-amino acid HiBiT fused to the N-terminus of sarcospan. 10(*b*) SSPN-HiBiT protein levels increase with differentiation. 10(*c*) SSPN-HiBiT myotubes are responsive to positive control, GW5074, a c-raf inhibitor. Calculation of plate quality using GW5074 as a positive control using robust strictly standardized mean deviation (SSMD*) results in an SSMD* of 2.48, indicating it is an excellent moderate control. 10(*d*) The SSPN-HiBiT 12-well and 384-well format assays detect increases in reporter expression after treatment with OT-9. SSPN-HiBiT cells were treated on day 2 and harvested on day 4 of differentiation. R.U.=relative units normalized to vehicle control (DMSO), protein concentration for the 12-well assay, or nuclear count for the 384-well assay. Data shown represents the mean±SEM values. n=6. *p<0.05, p<0.01, *p<0.001, ****p<0.0001.

In order to effectively test new analogues, we created method for detecting SSPN protein in cells, e.g., SSPN-HiBiT. SSPN-HiBiT based on a murine C2C12 cell line expressing endogenous SSPN protein with an N-term fusion protein called the HiBiT, an 11 amino acid subunit of a luciferase enzyme (FIG. 10*a*). The SSPN-HiBiT protein is quantified through addition of substrate and a larger subunit of the luciferase enzyme to catalyze the formation of luminescent signal. The C2C12 SSPN-HiBiT cells express reporter protein at increasing levels throughout differentiation, which is supported by our previous finding t at SSPN mRNA increases with differentiation (FIG. 10*b*). We identified GW5074, a c-raf inhibitor, for use as a positive control for the assay. SSPN-HiBiT C2C12 myotubes treated with 5 μM of GW5074 show a 1.35-fold increase in SSPN-HiBiT levels (FIG. 10*c*). To validate the ability of the reporter to detect changes in SSPN protein levels after treatment with our lead compounds, we treated SSPN-HiBiT cells in both the 12-well and 384-well plate formats with 0.5-10 μM of OT-9. The assays detected dose-sensitive increases in SSPN (FIG. 10*d*). These results demonstrate that the SSPN-HiBiT C2C12 assays are useful tools in the SAR analysis of our lead compounds.

OT-9 Compound Increases Laminin-Binding Adhesion Complexes at the Cell Surface

Figure 4:
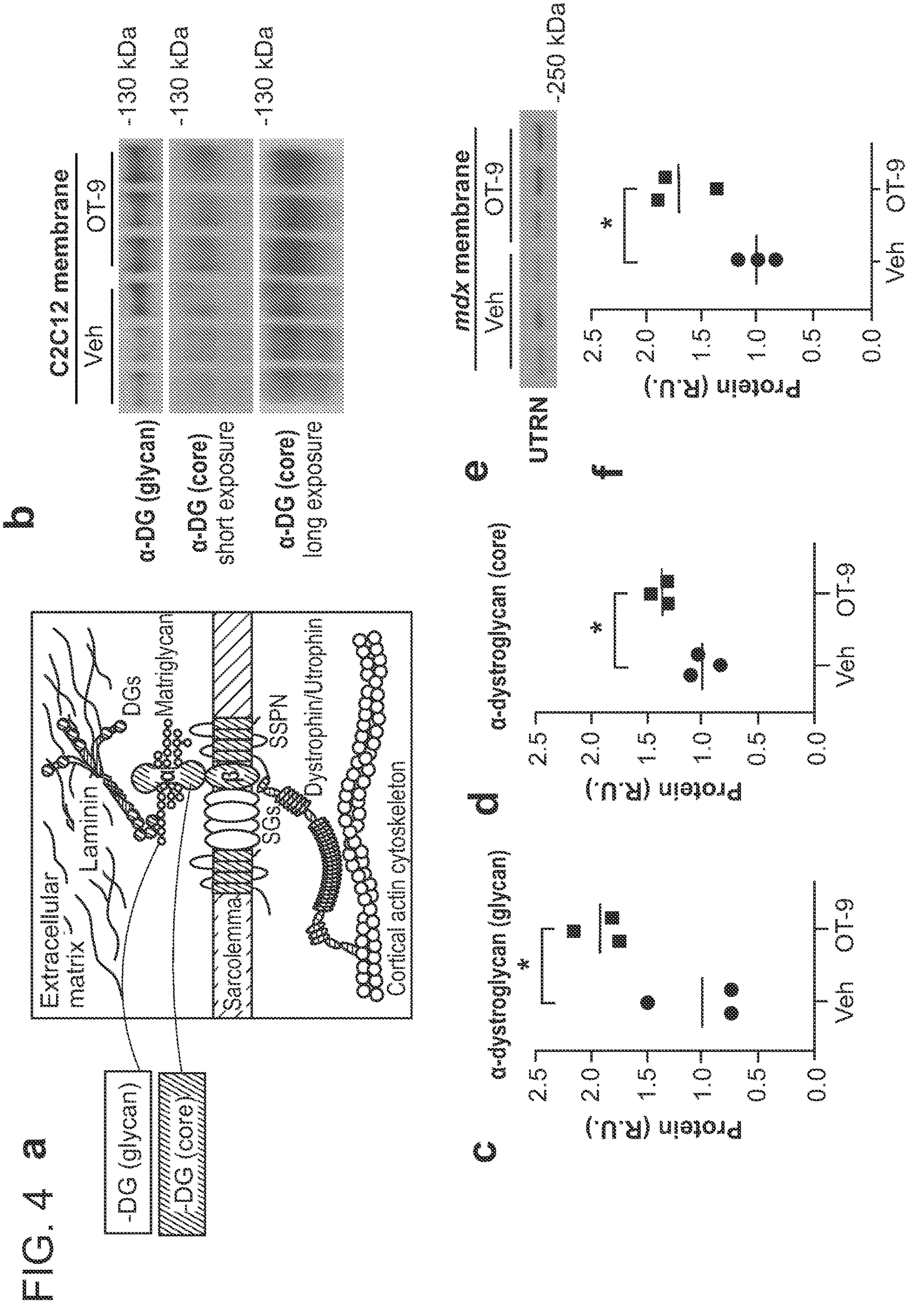
FIG. 4. OT-9 increases laminin-binding adhesion complexes at cell surface. C2C12 myotubes treated with vehicle or 5 μM of OT-9 for 48 hours were incubated in amine-reactive biotin to label cell surface proteins. Avidin was used to affinity purify the labelled proteins before immunoblot analysis with (a) antibodies recognizing the laminin-binding glycoepitope of alpha-dystroglycan (α-DG (glycan)) or core alpha-dystroglycan. (b) In cells treated with OT-9, both glycosylated alpha-dystroglycan and core alpha-dystroglycan were increased at the cell surface. (c-d) Quantification of immunoblots. (e) mdx myotubes treated with vehicle or 5 μM of OT-9 for 48 hours were incubated in biotin to label cell surface proteins and affinity purified with avidin. Immunoblot analysis shows upregulation of utrophin associated with big tin-labelled cell surface proteins. (f) Quantification of utrophin immunoblot. Data represents individual replicates and mean value. n=3. α-DG, alpha-dystroglycan; UTRN, utrophin; R.U., relative units. *p<0.05.
Figure 11:
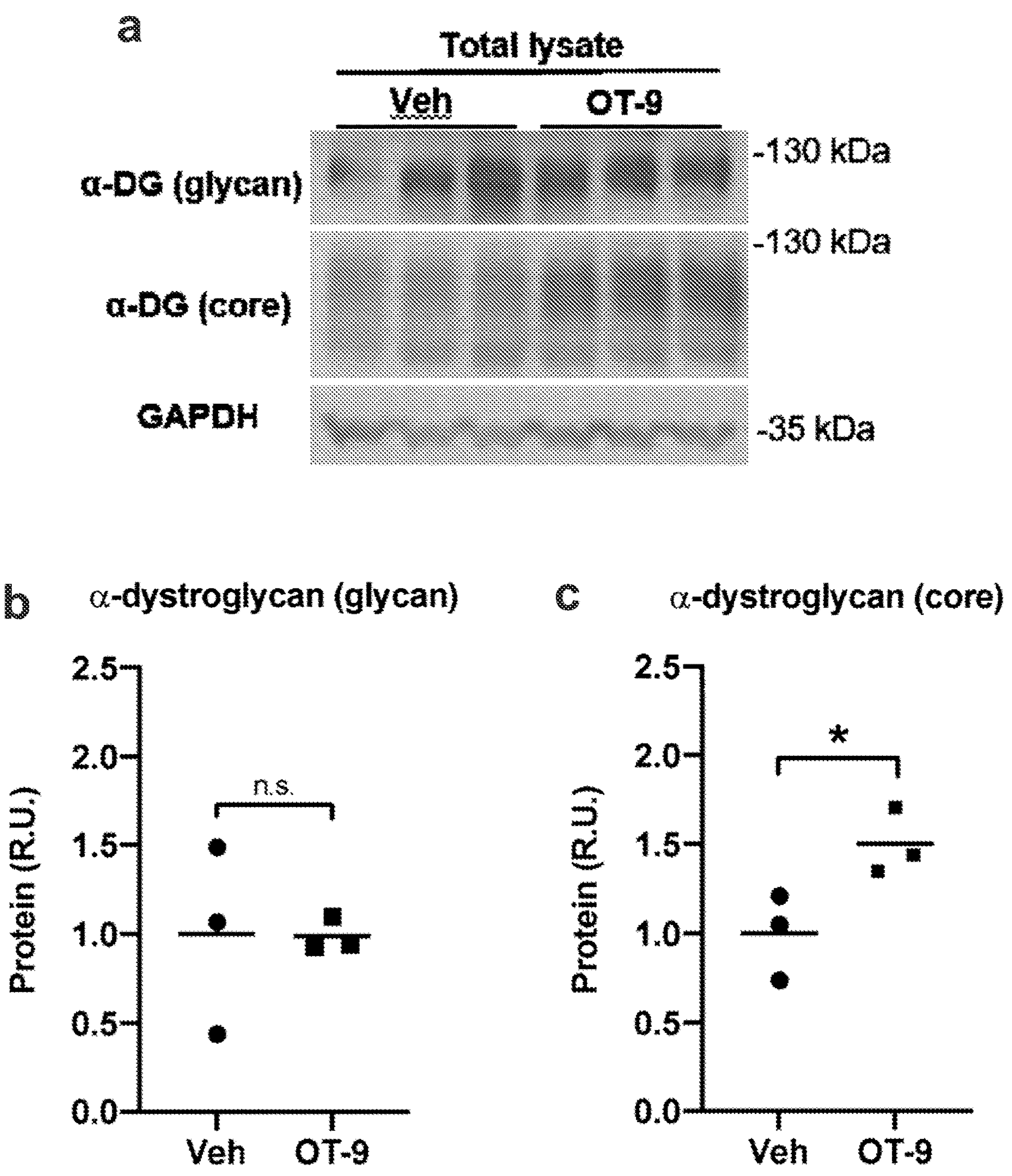
FIG. 11. OT-9 increases laminin-binding adhesion proteins in total lysate. C2C12 myotubes treated with vehicle or 5 μM of OT-9 for 48 hours before immunoblot analysis. (a) Cells treated with OT-9 did not exhibit an increase in the fully glycosylated, laminin binding alpha-dystroglycan (α-DG (glycan)), but did exhibit an increase in core alpha-dystroglycan. GAPDH is shown as a loading control. (b-c) Quantification of immunoblots. Data represents individual replicates and mean value. n=3. R.U., relative units normalized to GAPDH and vehicle control.

In striated muscle, SSPN is a scaffold for the three major laminin-binding adhesion complexes that connect the cell membrane (sarcolemma) to the extracellular matrix: the DGC, UGC, and α7β1D-integrin. Overexpression of SSPN in mdx muscle increases the localization of the UGC and α7β1D-integrin complex. To determine if the OT-9-affects SSPN localization at the cell membrane in myotubes, we labeled cell surface proteins with an amine-reactive biotin. C2C12 myotubes treated with OT-9 were incubated in cell impermeable biotin, lysed to solubilize proteins, affinity purified with avidin, and eluted with LSB to obtain cell surface proteins. Using antibodies that recognize the laminin-binding glycoepitope of α-DG (glycan) and the core α-DG protein (FIG. 4*a*), we performed immunoblot analysis of the biotinylated cell surface proteins and total lysate. OT-9 increased glycosylated α-DG by 1.8-fold and core α-DG by 1.6-fold at the cell surface (FIG. 4*b-d*). Immunoblot analysis of total protein lysates revealed that OT-9 did not increase levels of glycosylated α-DG, but did increase core α-DG by 1.5-fold (FIG. 11). The difference in cell surface and total lysate levels of glycosylated α-DG suggests that OT-9 increased membrane localization of the laminin-binding α-DG.

In mdx mice overexpressing SSPN, the dystrophin paralogue utrophin is upregulated at the sarcolemma and contributes to the increase in membrane to ECM adhesion. Using the same biotinylation experimental approach, we assessed whether OT-9 affected utrophin expression at the cell surface membrane. While utrophin is intracellular and therefore not directly biotinylated, the solubilization buffer contained a gentle detergent that preserved interactions within adhesion complexes, including that of utrophin, β-dystroglycan, and the cell surface α-DG. mdx myotubes treated with OT-9 exhibited a 1.6-fold increase in membrane-associated utrophin protein (FIG. 4*e-f*). Taken together, our findings demonstrate that OT-9 increased the sarcolemmal localization of both α-DG and utrophin, suggesting an upregulation of the laminin-binding utrophin glycoprotein complex.

Figure 5:
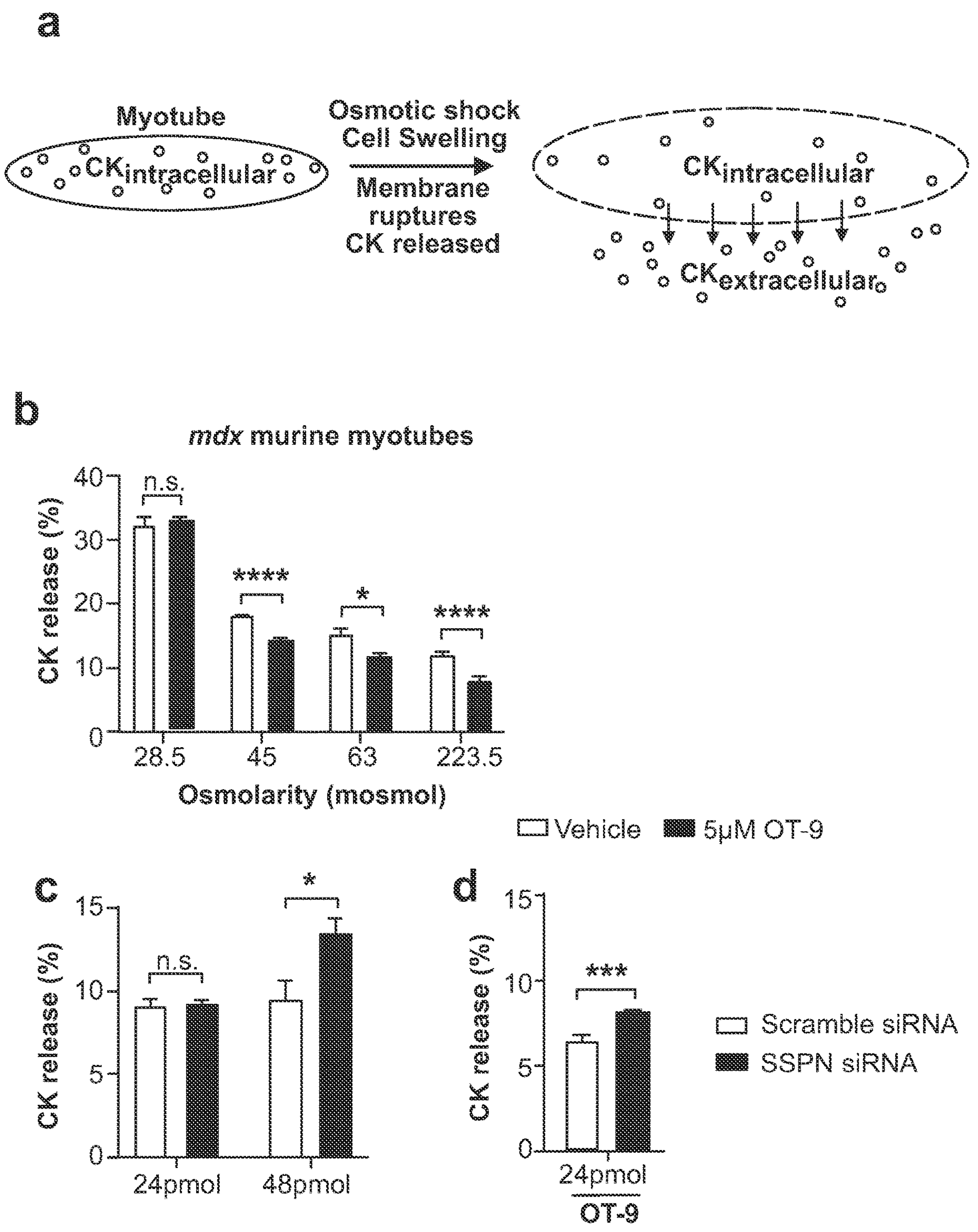
FIG. 5. OT-9 improves membrane stability of dystrophin-deficient myotubes in part through upregulation of sarcospan. (a) The creatine kinase (CK) release assay entails subjecting myotubes to osmotic shock, which causes cell swelling and membrane damage, allowing for intracellular CK to be released from the cell into the surrounding medium. CK release is calculated by taking the ratio of $CK_{extracellular}/(CK_{extracellular}+CK_{intracelluar})$. Day 2 (b) mdx treated were treated for 48 hours with 5 μM of OT-9 and subjected to osmotic shock with solutions ranging from 28.5-224.5 milliosmoles (mosmol). (c) mdx myotubes were transfected with 24 or 48 nM of scramble siRNA or siRNA targeting sarcospan. After 48 hours, myotubes were subjected to osmotic shock with 45 mosmol solutions. The 24 nM SSPN siRNA transfection did not affect CK release relative to scramble control. The 48 nM concentration of sarcospan siRNA increased CK release relative to the scramble control, indicating sarcospan contributes to membrane stability regardless of treatment (d) mdx myotubes treated in parallel with 24 nM of sarcospan siRNA and 10 μM of OT-9 demonstrate that depletion of sarcospan reduced the ability of OT-9 to improve membrane stability. Data represents mean+SEM. n=3. SSPN, sarcospan; R.U., relative units. *p<0.05, p<0.01, *p<0.001, ****p<0.0001.

OT-9 Improves Membrane Stability in Dystrophin-Deficient Myotubes Through Upregulation of Sarcospan To determine if the increase in utrophin and dystroglycan at the cell membrane resulted in a functional improvement in membrane stability, we used a modified protocol for an in vitro creatine kinase (CK) release assay [32]. The assay entails subjecting myotubes to osmotic shock, which causes cell swelling and membrane damage, allowing for intracellular CK to be released from the cell into the surrounding medium (FIG. 5*a*). To determine the optimal conditions for osmotic shock that result in a detectable change in CK release, we treated mdx with vehicle or 5 μM of OT-9 for 48 hours then induced osmotic shock using solutions ranging from 28.5 to 223.5 milliosmoles (mosmol), with 223.5 mosmol being closest to physiological osmolarity (280 mosmol). mdx myotubes exhibited higher CK release with lower, more damaging osmolarity concentrations (FIG. 5*b*). Osmotic shock with the 28.5 mosmol solution resulted in a 30-40% CK release, while the 45 and 63 mosmol solution caused a 10-15% CK release, indicating relatively less membrane damage. In cells subjected to osmotic shock with 45, 63, and 223.5 mosmol solutions, OT-9 significantly reduced CK release, suggesting that OT-9 stabilized the membrane and protected it from osmotic shock-induced damage. Treatment with OT-9 did not reduce CK release in cells subjected to osmotic shock with 28.5 mosmol solutions, indicating that OT-9 was not able to stabilize the membrane likely due to severe membrane damage caused by the extremely low osmolarity.

Figure 12:
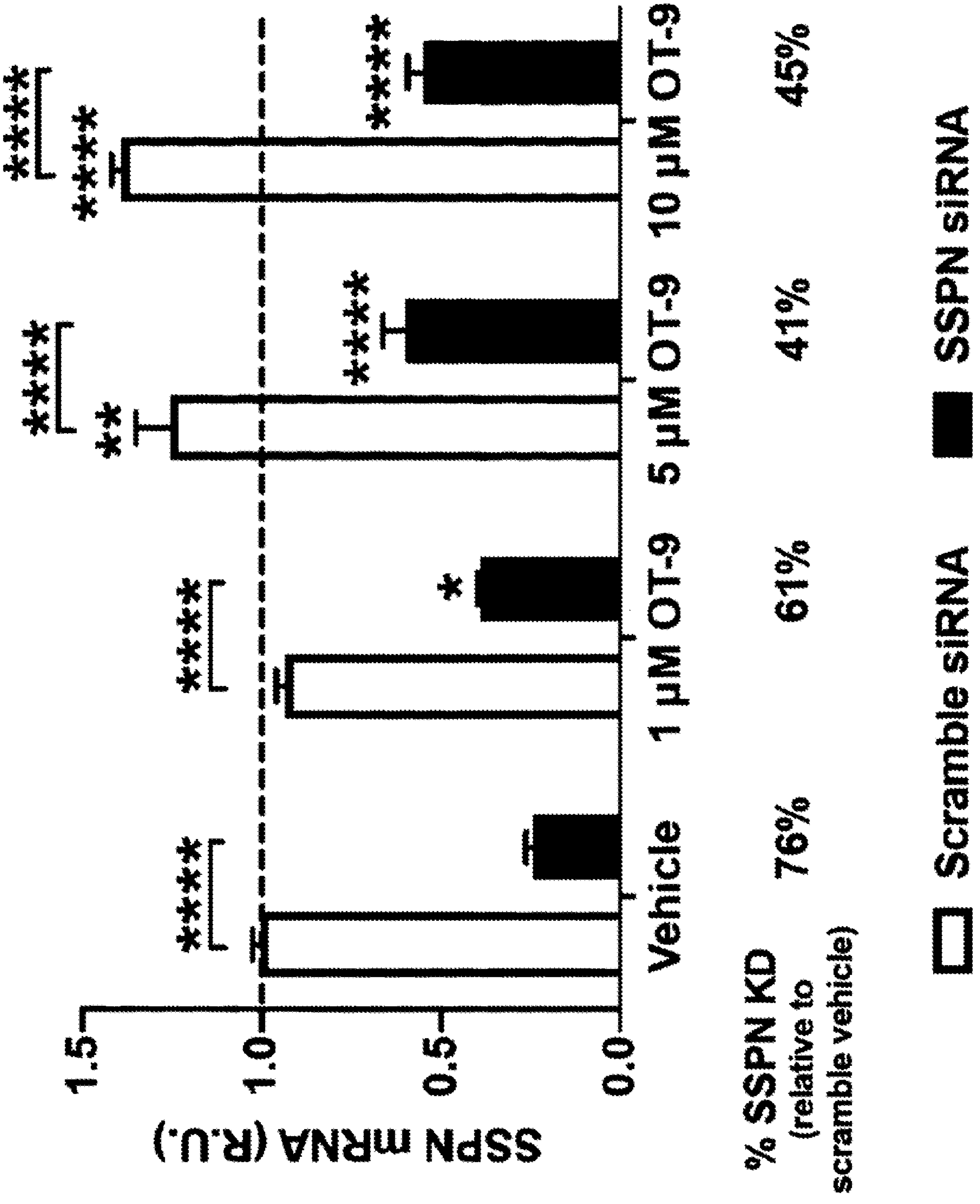
FIG. 12. siRNA-mediated knock down of SSPN results in a 76% knock down efficiency. mdx myotubes were treated in parallel with 1, 5, and 10 μM of OT-9 and 24 nM scramble control siRNA or siRNA targeting SSPN mRNA. Gene expression was normalized to β-actin and vehicle and scramble siRNA treated cells. Data represents mean+SEM. n=3. SSPN, sarcospan; R.U., relative units. *p<0.05, p<0.01, **p<0.0001.

To determine if the membrane stabilizing effect induced by OT-9 was dependent on SSPN, we performed siRNA-mediated knockdown of SSPN in parallel with compound treatment. To assess knockdown efficiency, we first treated mdx myotubes with 1, 5, or 10 μM of OT-9 and 24 nM of scramble siRNA or siRNA targeting SSPN mRNA (SSPN siRNA). In cells treated with vehicle control, SSPN siRNA reduced SSPN mRNA by 76% relative to the scramble control (FIG. 12). In cells treated with scramble siRNA and OT-9, SSPN mRNA increased by up to 1.4-fold relative to the vehicle control. In cells treated with SSPN siRNA and OT-9, SSPN levels were reduced relative to their respective scramble siRNA controls. However, even with SSPN siRNA, OT-9 increased SSPN mRNA levels due to the incomplete knockdown, leading us to use a higher siRNA concentration in subsequent experiments.

To assess the effect of SSPN knockdown on membrane stability in the absence of any compound treatment, we transfected mdx myotubes with 24 and 48 nM of scramble and SSPN siRNA and subjected the cells to osmotic shock with 45 mosmol solutions. In cells transfected with 24 nM of siRNA, knockdown of SSPN did not affect CK release (FIG. 5*c*). However, in cells transfected with 48 nM of siRNA, knockdown of SSPN increased K release from 9% to 13%, indicating that loss of SSPN itself renders the sarcolemma more susceptible to membrane damage. To prevent confounding the data with changes in baseline CK release induced by SSPN knockdown, we selected the 24 nM siRNA concentration for following studies because it did not affect baseline CK release. We treated mdx myotubes with 10 μM of OT-9 in parallel with 24 nM of scramble or SSPN siRNA for 48 hours prior to osmotic shock and discovered that depletion of SSPN increased the CK release from 6.5% to 8% (FIG. 5*d*). The results revealed that knockdown of SSPN reduced the ability of OT-9 to stabilize the sarcolemma, indicating that SSPN expression is required for the full membrane stabilizing effect of OT-9.

OT-9 and OT-9m Increase SSPN Gene Expression in Mdx Mice

Figure 6:
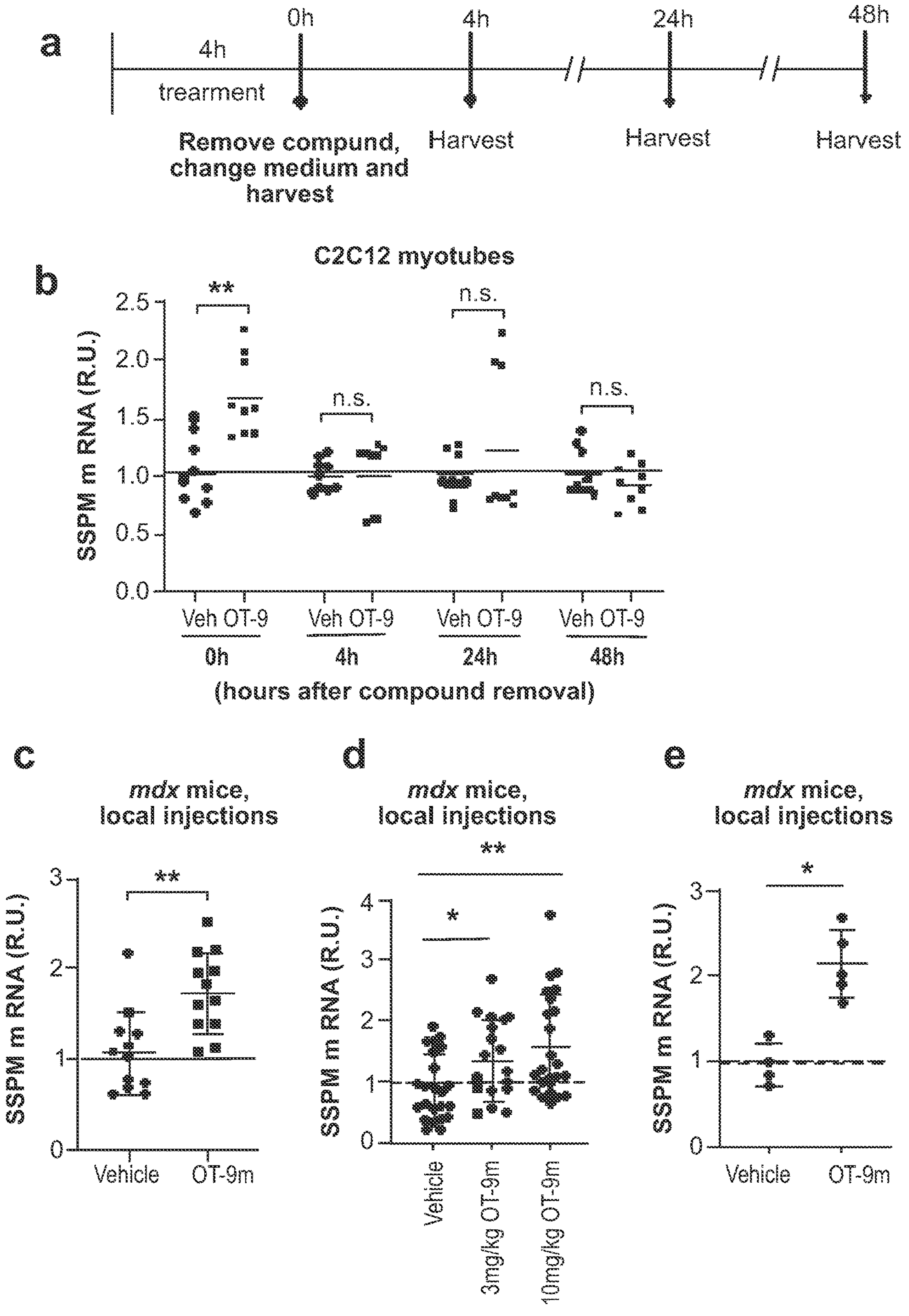
FIG. 6. OT-9 and OT-9m increase sarcospan mRNA in vitro and in vivo in mdx muscle. (a) Schematic overview of experimental setup to test sarcospan mRNA stability in vitro. C2C12 myotubes were treated on the second day of differentiation with 5 μM of OT-9. After 4 hours, the medium containing OT-9 was removed and changed to fresh medium without compound. The cells were harvested for gene expression analysis immediately after medium change (0 h), and 4 h, 24 h, and 48 h after. (b) OT-9 induced sarcospan gene expression after 4 hours of treatment (0 h). After extended removal of the compound (4-48 h), sarcospan mRNA levels were the same in cells treated with vehicle and OT-9. (c) 20-week old male mdx littermates were injected in both tibialis anterior muscles with vehicle (5% DMSO, 95% PBS) or 3 mg/kg g of OT-9. After 4 hours, the muscles were harvested and processed for gene expression analysis. (d) 19-22-week old mdx males were injected in both tibialis anterior muscles with vehicle (5% DMSO, 95% PBS) or 3 mg/kg and 10 mg/kg of OT-9m. After 4 hours, the muscles were harvested and processed for gene expression analysis. (e) 13-week old mdx males were injected subcutaneously with vehicle (4% PEG-200 in hydroxypropyl-b-cyclodextrin) or 20 mg/kg/day of OT-9m. After 13 days of treatment, the muscles were harvested and processed for gene expression analysis. Gene expression was normalized to β-actin and vehicle-treated cells. Data represents individual replicates and mean value. n=3 for in vitro and n=2 for in vivo study. SSPN, sarcospan; R.U., relative units. **p<0.01.

After demonstrating the ability of OT-9 to increase SSPN protein and laminin-binding adhesion complexes at the membrane, which in turn led to improved membrane stability in dystrophin-deficient myotubes, we next interrogated the capacity of OT-9 to increase SSPN gene expression in vivo. Estimation of OT-9 stability revealed a large difference in half-life of the compound in mouse plasma (7.7 hours) versus PBS (49 mins) (FIGS. 13 & 14). Because cell culture medium is distinct from both solutions, we quantified SSPN mRNA stability in C2C12 myotubes treated with 5 μM of OT-9 for 4 hours to determine if short-term treatment could induce SSPN expression. After 4 hours of treatment with OT-9, medium containing the compound was removed and changed to fresh medium. The cells were harvested at 0, 4, 24, and 48 hours after compound removal (FIG. 6*a*). Immediately after compound removal (0 h), SSPN mRNA levels were elevated by 1.5-fold over the vehicle control, demonstrating that OT-9 induces SSPN gene expression after just 4 hours of treatment (FIG. 6*b*). However, 4, 24, and 48 hours after compound removal, SSPN mRNA levels returned to baseline levels, which suggested that SSPN mRNA was upregulated for up to 4 hours after induction by OT-9.

To evaluate the in vivo safety and activity of OT-9, we performed two pilot studies in wild-type C57/Bl6 and mdx mice. For the preliminary safety assessment of OT-9, we performed IP injections in 6-month old C57/Bl6 males. The mice were injected with vehicle, 30 mg/kg of OT-9, or 50 mg/kg of OT-9 (n=1). No signs of inflammation, necrosis or compound accumulation were observed at the injection site. The liver, kidneys, pancreas, and intestine appeared to be of normal weight and size. As some insoluble particles were observed in 50 mg/kg solution of OT-9, the 30 mg/kg concentration was chosen for assessment of in vivo activity.

After the preliminary safety evaluation, we tested the ability of OT-9 to increase SSPN gene expression in vivo. We chose to assess activity after 4 hours of treatment based on the finding presented in FIG. 8*b*, which demonstrated that 4 hours of treatment with OT-9 was sufficient to significantly increase SSPN mRNA levels in vitro. Five 20-weeks old male mdx littermates were subjected to intramuscular injections in both tibialis anterior (TA) muscles. Two mice were injected in both TAs with vehicle and two mice were injected with 3 mg/kg of OT-9 (molar equivalent of 9.4 mM used in the safety assessment). After 4 hours of treatment, the TAs were harvested and processed for gene expression analysis. No adverse effects were observed after local OT-9 injections in the mice. OT-9 induced a 1.7-fold increase in SSPN gene expression relative to the vehicle control-treated group, demonstrating that OT-9 is capable of increasing SSPN gene expression in mdx mice (FIG. 6*c*). After determination that OT-9 is capable of increasing SSPN gene expression in vivo, we evaluated one of its derivatives, OT-9m, for its ability to increase SSPN expression in mdx mice. OT-9m was chosen based on its improved activity in vitro compared to OT-9 (compare, Table 1, entries 1 & 14). To assess activity OT-9m in vivo after local administration, eleven 19-22 weeks old male mdx mice were subjected t intramuscular injections in both tibialis anterior (TA) muscles. Four mice were injected in both TAs with vehicle, three mice were injected with 3 mg/kg of OT-9m and four mice were injected with 10 mg/kg of OT-9m. After 4 hours of treatment, the TAs were harvested and processed for gene expression analysis. No adverse effects were observed after local OT-9m injections in the mice. Similar to OT-9, intramuscular injections with OT-9m in mdx mice demonstrated that OT-9m at 3 mg/kg and 10 mg/kg dose increased SSPN gene expression in as little as 4 hours (FIG. 6*d*).

Followed by local administration, we evaluated ability of OT-9m to enhance SSPN expression in mdx mice after systemic treatment. 13-weeks old mdx males were injected subcutaneously with vehicle (4% PEG-200 in hydroxypropyl-b-cyclodextrin) or 20 mg/kg daily of OT-9m. After 13 days of treatment, the quadriceps, TAs, and heart muscles were harvested and quadriceps processed for gene expression analysis. Systemic treatment by OT-9m lead to 2-fold increase of SSPN transcript (FIG. 6*e*). We previously investigated the levels of sarcospan necessary to rescue disease pathology in mdx mice through the availability of mouse lines expressing various levels of sarcospan. We determined that mice overexpressing sarcospan by 1.5-fold were not rescued, while mice overexpressing sarcospan by 3-fold were rescued. This demonstrated that the level of sarcospan overexpression needed to rescue mdx mice is somewhere between 1.5 to 3-fold. Treatment of mdx mice with OT-9 and OT-9m demonstrated that both compounds are capable of increasing SSPN gene expression in mdx mice at the levels which are close to the desired 1.5 to 3-fold increase.

Example 1: Preparation of Exemplary Compounds

Synthetic Scheme A

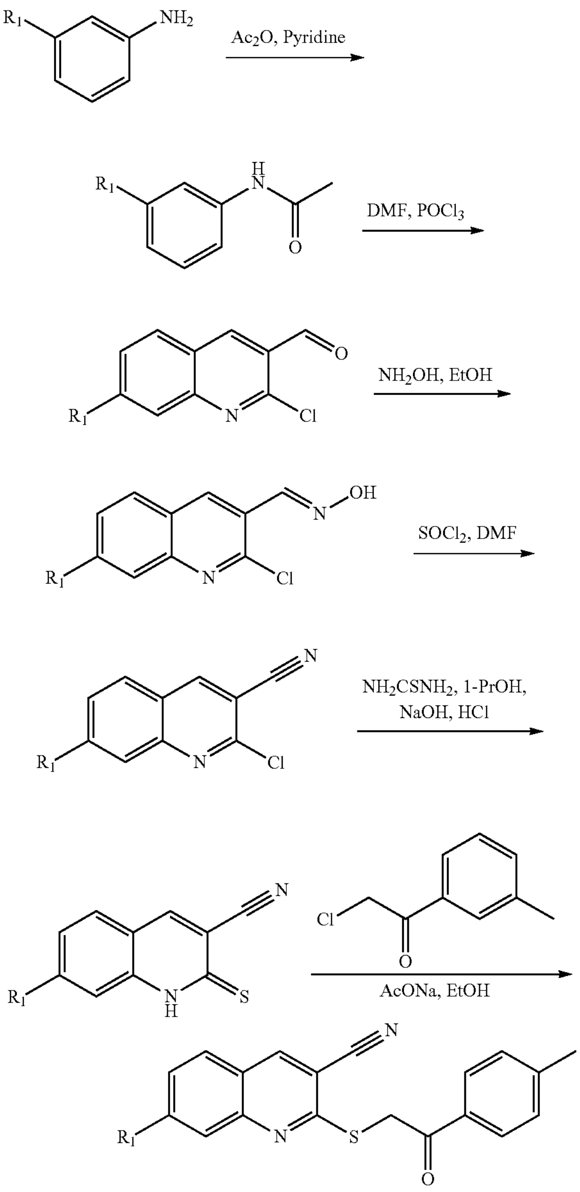

Synthetic Scheme B

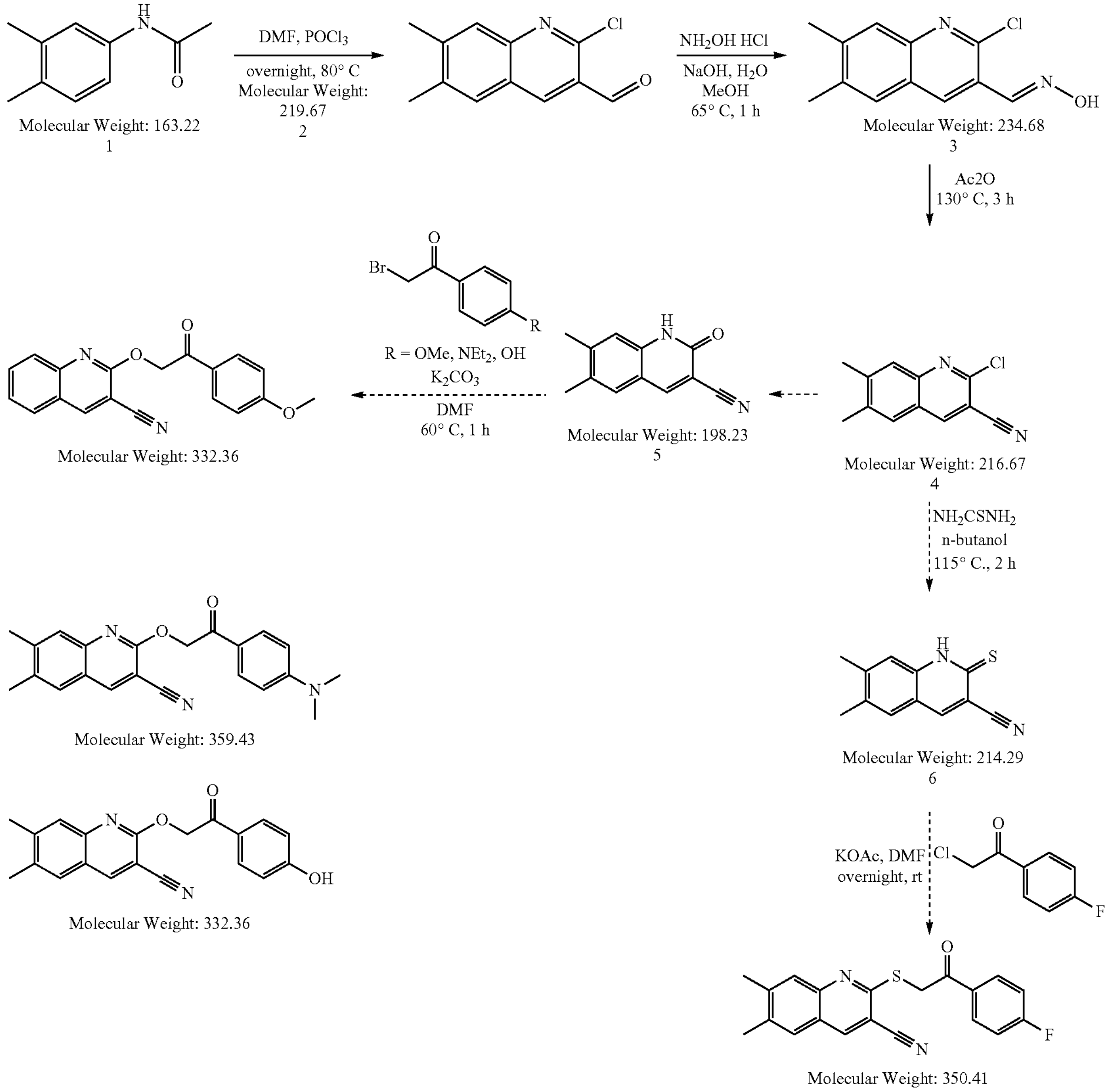

1.1 2-chloro-6,7-dimethylquinoline-3-carbaldehyde. Step 1. $POCl_3$ (13.7 mL, 147 mmol, 6 eq) was added dropwise to DMF (5.7 mL, 73.5 mmol, 3 eq) at 0° C. and allowed to stir at rt for 30 minutes. Then, N-(3,4-dimethylphenyl)acetamide (4 g, 24.5 mmol, 1.0 eq) was added at rt and the reaction was then heated to 80° C. and allowed to stir for 16 h. After completion, the mixture was allowed to cool to rt and then poured in cold water. The aqueous layer was then extracted with EtOAc and the organic layer was washed with brine, filtered, dried over sodium sulfate, and then concentrated. The crude product was then purified using column chromatography (2% EtOAc:Chloroform) to yield pure product as a white solid (2.85 g, 52%).

1.2 (E)-2-chloro-6,7-dimethylquinoline-3-carbaldehyde oxime. Step 2. To a solution of hydroxylamine hydrochloride (609 mg, 8.77 mmol, 1.2 eq) and methanol (15 mL) at 0° C. was added sodium hydroxide solution (409 mg, 10.23 mmol, 1.4 eq in 5.37 mL of water) followed by portion wise addition of Compound 2 (1.605 g, 7.31 mmol, 1 eq) over period of 10 minutes. The reaction mixture was allowed to reflux at 65° C. for 1 h. When starting material consumption confirmed by TLC, the reaction mixture was allowed to cool to rt, filter d, and washed with ice cold water and hexanes. Hexane layer was evaporated under vacuum to afford desired product as an off-white solid (1.6 g, 94%). Remaining 1.2 g of starting material pushed forward through conditions to yield product (1.19 g, 94%).

1.3 2-chloro-6,7-dimethylquinoline-3-carbonitrile. Step 3. Compound 3 in acetic anhydride (17 mL) was allowed to reflux at 130° C. for 3 h. Once reaction completion confirmed by TLC (10% EtOAc:Hexanes), mixture allowed to cool to rt and excess solvent evaporated. Remaining solid stirred in EtOAc for 1 h, then solid filtered and washed with EtOAc (2×20 mL). The solid was then purified using column chromatography (0-100% DCM:Hexanes) to yield pure product as a white solid. The filtrate was also washed with 40 mL ice cold water dried over sodium sulfate, and evaporated to get crude material. This material was then purified by column chromatography (0-100% DCM:Hexanes) to yield pure product as a white solid. The two solids were washed with cold water and brine. The organic layer was then filtered, dried over sodium sulfate, and concentrated. The crude material was then purified by column chromatography (40% EtOAc:Hexanes) and prep-HPLC to yield pure product.

| Molecular | Bromide | Yield | $[M + H]^+$ | Annotated H NMR |
|---|---|---|---|---|
| 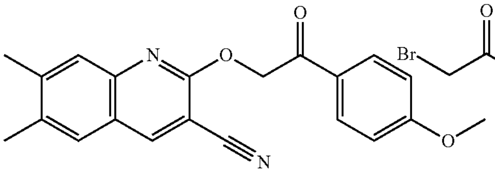 | 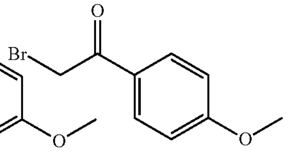 | 12.3 mg, 14% | 347.4 | 1H NMR (300 MHz, CHLOROFORM-d) δ ppm 8.31 (s, 1 H) 7.96-8.04 (m, 2 H) 7.46 (s, 2 H) 6.96-7.01 (m, 2 H) 5.75 (s, 2 H) 3.89 (s, 3 H) 2.38 (s, 6 H) |
| 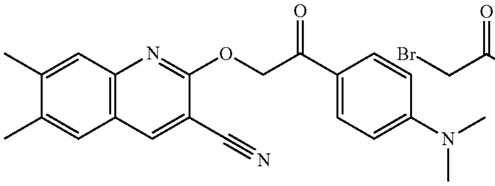 | 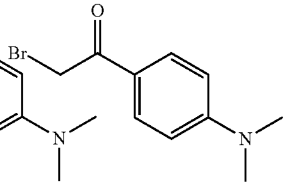 | 4.6 mg, 3% | 360.4 | 1H NMR (400 MHz, ACETONITRILE-d3) δ ppm 8.43 (s, 1 H) 8.00 (d, J = 9.00 Hz, 2H) 7.53 (s, 1 H) 7.08 (s, 1 H) 6.83 (d, J = 9.26 Hz, 2 H) 3.11 (s, 7 H) 2.35 (s, 3 H) 2.34 (s, 3 H) |

combined (461 mg, 31%). Additional 1.19 g of Compound 3 was pushed forward through the reaction to yield product as a white solid (620 mg, 56%).

1.4 6,7-dimethyl-2-oxo-1,2-dihydroquinoline-3-carbonitrile. Step 4. mixture of Compound 4 (274 mg, 1.27 mmol, 1 eq) and concentrated hydrochloric acid (25.4 L) in methanol (12.6 mL) was refluxed for 4 h. After completion of reaction, the mixture was allowed to cool to rt and product crashed out of the mixture. The product was filtered and washed with acetone (2×20 mL) to yield product as an off-white solid (100 mg, 40%). Additional 620 mg of Compound 4 pushed through the reaction to yield product as a fluffy off-white solid (267 mg, 47%).

1.5 Procedure to access 2-(2-(4-methoxyphenyl)-2-oxoethoxy)-7-met ylquinoline-3-carbonitrile. Step 5. To a solution of Compound 5 (50 mg, 0.25 mmol 1.0 eq) in DMF (0.5 mL) was added anhydrous potassium carbonate (52.3 mg, 0.375 mmol, 0.5 eq) followed by ketone (58 mg, 0.25 mmol, 1.0 eq). The resulting mixture was then stirred at 60° C. overnight. After reaction completion confirmed by TLC (5% MeOH:DCM), the reaction mixture was cooled to rt and diluted with water. The aqueous layer was then extracted with ethyl acetate. The organic layer was then washed with cold water and brine. The organic layer was then filtered, dried over sodium sulfate, and concentrated. The crude material was then purified by column chromatography (40% EtOAc:Hexanes) to yield pure product.

1.6 Procedure to access 2-(2-(4-(dimethylamino)phenyl)-2-oxoethoxy)-6,7-dimethylquinoline-3-carbonitrile. Step 5. To a solution of Compound 5 (75 mg, 0.38 mmol, 1.0 eq) in DMF (0.5 mL) was added anhydrous potassium carbonate (78.4 mg, 0.568 mmol, 1.5 eq) followed by ketone (91.6 mg, 0.38 mmol, 1.0 eq). The resulting mixture was then stirred at 60° C. overnight. After reaction completion confirmed by TLC (5% MeOH:DCM), the reaction mixture was cooled to rt and diluted with water. The aqueous layer was then extracted with ethyl acetate. The organic layer was then 1.7 Procedure to access 2-((2-(4-fluorophenyl)-2-oxoethyl)thio)-6,7-dimethylquinoline-3-carbonitrile. Step 5. Compound 5 (169 mg, 0.79 mmol, 1.0 eq) was dissolved in anhydrous DMF (6.76 mL) at 60° C. and then allowed to cool to rt. Then, potassium acetate (155 mg, 1.58 mmol, 2.0 eq) and 2-bromo-1-(4-fluorophenyl)ethan-1-one (342 mg, 1.58 mmol, 2.0 eq) were added and the reaction was allowed to stir at rt overnight. After complet on of the reaction was confirmed by TLC (100% DCM), 20 mL of water was added to the reaction. The pale yellow solid that crashed out was then filtered. The solid was then redissolved in DCM:MeOH (10%) and dried over anhydrous sodium sulfate. The solid was then dissolved in 40 mL of DCM:MeOH (5%) and ran through a plug using DCM to yield product as a pale yellow solid (185 mg, 69%). [M+H]+=351.4. 1H NMR (300 MHz, CHLOROFORM-d) 6=8.23 (s, 1H), 8.20-8.12 (m, 2H), 7.48 (s, 1H), 7.35 (s, 1H), 7.23 (d, J=8.2 Hz, 2H), 4.75 (s, 2H), 2.39 (d, J=2.3 Hz, 6H).

Synthetic Scheme C

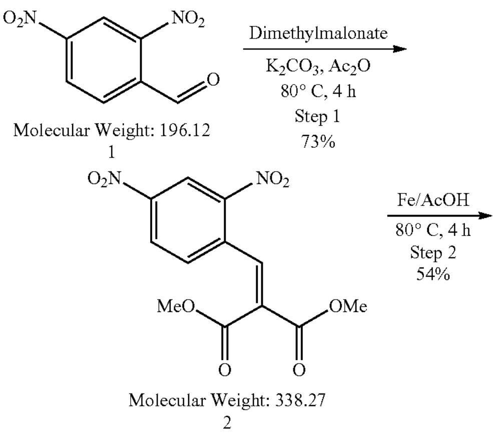

-continued

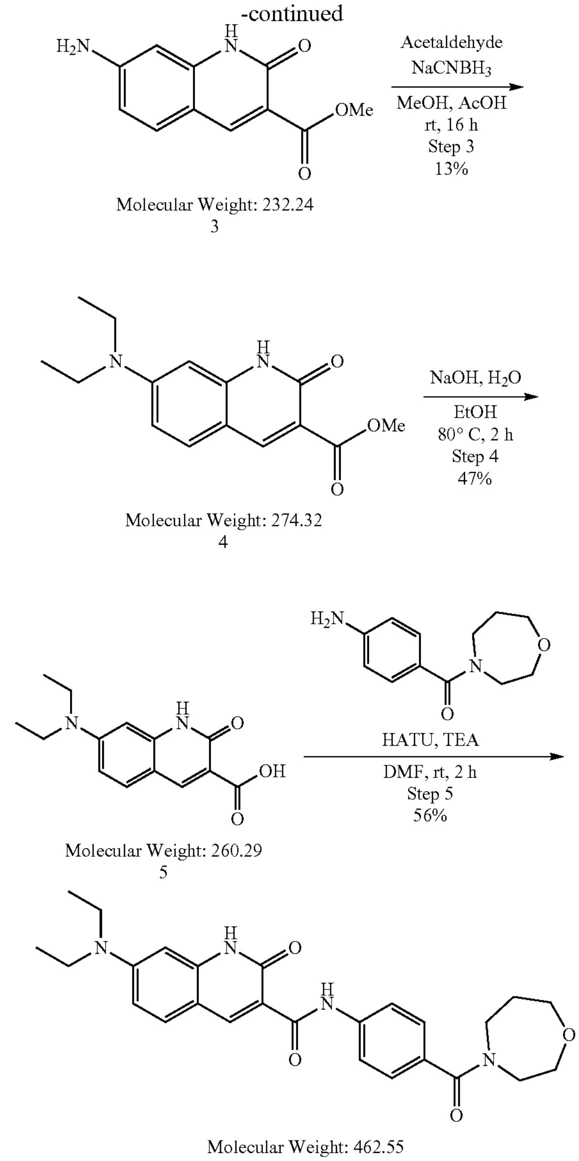

2.1 Dimethyl 2-(2,4-dinitrobenzylidene)malonate. Step 1. To a mixture of 2,4-dinitrobenzaldehyde (500 mg, 2.55 mmol, 1.0 eq) in acetic anhydride (1.09 mL) was added dimethyl malonate (336.8 mg, 2.55 mmol, 1.0 eq) followed by anhydrous potassium carbonate (528.5 mg, 3.82 mmol, 1.5 eq). The resulting reaction mixture was heated to 80° C. and stirred for 4 h. After completion of the reaction was confirmed by TLC (100% DCM), cold water was poured in mixture and was extracted with ethyl acetate. Organic layer then washed with brine solution, dried over anhydrous sodium sulfate, filtered, and concentrated to yield crude product. The product was then purified by column chromatography (90% DCM:Hexanes) to yield pure product (575 mg, 73%).

2.2 Methyl 7-amino-2-oxo-1,2-dihydroquinoline-3-carboxylate. Step 2. To Compound 2 (540 mg, 1.74 mmol, 1.0 eq) in AcOH (5.8 mL) was added iron powder (1.94 g, 34.81 mmol, 20 eq) at rt. The resulting mixture was heated to 80° C. and stirred for 4 h. After reaction completion confirmed by TLC (5% MeOH:DCM), the reaction mixture was filtered through celite and washed with ethyl acetate. The filtrate was basified using sodium bicarbonate and extracted with ethyl acetate. The organic layer was washed with brine solution, dried over anhydrous sodium sulfate, filtered, and evaporated under reduced pressure to yield product (207 mg, 54%), which was carried forward to next step without purification.

2.3 Methyl 7-(diethylamino)-2-oxo-1,2-dihydroquinoline-3-carboxylate. Step 3. To Compound 3 (200 mg, 0.95 mmol, 1.0 eq) in methanol (2.37 mL) was added acetaldehyde (0.46 mL, 8.3 mmol, 8.75 eq) at rt followed by addition of acetic acid (0.46 mL) and sodium cyanoborohydride (46.5 mg, 0.73 mmol, 0.78 eq). The resulting reaction mixture was stirred at rt for 16 h. After reaction completion confirmed by TLC (10% MeOH:DCM), reaction mixture diluted with DCM and washed with cold water and brine solution. Organic layer filtered, dried over sodium sulfate, and evaporated to yield crude product, which was then purified by column chromatography (30% EtOAc:DCM) to yield product (30 mg, 13%).

2.4 7-(diethylamino)-2-oxo-1,2-dihydroquinoline-3-carboxylic acid. Step 4. To Compound 4 (30 mg, 0.109 mmol, 1.0 eq) in EtOH (0.9 mL) at 0° C. was added NaO solution (21.9 mg, 0.547 mmol, 5.0 eq in 0.6 mL water). The reaction was then allowed to stir at 80° C. for 2 h. After reaction completion, the mixture was poured into cold water and the pH was adjusted to 5 using 5% citric acid solution. The solid that formed was collected by filtration and washed with water and diethyl ether to yield product (18 mg, 48%).

2.5 Procedure to access final product. Step 5. To starting material (18 mg, 0.069 mmol, 1.0 eq) and (4-aminophenyl)(1,4-oxazepan-4-yl)methanone (18.3 mg, 0.083 mmol, 1.2 eq) in anhydrous DMF (0.54 mL) at 10° C. was added HATU (39.4 mg, 0.104 mmol, 1.5 eq) and triethyl amine (0.115 mL, 0.083 mmol, 1.2 eq). The mixture was stirred at rt for 2 h. After consumption of starting materials, the reaction mixture was poured into cold water and extracted with ethyl acetate. The organic layer was then dried over anhydrous sodium sulfate and concentrated. The crude material was purified using prep-HPLC to yield pure product (17.9 mg, 56%). [M+H]+=463.5. 1H NMR (300 MHz, DMSO-d6) δ=12.33 (s, 1H), 11.96 (s, 1H), 8.68 (s, 1H), 7.72 (dd, J=8.8, 11.1 Hz, 3H), 7.38 (d, J=8.2 Hz, 2H), 6.79 (dd, J=2.3, 8.8 Hz, 1H), 6.54 (s, 1H), 3.66 (br s, 6H), 3.51-3.36 (m, 6H), 1.72 (br s, 2H), 1.14 (t, J=6.7 Hz, 6H).

Synthetic scheme D

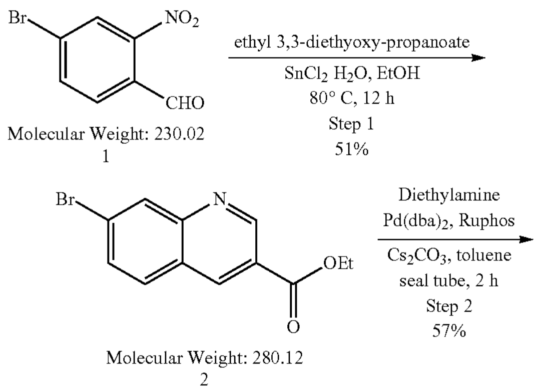

-continued

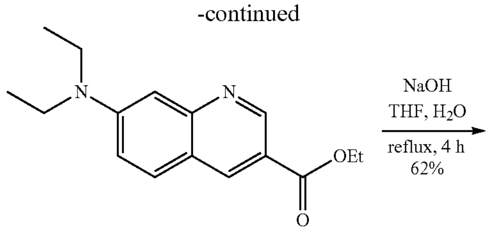

Molecular Weight: 272.36
3

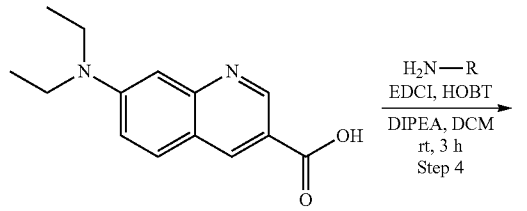

Molecular Weight: 244.29
4

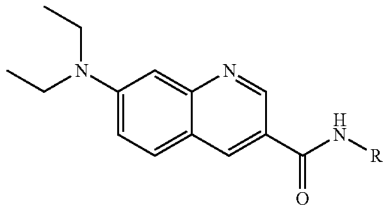

3.1 Ethyl 7-bromoquinoline-3-carboxylate. Step 1. To a mixture of 4-bromo-3-nitrobenzaldehyde (2.42 g, 10.51 mmol, 1.0 eq) in ethanol (80.8 mL) was added ethyl 3,3-diethoxypropanoate (4 g, 21.02 mmol, 2.0 eq) followed by tin chloride hydrate (10.68 g, 47.3 mmol, 4.5 eq). The reaction was allowed to reflux at 80° C. for 12 h. After completion of the reaction, ethanol was concentrated off under pressure. The mixture was then diluted with EtOAc and sodium bicarbonate and allowed to stir for 30 minutes. The mixture was then filtered over celite to remove undissolved salts. The organic layer was separated and the aqueous layer was then extracted with EtOAc (2×). The combined organic layers were filtered and dried over sodium sulfate and concentrated. The crude product was then washed with hexane, filtered, and dried under reduced pressure to yield pure product (1.5 g, 51%).

3.2 Ethyl 7-(diethylamino)quinoline-3-carboxylate. Step 2. To a solution of Compound 2 (1.4 g, 4.998 mmol, 1.0 eq) in toluene (139 mL) was added diethylamine (1.8 mL, 17.5 mmol, 3.5 eq). The mixture was purged with argon for 15 min followed by the addition of $Pd_2(dba)_3$ (458 mg, 0.4998 mmol, 0.1 eq), RuPhos (466 mg, 0.9996 mmol, 0.2 eq), and cesium carbonate (5.94 g, 18.24 mmol, 3.65 eq). The resulting mixture was heated to reflux and stirred for 2 h. After completion of the reaction, the reaction mixture was diluted with ethyl acetate and filtered. The filtrate was washed with water and brine. The organic layer was then d ed over anhydrous sodium sulfate, filtered, and evaporated under reduced pressure to yield crude material. Crude material then purified by column chromatography (0-20% EtOAc: Hexanes) to yield pure product (779 mg, 57%).

3.3 7-(diethylamino)quinoline-3-carboxylic acid. Step 3. To a solution of Compound 3 (779 mg, 2.86 mmol, 1 eq) in THF (7.6 mL) was added NaOH solution (629 mg, 15.7 mmol, 5.5 eq in 7.6 mL water) at rt. The resulting mixture was allowed to stir at reflux for 4 h. After reaction completion confirmed by TLC (10% MeOH:DCM), excess THF was evaporated at remaining residue diluted with water and washed with ethyl acetate. The aqueous layer pH was adjusted to 5 using 10% aqueous citric acid solution and extracted with ethyl acetate. The organic layer was washed with brine solution, dried over anhydrous sodium sulfate, filtered, and concentrated to yield product as a yellow solid (431 mg, 62% yield).

3.4 General Procedure to access final products. Step 4. To a solution of Compound 4 (50 mg, 0.205 mmol, 1.0 eq) in DCM (2.1 mL) was added amine (0.184 mmol, 0.9 eq) followed by DIPEA (0.071 mL, 0.409 mmol, 2.0 eq), HOBt (34.5 mg, 0.225 mmol, 0.1 eq), and EDCI (43.2 mg, 0.225 mmol, 1.1 eq). The resulting mixture was stirred at rt for 3 h. After completion of the reaction confirmed by TLC (5% MeOH:DCM), mixture diluted with DCM and washed with cold water, brine solution, filtered, dried over sodium sulfate, and evaporated to afford crude compound. The product was purified by column chromatography (2% MeOH:EtOAc).

| Molecular Structure | Amine | Yield | $[M + H]^+$ | Annotated H NMR |
|---|---|---|---|---|
| 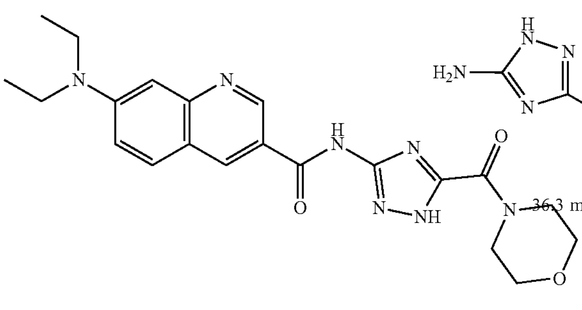 | 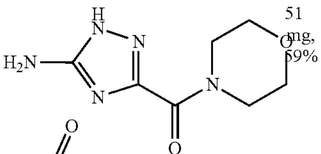 | 51 mg, 59% 36.3 mg | 424.0 | 1H NMR (300 MHz, METHANOL-d4) δ ppm 9.24 (d, J = 2.34 Hr, 1 H) 9.03 (d, J = 2.34 Hz, 1 H) 7.85 (d, J = 8.79 Hz, 1 H) 7.32 (dd, J = 9.08, 2.64 Hz, 1 H) 7.02 (d, 2.34 Hz, 1 H) 3.81-3.87 (m, 2 H) 3.73-3.79 (m, 4 H) 3.69-3.72 (m, 2 H) 3.60 (q, J = 7.03 Hz, 4 H) 1.25-1.31 (m, 6 H) |

-continued

| Molecular Structure | Amine | Yield | [M + H]$^+$ | Annotated H NMR |
|---|---|---|---|---|
| 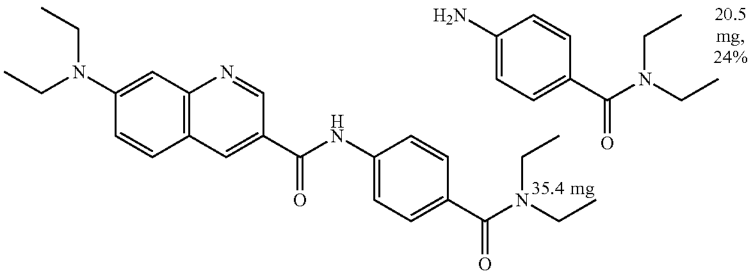 | 35.4 mg | 20.5 mg, 24% | 419.2 | 1H NMR (300 MHz, METHANOL-d4) δ ppm 9.10 (d, J = 1.76 Hr, 1 H) 8.67 (d, = 2.34 Hz, 1 H) 7.86 (dd, J = 8.79, 1.76 Hz, 4 H) 7.41 (d, J = 8.79 Hz, 2 H) 7.33 (dd, J = 9.08, 2.64 Hz, 1 H) 7.05 (d, J = 2.34 Hz, 1 H) 3.59 (q, J = 7.03 Hz, 7 H) 1.28 (br t, = 7.03 Hz, 12 H) |
| 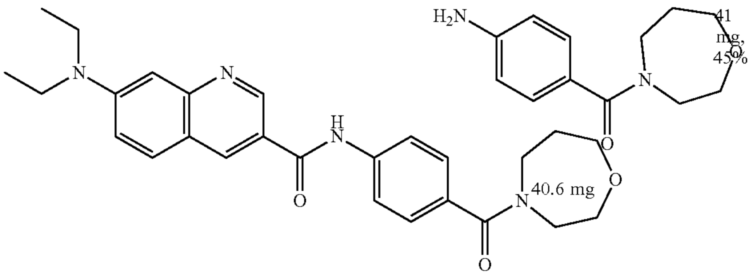 | 40.6 mg | 41 mg, 45% | 447.0 | 1H NMR (300 MHz, DMSO-d6) δ ppm 9.13 (d, J = 2.34 Hz, 1 H) 8.66 (d, J = 1.76 Hz, 1 H) 7.79-7.90 (m, 3 H) 7.40 (d, J = 8.79 Hz, 2 H) 7.29 (dd, J = 9.38, 2.93 Hz, 1 H) 6.99 (d, J = 2.34 Hz, 1 H) 3.58-3.75 (m, 6 H) 3.51 (m, J = 7.42, 7.42, 7.42 Hz, 6 H) 1.79-1.91 (m, 1 H) 1.68-1.78 (m, 1 H) 1.15-1.20 (m, 7 H) |
| 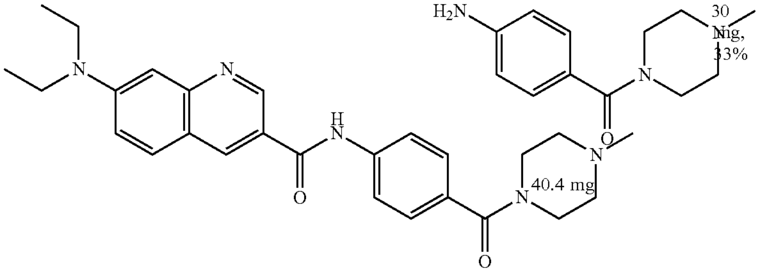 | 40.4 mg | 30 mg, 33% | 446.6 | 1H NMR (300 MHz, DMSO-d4) δ ppm 9.22 (br s, 2 H) 8.11 (br d, J = 9.38 Hz, 1 H) 7.94 (br d, J = 8.21 Hz, 2 H) 7.50-7.66 (m, 3 H) 7.00 (s, 1 H) 3.64-3.74 (m, 4 H) 3.42-3.64 (m, 4 H) 3.32-3.37 (m, 1 H) 3.13-3.29 (m, 3 H) 2.96 (s, 3 H) 3.32 (br t, J = 7.03 Hz, 6 H) |

Scheme 1. Synthetic scheme for N-(4-diethylcarbamoyl)phenyl)-4-methyl-2-oxo-1,2-dihydroquinoline-3-carboxamide

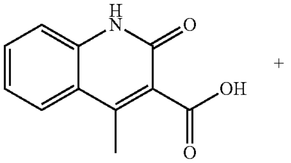

M Wt: 203.20
1.1

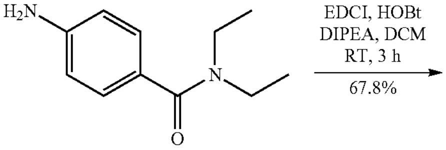

M Wt: 192.26
1.2

-continued

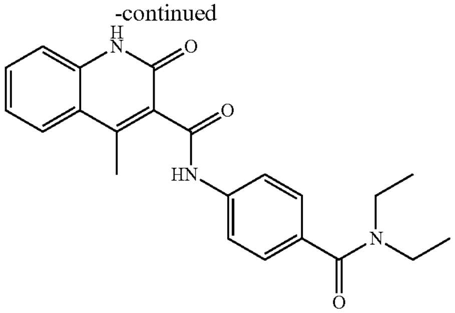

M Wt: 377.44

N-(4-(diethylcarbamoyl)phenyl)-4-methyl-2-oxo-1,2-dihydroquinoline-3-carboxamide: To a solution of compound-1.1 (50.0 mg, 0.246 mmol) in anhydrous dichloromethane (2 mL) was added compound-1.2 (42.6 mg, 0.221 mmol) followed by the addition of EDCI (51.9 mg, 0.271 mmol), HOBt (36.6 mg, 0.271 mmol) and DIPEA (0.0857 mL, 0.492 mmol) at 20° C. and the resulting reaction mixture was stirred room temperature for 3 h. The reaction mixture was diluted with dichloromethane and washed with water. Water layer was extracted with ethyl acetate and combined organic layers were dried over anhydrous sodium sulfate, filtered and evaporated under reduced pressure. The resultant crude compound was purified by using 12 g silica flash column, eluted with MeOH:DCM (0 to 10%) gave desired product as a white solid (63 mg, 67.8%). (+esi)$[M+H]^+$=378.2. $^1$H NMR (300 MHz, DMSO-d6) δ=12.00 (s, 1H), 10.55 (s, 1H), 7.82 (d, J=7.6 Hz, 1H), 7.73 (d, J=8.2 Hz, 2H), 7.62-7.52 (m, 1H), 7.39-7.15 (m, 4H), 3.42-3.14 (m, 4H), 2.43 (s, 3H), 1.09 (br s, 6H).

Scheme 2. Synthetic scheme for N-(4-diethylcarbamoyl)phenyl)-7-fluoro-2-oxo-1,2-dihydroquinoline-3-carboxamide

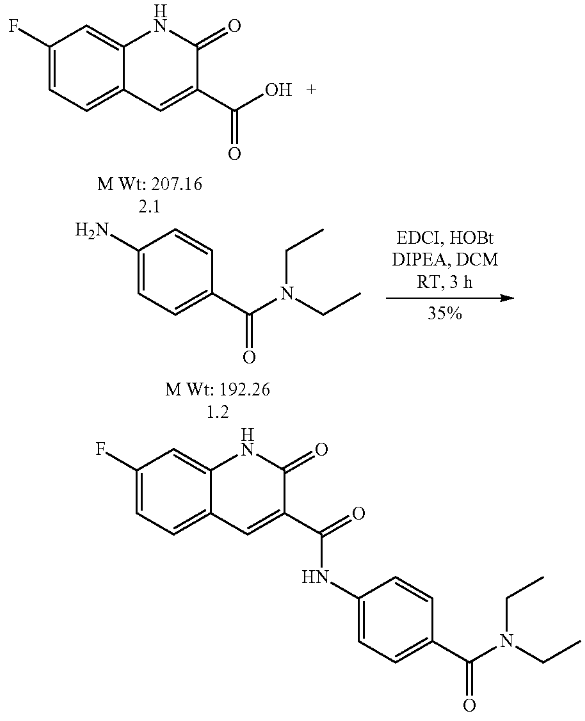

M Wt: 207.16
2.1
M Wt: 192.26
1.2
M Wt: 381.41

N-(4-(diethylcarbamoyl)phenyl)-7-fluoro-2-oxo-1,2-dihydroquinoline-3-carboxamide: To a solution of compound-2.1 (50 mg, 0.241 mmol) in anhydrous dichloromethane (2 mL) was added compound-1.2 (41.8 mg, 0.217 mmol) followed by the addition of EDCI (50.9 mg, 0.265 mmol), HOBt (35.9 mg, 0.265 mmol) and DIPEA (0.0841 mL, 0.483 mmol) at 20° C. and the resulting reaction mixture was stirred at room temperature for 3 h. The reaction mixture was diluted with dichloromethane and washed with water. Water layer was extracted with ethyl acetate and combined organic layers were dried over anhydrous sodium sulfate, filtered and evaporated under reduced pressure. The resultant crude compound was purified by using 12 g silica flash column, eluted with MeOH:DCM (0 to 10%) gave desired product along with some impurity. Finally, the compound was triturated with 30% hexane in DCM afforded desired product as an off white solid (32 mg, 35%). (+esi)$[M+H]^+$=382.2. $^1$H NMR (300 MHz, DMSO-d6) δ=12.74 (s, 1H), 12.11 (s, 1H), 8.99 (s, 1H), 8.12 (dd, J=6.4, 8.8 Hz, 1H), 7.76 (d, J=8.2 Hz, 2H), 7.36 (d, J=8.2 Hz, 2H), 7.28-7.11 (m, 2H), 3.47-3.16 (m, 4H), 1.09 (br s, 6H).

Scheme-3. Synthetic scheme for compound N-(4-(1,4-oxazepane-4-carbonyl)phenyl)-6-methoxy-2-oxo-1,2-dihydroquinoline-3-carboxamide

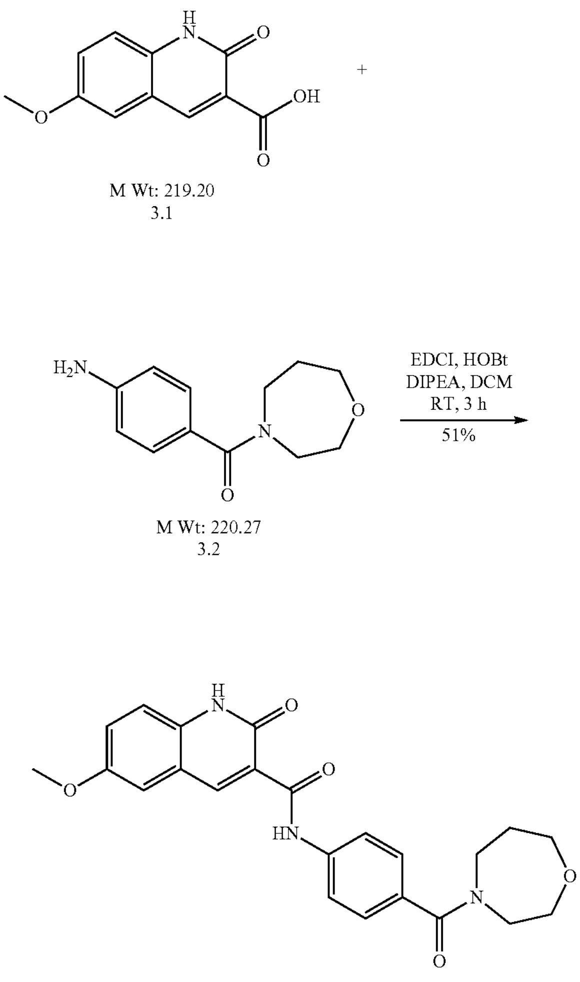

M Wt: 219.20
3.1
M Wt: 220.27
3.2
M Wt: 421.45

N-(4-(1,4-oxazepane-4-carbonyl)phenyl)-6-methoxy-2-oxo-1,2-dihydroquinoline-3-carboxamide: To a solution of compound-3.1 (50 mg, 0.228 mmol) in anhydrous dichloromethane (2 mL) was added compound-3.2 (45.2 mg, 0.205 mmol) followed by the addition of EDCI (48.1 mg, 0.251 mmol), HOBt (33.9 mg, 0.251 mmol) and DIPEA (0.0795 mL, 0.456 mmol) at 20° C. and the resulting reaction mixture was stirred at room temperature for 3 h. After completion of the reaction, the reaction mixture was diluted with dichloromethane and washed with water. Water layer was extracted with ethyl acetate and combined organic layers were dried over anhydrous sodium sulfate, filtered and evaporated. The resultant crude compound was purified by using 12 g silica flash column, eluted with MeOH:DCM (0 to 5%) gave desired product along with some aniline (3.2). Finally purified by PLC using DCM: Acetone:Hexane (40:40:20) and dried to afford desired product as a pale yellow solid (49 mg, 51%), (+esi)$[M+H]^+$=422.2. $^1$H NMR (300 MHz, DMSO-d6) δ=12.64 (s, 1H), 12.42 (s, 1H), 8.95 (s, 1H), 7.77 (br d, J=8.2 Hz, 2H), 7.57 (d, J=2.3 Hz, 1H), 7.46-7.28 (m, 4H), 3.81 (s, 3H), 3.73-3.41 (m, 8H), 1.92-1.66 (m, 2H).

Scheme 4. Synthetic scheme for compound N-(4-(1,4-oxazepane-4-carbonyl)phenyl)-6-methoxy-2-methylquinoline-3-carboxamide

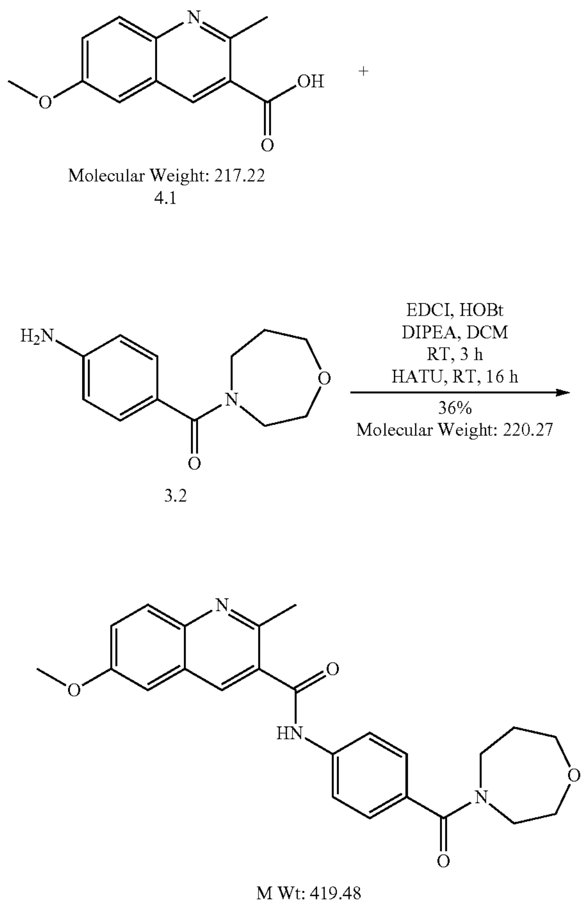

N-(4-(1,4-oxazepane-4-carbonyl)phenyl)-6-methoxy-2-methylquinoline-3-carboxamide: To a solution of compound-4.1 (53.0 mg, 0.244 mmol) in anhydrous dichloromethane (2.12 mL) was added compound-3.2 (48.4 mg, 0.220 mmol) followed by the addition of EDCI (51.4 mg, 0.268 mmol), HOBt (36.3 mg, 0.268 mmol) and DIPEA (0.085 mL, 0.488 mmol) at 20° C. and the resulting reaction mixture was stirred at room temperature for 3 h. TLC and LCMS showed no sign of any product formation. Therefore, HATU (139 mg, 0.366 mmol, 1.5 eq) was added and stirred at room temperature overnight. The reaction mixture was diluted with dichloromethane and washed with water. Water layer was extracted with ethyl acetate and combined organic layers were dried over anhydrous sodium sulfate, filtered and evaporated. The resultant crude compound was purified by using 12 g silica flash column, eluted with MeOH:DCM (0 to 30%), the desired fractions were concentrated, dissolved in DCM and washed with saturated $NaHCO_3$ solution, organic layer was dried over anhydrous sodium sulfate, filtered and concentrated. The compound was again purified by using 12 g silica flash column, eluted with MeOH:DCM (0 to 10%) gave desired product as a pale yellow solid (3 mg, 36%). (+esi)$[M+H]^+$=420.2. $^1H$ NMR (300 MHz, CHLOROFORM-d) δ=8.14 (s, 1H), 7.95 (d, J=9.4 Hz, 1H), 8.04-7.83 (m, 1H), 7.70 (s, 1H), 7.52-7.28 (m, 3H), 7.03 (d, J=2.3 Hz, 1H), 3.93 (s, 3H), 3.87-3.53 (m, 9H), 2.84 (s, 3H), 1.94-1.55 (m, 2H).

Scheme 5. Synthetic scheme for compound 7-amino-N-(4-(diethylcarbamoyl)phenyl)quinoline-3-carboxamide

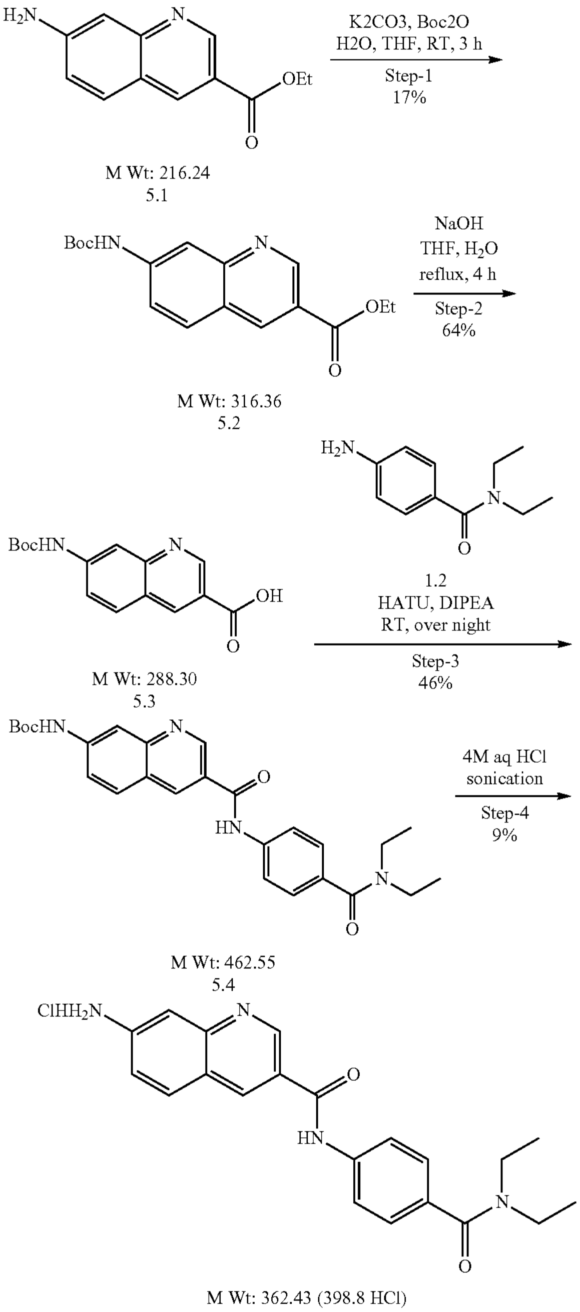

ethyl 7-((tert-butoxycarbonyl)amino)quinoline-3-carboxylate. Step-1: To a stirred solution of compound-5.1 (100 mg, 0.462 mmol) in tetrahydrofuran (1 mL) and $H_2O$ (8.33 mg, 0.462 mmol) was added potassium carbonate sesquihydrate (128 mg, 0.925 mmol). After about five minutes, di-tert-butyl dicarbonate (118 mg, 0.541 mmol) was added and the reaction mixture was allowed to stir for 3 h at room temperature. The mixture was diluted with water and extracted three times with ethyl acetate. The combined organic layers were dried over anhydrous sodium sulfate, filtered and concentrated under reduced pressure. The product was purified by flash chromatography (0-20% EtOAc:

Hexane) to afford compound-5.2 as a light yellow solid (25 mg, 17%) along with 50 mg of un reacted starting material.

7-((tert-butoxycarbonyl)amino)quinoline-3-carboxylic acid. Step-2: To a solution of compound-5.2 (105 mg, 332 mmol) in tetrahydrofuran (2 mL) was added sodium hydroxide (26.6 mg, 0.665 mmol) and the resulting reaction mixture was stirred at room temperature for 56 h. Excess of solvent was removed by distillation under reduced pressure and the residue pH was adjusted to 4 using 0.1 M HCl and the compound was extracted with ethyl acetate and the organic layer was dried over anhydrous sodium sulfate, filtered and evaporated under reduced pressure to yield compound-5.3 (62 mg, 64%). (+esi)$[M+H]^+$=289.2.

tert-butyl (3-((4-(diethylcarbamoyl)phenyl)carbamoyl) quinolin-7-yl)carbamate. Step-3: To a solution of compound-5.3 (62 mg, 0.22 mmol) in dimethylformamide (1 mL) were added compound-1.2 (41 mg, 0.22 mmol), DIPEA (83 mg, 0.65 mmol) and HATU (120 mg, 320 mmol) and the resulting reaction mixture was stirred at room temperature for overnight. The reaction mixture was diluted with ethyl acetate and washed with cold water and dried over anhydrous sodium sulfate, filtered and evaporated under reduced pressure to afford crude compound and it was purified by combi-flash to afford pure compound-5.4 as a yellow solid (46 mg, 46%), (+esi)$[M+H]^+$=463.3.

7-amino-N-(4-(diethylcarbamoyl)phenyl)quinoline-3-carboxamide. Step-4: 4M aqueous HCl (1 mL) was added to compound-5.4 (46 mg) and stirred for 5-10 min at room temperature followed by sonicated for 20 min. LCMS analysis indicates the formation of product along with un-reacted starting material. To the reaction mixture methanol (2 mL) was added and sonicated followed by removal of methanol. The residue was lyophilized to obtain a hygroscopic yellow powder (3.2 mg, 9%). (+esi)$[M+H]^+$=363.2. $^1H$ NMR (300 MHz, CD3OD) δ=9.20 (s, 1H), 9.16 (d, J=1.8 Hz, 1H), 8.04 (d, J=9.4 Hz, 1H), 7.89 (d, J=8.8 Hz, 2H), 7.44 (d, J=8.8 Hz, 2H), 7.36 (dd, J=2.1, 9.1 Hz, 1H), 7.00 (d, J=1.8 Hz, 1H), 3.67-3.48 (m, 2H), 3.45-3.33 (m, 2H), 1.34-1.10 (m, 6H).

Scheme 6. Synthetic scheme for compound N-(4-(1,4-oxazepane-4-carbonyl)phenyl)-6-aminoquinoline-3-carboxamide hydrochloride

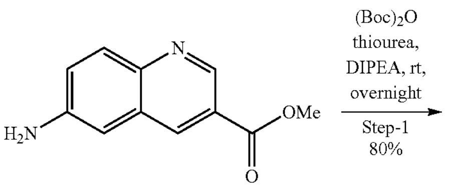

M Wt: 202.21
6.1

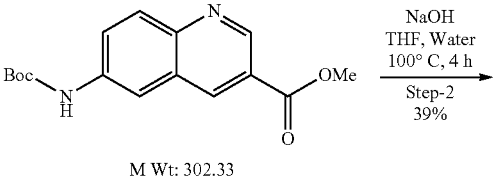

M Wt: 302.33
6.2

-continued

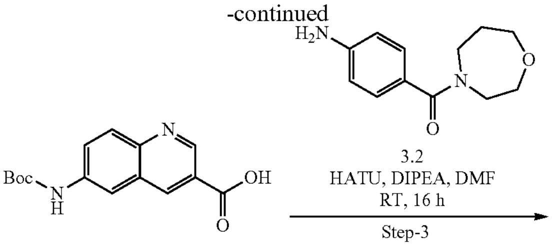

M Wt: 288.30
6.3

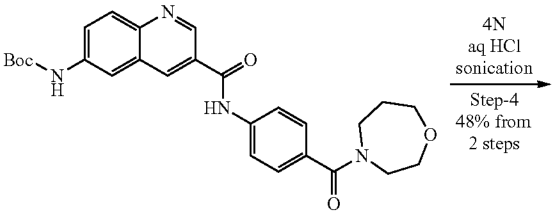

M Wt: 490.56
6.4

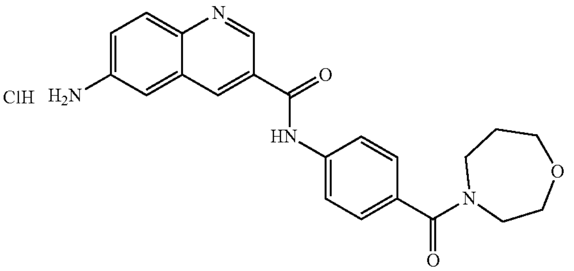

M Wt: 390.44 (-HCl)

Methyl 6-((tert-butoxycarbonyl)amino)quinoline-3-carboxylate. Step-1: To a solution of compound-6.1 (150 mg, 0.742 mmol) in dry tetrahydrofuran (6.0 mL) ere added thiourea (5.65 mg, 0.0742 mmol) and DIPEA (0.0646 mL, 0.371 mmol) and the resulting reaction mixture was stirred for 5 min at room temperature and then Boc anhydride (178 mg, 0.816 mmol) was added and stirred at room temperature overnight. The progress of the reaction was monitored by LCMS and showed only 25% conversion. This reaction mixture was concentrated and another 5 eq of Boc anhydride and 1.5 mL of dry THF were added and the reaction mixture was heated to 70° C. and stirred for 3 h and LCMS showed that 95% conversion to product. Excess THF was evaporated; water (5 mL) was added to the mixture, extracted with ethyl acetate (3×10 mL), dried over anhydrous sodium sulfate, filtered and concentrated. Purified by pre packed silica gel column (12 g), eluted with Hexane in ethyl acetate (0 to 50%) afforded desired compound-6.2 as a white powder (180 mg, 80%).

6-((tert-butoxycarbonyl)amino)quinoline-3-carboxylic acid. Step-2: A seal tube was charged with compound-6.2 (180 mg, 0.595 mmol) and Sodium hydroxide (131 mg, 3.27 mmol) in tetrahydrofuran (1.80 mL) and water (1.80 mL) and stirred at 70° C. for 3 h. LCMS indicated 51% desired product and 45% de-boc product. Then the THF was removed under reduced pressure and crude was diluted with water, washed with ethyl acetate (2×5 mL). Aqueous layer pH was adjusted to 5 with 10% citric acid solution and then extracted with ethyl acetate. Organic layer was washed with brine, dried over anhydrous sodium sulfate, filtered and concentrated. The crude compound was purified by pre packed silica gel column (12 g), eluted with DCM in MeOH (0 to 10%) afforded desired compound-6.3 (132 mg, 39%).

tert-butyl (3-((4-(1,4-oxazepane-4-carbonyl)phenyl)carbamoyl)quinolin-6-yl)carbamate. Step-3: A flame dried seal tube was charged with compound-6.3 (65 mg, 0.225 mmol) and compound-3.2 (59.6 mg, 0.271 mmol) in anhydrous dimethylformamide (1.95 mL). Then HATU (129 mg, 0.338 mmol) and DIPEA (0.0471 mL, 0.271 mmol) were added and the reaction mixture was stirred at room temperature for overnight. The reaction mixture was diluted with water, extracted with ethyl acetate and the organic layer was then washed with water, dried over anhydrous sodium sulfate, filtered and evaporated. The resultant crude compound was purified by using 24 g silica flash column, eluted with MeOH:$CHCl_3$ gave desired compound-6.4 and used for next step.

N-(4-(1,4-oxazepane-4-carbonyl)phenyl)-6-aminoquinoline-3-carbo amide hydrochloride. Step-4: 4M aqueous HCl (1 mL) was added to compound-6.4 obtained from step-3 and sonicated for 20 min followed by lyophilization to yield desired product HCl salt s a yellow solid (46 mg; 48% from 2 steps). (+esi)$[M+H]^+$=391.2. $^1$H NMR (400 MHz, CD3OD) 9.27 (d, J=1.6 Hz, 1H), 9.17 (d, J=1.8 Hz, 1H), 8.03 (d, J=9.2 Hz, 1H), 7.92 (d, J=8.0 Hz, 2H), 7.71 (dd, J=9.1, 2.4 Hz, 1H), 7.52 (d, J=7.9 Hz, 2H), 7.31 (d, J=2.5 Hz, 1H), 3.88-3.63 (m, 8H), 2.05-2.00 (m, 1H), 1.88-1.83 (m, 1H).

Scheme 7. Synthetic scheme for compound 6-amino-N-(4-(diethylcarbamoyl)phenyl)quinoline-3-carboxamide HCl salt

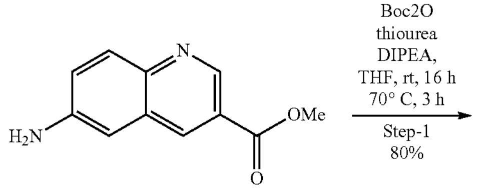

Molecular Weight: 202.21
7.1

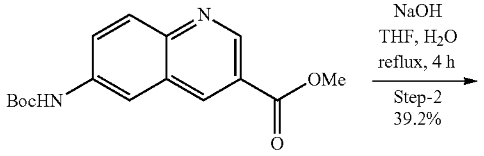

M Wt: 302.33
7.2

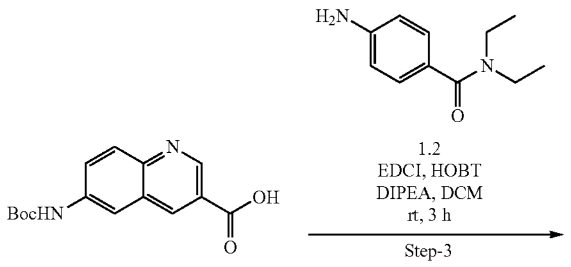

Molecular Weight: 288.30
7.3

-continued

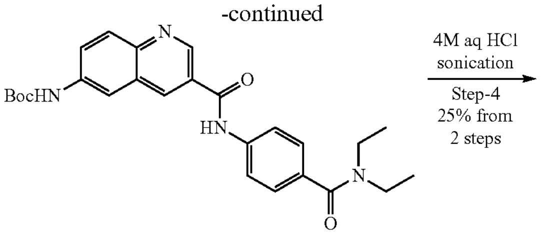

M Wt: 462.55
7.4

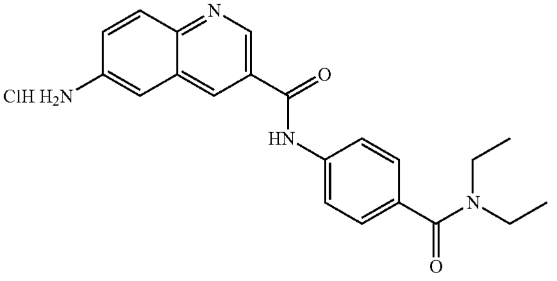

M Wt: 362.43 (-HCl)

methyl 6-((tert-butoxycarbonyl)amino)quinoline-3-carboxylate. Step-1: To a solution of compound-7.1 (150 mg, 0.742 mmol) in tetrahydro-furan (4 mL) were added thiourea (5.6 mg, 0.074 mmol), DIPEA (47.9 mg, 0.371 mmol) and boc anhydride (177 mg, 0.816 mmol) and the resulting reaction mixture was stirred at room temperature for 16 h. The progress of the reaction was monitored by LCMS and showed 25% of product formation. The solvent was removed from the reaction mixture and another 5 eq of boc anhydride and 1.5 mL of TIF were added and heated the reaction mixture to 70° C. and stirred for 3 h and LCMS analysis indicates 95% formation of product. Then solvent was removed under reduced pressure and the residue was dissolved in ethyl acetate and washed with water and dried over anhydrous sodium sulfate, filtered and evaporated under reduced pressure to yield crude compound and it was Purified by 12 g flash column with 0-50% EA:Hex to elute the product then 100% EA to elute un-reacted starting material. The product fractions were distilled under reduced pressure to yield pure compound as a white color compound-7.2 (180 mg, 80%). (+esi)[M+H]=303.2.

6-((tert-butoxycarbonyl)amino)quinoline-3-carboxylic acid. Step-2: To a solution of compound-7.2 (180 mg, 0.595 mmol) in tetrahydrofuran (1.8 mL) were added sodium hydroxide (130 mg, 3.27 mmol) and water (1.8 mL) and the resulting reaction mixture was stirred at 70° C. for 3 h. The progress of the reaction was monitored by LCMS and indicates the formation of 51% desired product and 45% de-boc product. At this stage the reaction was discontinued and excess of tetrahydrofuran was removed under reduced pressure and the crude residue was dissolved in water and washed with water. The aqueous layer was then acidified to pH 5 using 10% citric acid solution and extracted with ethyl acetate. The organic layer was washed with brine solution and dried over anhydrous sodium sulfate, filtered and concentrated under reduced pressure to yield compound-7.3 (132 mg, 39.2%; 51% purity). (+esi)$[M+H]^+$=289.2.

tert-butyl (3-((4-(diethylcarbamoyl)phenyl)carbamoyl)quinolin-6-yl)carbamate. step-3: To a solution of compound-7.3 (65 mg, 0.225 mmol) in anhydrous DMF (1.95 mL) were added compound-1.2 (52 mg, 0.271 mmol), DIPEA (0.047 mL, 0.271 mmol) aid HATU (129 mg, 0.338 mmol) and the resulting reaction mixture was stirred at room temperature for 4 h. The reaction mixture was diluted with water and extracted with ethyl acetate. The organic layer washed with water, dried over anhydrous sodium sulfate, filtered and concentrated under reduced pressure to yield crude compound and it was purified by 24 g of silica gel column by eluting with chloroform and methanol to afford compound-7.4 and used for next step. (+esi) $[M+H]^+$=463.4.

6-amino-N-(4-(diethylcarbamoyl)phenyl)quinoline-3-carboxamide HCl salt. Step-4: 4M aqueous HCl (1 mL) was added to compound-7.4 obtained from step-3 and sonicated for 20 min. LCMS indicates the completion of the reaction. Excess reagent was removed by lyophilization and the solid obtained was washed with ether and dried t yield desired product as a yellow solid (18 mg, 25% from 2 steps). (+esi)$[M+H]^+$=363.3 (-HCl). $^1$H NMR (400 MHz, CD3OD) δ=9.28 (s, 1H), 9.18 (s, 1H), 8.03 (d, J=9.3 Hz, 1H), 7.91 (d, J=8.5 Hz, 2H), 7.71 (dd, J=2.1, 9.1 Hz, 1H), 7.45 (d, J=8.5 Hz, 2H), 7.33 (d, J=2.3 Hz, 1H). 3.57 (br s, 2H), 3.37 (br s, 2H), 1.27 (br s, 3H), 1.18 (br s, 3H).

Scheme 8. Synthetic scheme for compound N-(4-(diethylcarbamoyl)phenyl)-2-methylquinoline-3-carboxamide

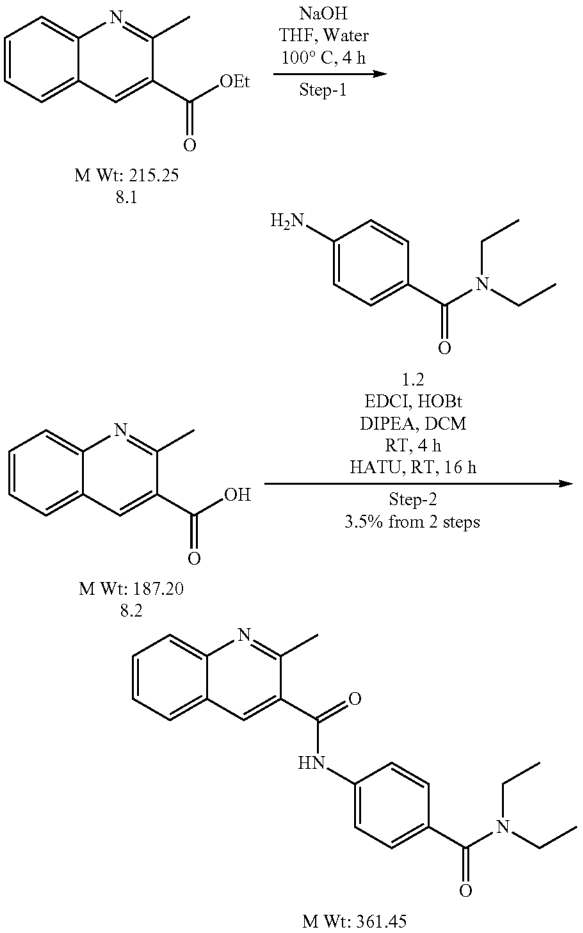

2-methylquinoline-3-carboxylic acid. Step-1: A seal tube was charged with compound-8.1 (100 mg, 0.465 mmol) and sodium hydroxide (102 mg, 2.56 mmol) in tetrahydrofuran (1 mL) and water (1 mL) and stirred at 100° C. for 4 h. TLC indicated complete conversion of SM to product. Then the tetrahydrofuran was removed under reduced pressure and crude was diluted with water, washed with ethyl acetate (2×5 mL). Aqueous layer pH was adjusted to 5 with 10% citric acid solution and then extracted with ethyl acetate. Organic layer was washed with brine, dried over anhydrous sodium sulfate, filtered and concentrated. The crude compound-8.2 was used for next step without further purification.

N-(4-(diethylcarbamoyl)phenyl)-2-methylquinoline-3-carboxamide. step-2: To a solution of compound-8.2 (70.0 mg, 0.374 mmol) in anhydrous dichloromethane (2.8 mL) was added compound-2 (64.7 mg, 0.337 mmol) followed by the addition of EDCI (78.9 mg, 0.411 mmol), HOBt (55.6 mg, 0.411 mmol) and DIPEA (0.130 mL, 0.748 mmol) at 20° C. and the resulting reaction mixture was stirred at room temperature for 3 h. TLC and LCMS showed no sign of any product formation. Therefore, HATU (213 mg, 0.561 mmol) was added and stirred at room temperature overnight. LCMS showed only 6% conversion. After routine work up, the resultant crude compound was purified by using 12 g silica flash column, eluted with MeOH:DCM (0 to 10%) gave impure desired product. This impure product was purified again by preparative HPLC provided pure compound as a white solid (6 mg, 3.5% from 2 steps). (+esi)$[M+H]^+$=362.2. $^1$H NMR (400 MHz, CD3OD) δ=8.64 (s, 1H), 8.12-8.03 (m, 2H), 7.90 (t, J=7.9 Hz, 1H), 7.85 (d, J=8.3 Hz, 2H), 7.75-7.66 (m, 1H), 7.44 (d, J=8.5 Hz, 2H), 3.57 (br s, 2), 3.37 (br s, 2H), 2.89 (s, 3H), 1.27 (br s, 3H), 1.18 (br s, 3H).

Scheme 9. Synthetic scheme for compound N-(4-(azepane-1-carbonyl)phenyl)-6-methoxy-2-methylquinoline-3-carboxamide

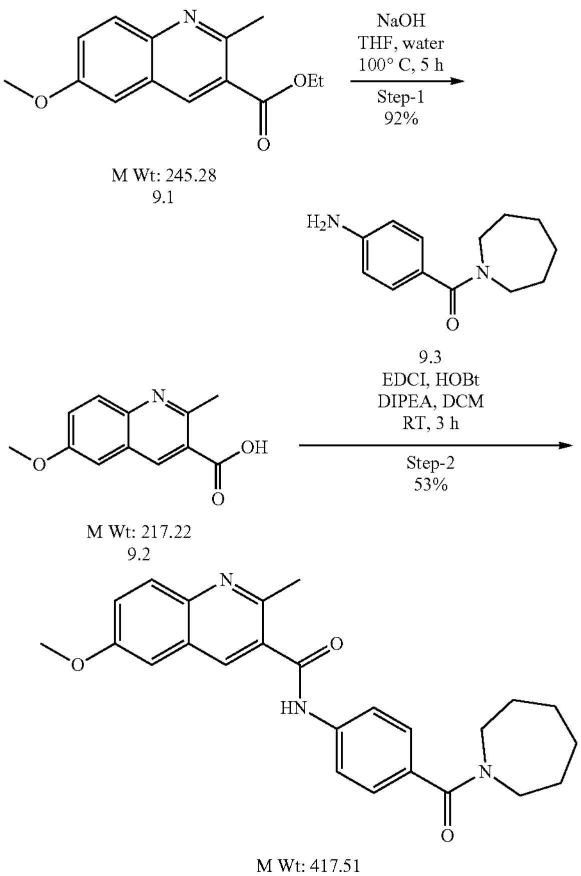

6-methoxy-2-methylquinoline-3-carboxylic acid. Step-1: A seal tube as charged with compound-9.1 (200 mg, 0.815 mmol) and Sodium hydroxide (179 mg, 4.48 mmol) in tetrahydrofuran (2.00 mL) and water (2.00 mL) and stirred at 100° C. for 5 h. TLC indicated complete conversion of SM to product. Then the THF was removed under reduced pressure and crude was diluted with water, washed with ethyl acetate (2×5 mL). Aqueous layer pH was adjusted to 5 with 10% citric acid solution and then extracted with ethyl acetate. Organic layer was washed with brine, dried over anhydrous sodium sulfate, filtered and concentrated. The crude compound-9.2 (163 mg, 92%) was used for next step without further purification.

N-(4-(azepane-1-carbonyl)phenyl)-6-methoxy-2-methylquinoline-3-carboxamide. Step-2: To a solution of compound-9.2 (50.0 mg, 0.230 mmol) in anhydrous dichloromethane (2 mL) was added compound-9.3 (45.2 mg, 0.207 mmol) followed by the addition of EDCI (48.5 mg, 0.253 mmol), HOBt (34.2 mg, 0.253 mmol) and DIPEA (0.0802 mL, 0.460 mmol) at 20° C. and the resulting reaction mixture was stirred at room temperature for 3 h. The reaction mixture was diluted with dichloromethane and washed with water. Water layer was extracted with ethyl acetate and combined organic layers were dried over anhydrous sodium sulfate, filtered and evaporated. The resultant crude compound was purified by using 12 g silica flash column, eluted with MeOH:DCM (0 to 10%) gave desired product as a pale-yellow solid (51 mg, 53%). (+esi)[M+H]$^+$=418.2. 1H NMR (300 MHz, CHLOROFORM-d) δ 8.14 (s, 1H), 8.01-7.90 (m, 1H), 7.68 (br d, J=8.2 Hz, 2H), 7.48-7.33 (m, 4H), 7.04 (d, J=2.9 Hz, 1H), 3.93 (s, 3H), 3.68-3.58 (m, 2H), 3.40 (br s, 2H), 2.84 (s, 3H), 1.87-1.73 (m, 2H), 1.60 (br s, 6H).

Scheme 10. Synthetic scheme for compound 2-(2-(4-dimethylamino) phenyl)-2-oxoethoxy)-4,6-dimethylnicotinonitrile

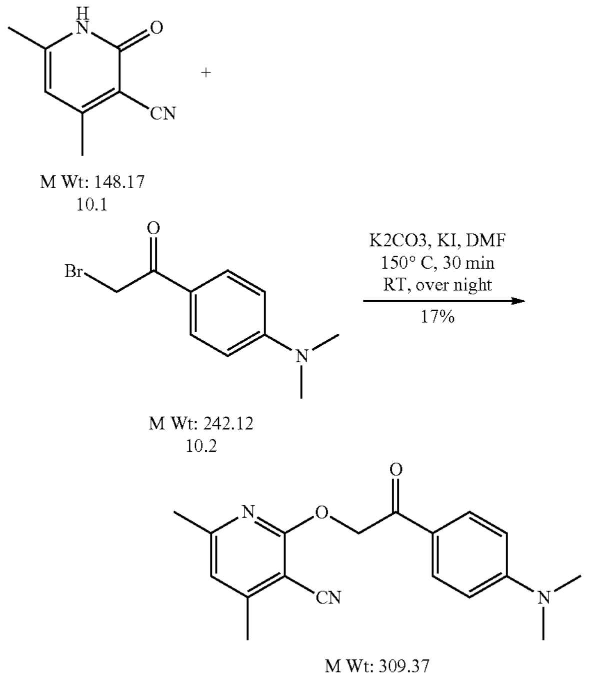

2-(2-(4-(dimethylamino)phenyl)-2-oxoethoxy)-4,6-dimethylnicotinonitrile: A flame dried vial was charged with compound-10.1 (200 mg, 1.35 mmol) in anhydrous di ethylformamide (6 mL), was added potassium carbonate (205 mg, 1.48 mmol) and potassium iodide (246 mg, 1.48 mmol). This reaction mixture was stirred at room temperature for 15 min, compound-10.2 (327 mg, 1.35 mmol) was added to the above reaction mixture and stirred at 50° C. for 30 min and at room temperature for overnight. TLC and LCMS showed complete conversion to product formation. The reaction mixture was poured into water (10 mL), extracted with ethyl acetate (3×10 mL) and combined organic layers were dried over anhydrous sodium sulfate, filtered and evaporated. The resultant crude compound was purified by using 12 g silica flash column, eluted with Hexane in ethyl acetate (0 to 30%), the desired fractions were concentrated, triturated with diethyl ether. Finally, the compound was purified by Prep HPLC, gave desired product (70 mg, 17%). (+esi)[M+H]$^{30}$=310.2. $^1$H NMR (300 MHz, CHLOROFORM-d) δ 7.88 (d, J=8.79 Hz, 2H) 6.64-6.71 (m, 3H) 5.59-5.65 (m, 2H) 3.07 (s, 6H) 2.45 (s, 3H) 2.30 (s, 3H).

Scheme 11. Synthetic scheme for compound 2-(2-(4-dimethylamino) phenyl)-2-oxoethoxy)-6,8-dimethylquinoline-3-carbonitrile

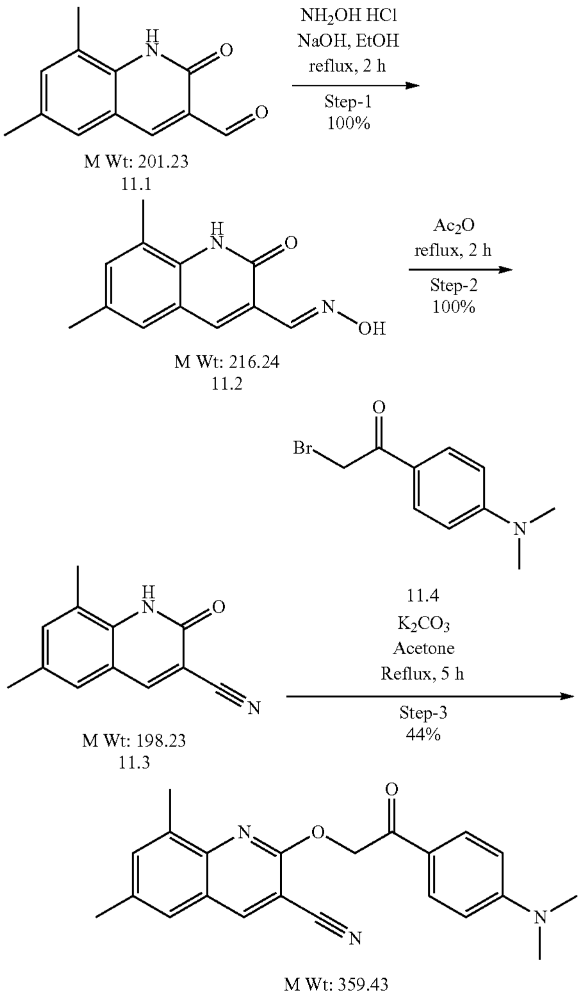

(E)-6,8-dimethyl-2-oxo-1,2-dihydroquinoline-3-carbaldehyde oxime. Step-1: To a solution of hydroxylamine hydrochloride (50 mg, 0.72 mmol) in water (0.15 mL) was added 4M aqueous sodium hydroxide solution (0.2 mL) at 10° C. and stirred for 10 min at room temperature and added to a solution of compound-11.1 (50 mg, 0.25 mmol) in ethanol (1.16 mL) at room temperature and the resulting reaction mixture was heated to 90° C. and stirred for 3 h. After completion of the reaction (confirmed by TLC; 5% MeOH:DCM; $R_f$~0.2), the reaction mixture was cooled to room temperature and poured in cold water. The pH of the solution was adjusted to 2 using 4N aqueous hydrochloric acid solution. The solid separated w s filtered and washed with water and dried under reduced pressure to yield compound-11.2 (54 mg, 100%).

6,8-dimethyl-2-oxo-1,2-dihydroquinoline-3-carbonitrile. Step-2: Acetic anhydride (1.8 g, 18 mmol) was added to compound-11.2 (54 mg, 0.25 mmol) and heated to 140° C. and stirred for 3 h. After completion of the reaction (confirmed by TLC; 5% MeOH:DCM), the reaction mixture was cooled to room temperature and diluted with water. The mixture was then basified to pH=10 using 4 N aqueous sodium hydroxide solution. The solid separated was filtered, washed with water, and dried under reduced pressure to yield compound-11.3 (50 mg quantitative yield).

2-(2-(4-(dimethylamino)phenyl)-2-oxoethoxy)-6,8-dimethylquinoline-3-carbonitrile. Step-3: A flame dried vial was charged with compound-11.3 (50 mg, 0.25 mmol) in anhydrous dimethylformamide (1 mL), was added potassium carbonate (38 mg, 0.27 mmol) and potassium iodide (42 mg, 0.27 mmol). This reaction mixture was stirred at room temperature for 15 min followed by the addition of compound-11.4 (60 mg, 0.25 mmol) was added to the above reaction mixture and stirred at 150° C. for 30 min and at room temperature for overnight. TLC and LCMS showed complete conversion to product formation. The reaction mixture was poured into water (5 mL), extracted with ethyl acetate (3×10 mL) and combined organic layers were dried over anhydrous sodium sulfate, filtered and evaporated. The resultant crude compound was purified by using 12 g silica flash column, eluted with Hexane in ethyl acetate (0 to 30%), the desired fractions were concentrated, triturated with diethyl ether. Finally, the co pound was purified by Prep HPLC, gave desired product as a solid (40 mg, 44%). (+esi)[M+H]=360.2. $^1$H NMR (300 MHz, CD2Cl2) δ 8.28 (s, 1H), 7.87-7.83 (m, 2H), 7.33-7.31 (m, 2H), 6.75-6.72 (m, 2H), 5.63 (s, 2H), 2.99 (s, 6H), 2.34 (s, 3H), 2.28 (s, 3H).

Increase of Sarcospan Protein Levels In Vitro

Compounds of the invention were assayed for increase of SSPN protein levels over vehicle (fold change over vehicle) with the SSPN-HiBiT assay described above (*p<0.05).

TABLE 1

| Structure | MW | SSPN-HiBiT, fold change over vehicle |
|---|---|---|
| 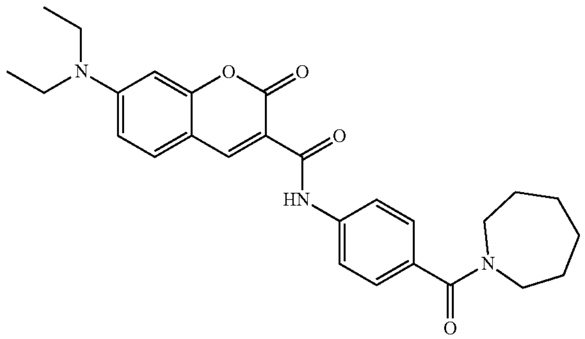 [SMILES: CCN(CC)c1ccc2cc(C(=O)Nc3ccc(C(=O)N4CCCCCC4)cc3)c(=O)oc2c1] | 461.6 | 2.29* |
| 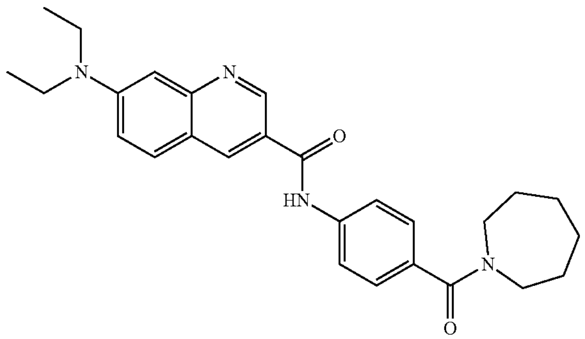 [SMILES: CCN(CC)c1ccc2cc(C(=O)Nc3ccc(C(=O)N4CCCCCC4)cc3)cnc2c1] | 444.6 | 1.62* |

TABLE 1-continued
| Structure | MW | SSPN-HiBiT, fold change over vehicle |
|---|---|---|
| 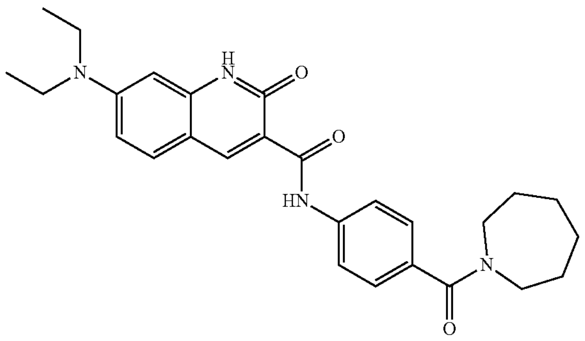 | 460.6 | 1.49* |
| 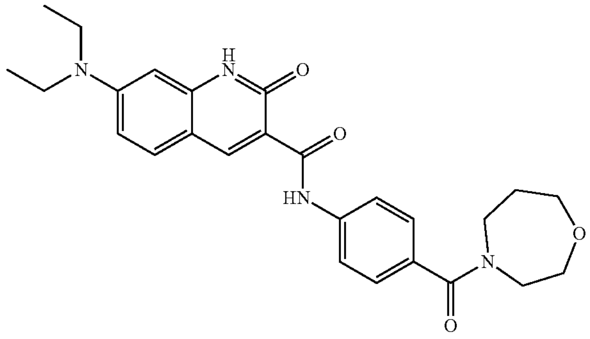 | 462.5 | 1.81* |
| 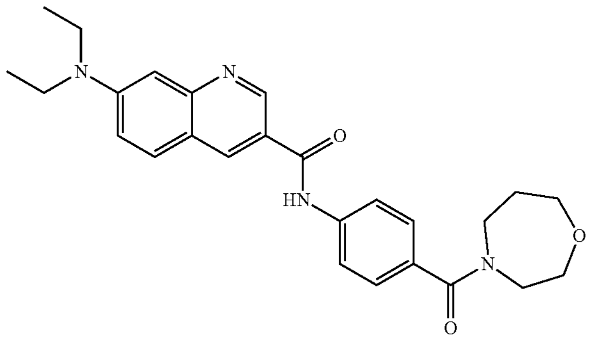 [SMILES: CCN(CC)c1ccc2cc(C(=O)Nc3ccc(C(=O)N4CCCOCC4)cc3)cnc2c1] | 446.5 | 1.3* |
| 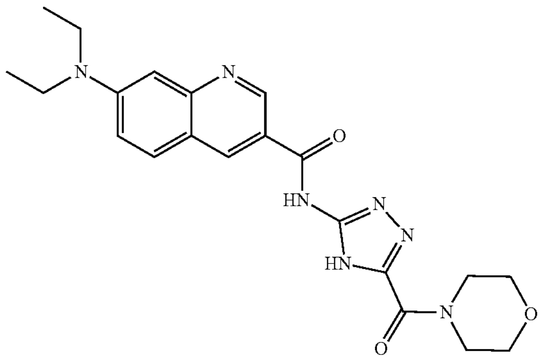 [SMILES: CCN(CC)c1ccc2cc(C(=O)Nc3nnc(C(=O)N4CCOCC4)[nH]3)cnc2c1] | 423.5 | 1.34* |

TABLE 1-continued
| Structure | MW | SSPN-HiBiT, fold change over vehicle |
|---|---|---|
| 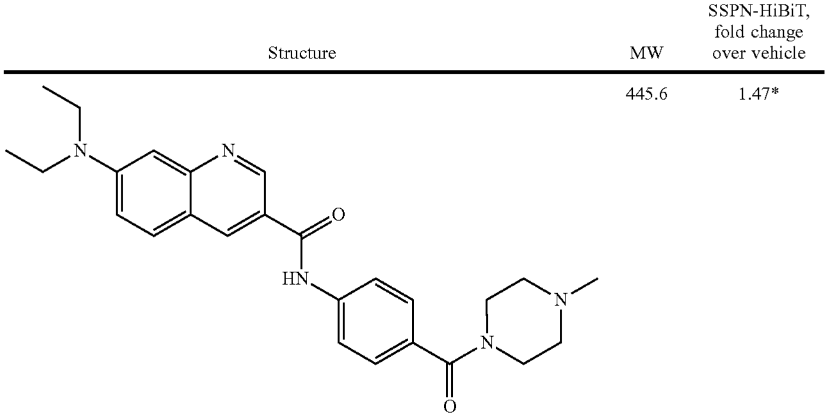 | 445.6 | 1.47* |
| 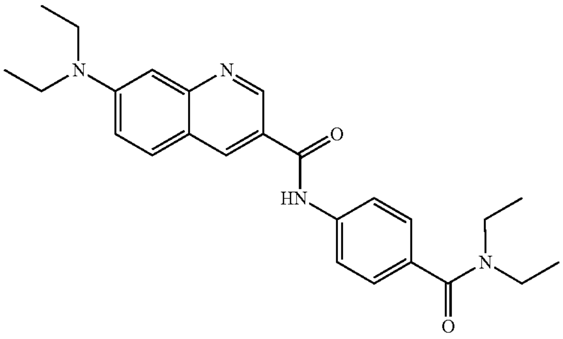 [SMILES: CCN(CC)C(=O)c1ccc(NC(=O)c2cnc3cc(N(CC)CC)ccc3c2)cc1] | 418.5 | 1.75* |
| 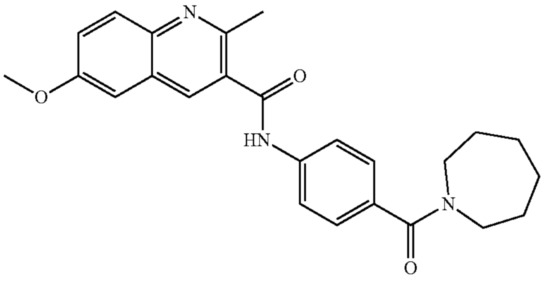 [SMILES: COc1ccc2nc(C)c(C(=O)Nc3ccc(C(=O)N4CCCCCC4)cc3)cc2c1] | 417.21 | 1.4* |
| 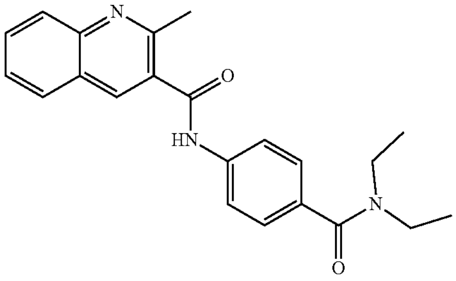 [SMILES: CCN(CC)C(=O)c1ccc(NC(=O)c2cc3ccccc3nc2C)cc1] | 361.18 | 1.08* |
| 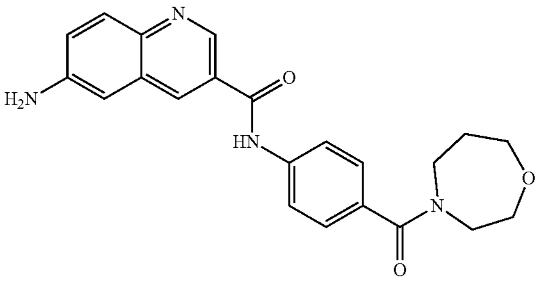 [SMILES: Nc1ccc2ncc(C(=O)Nc3ccc(C(=O)N4CCCOCC4)cc3)cc2c1] | 390.17 | 1.09* |

TABLE 1-continued
| Structure | MW | SSPN-HiBiT, fold change over vehicle |
|---|---|---|
| 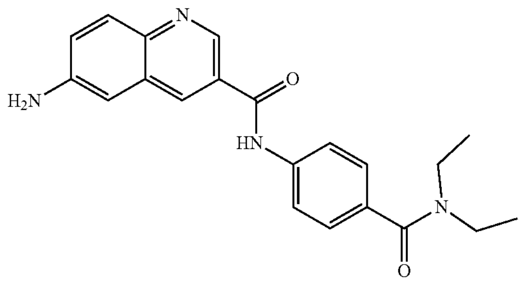 [SMILES: CCN(CC)C(=O)c1ccc(NC(=O)c2cnc3ccc(N)cc3c2)cc1] | 362.17 | 1.17* |
| 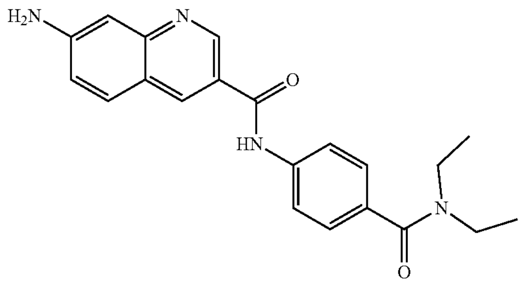 [SMILES: CCN(CC)C(=O)c1ccc(NC(=O)c2cnc3cc(N)ccc3c2)cc1] | 362.17 | 1.36* |
| 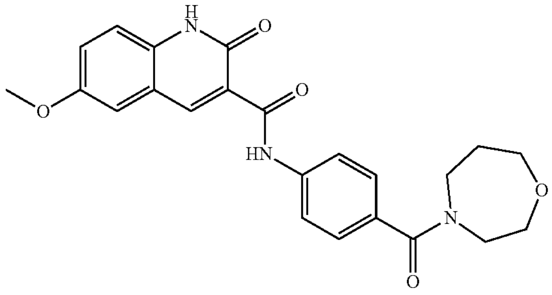 [SMILES: COc1ccc2[nH]c(=O)c(C(=O)Nc3ccc(C(=O)N4CCCOCC4)cc3)cc2c1] | 421.16 | 2.4* |
| 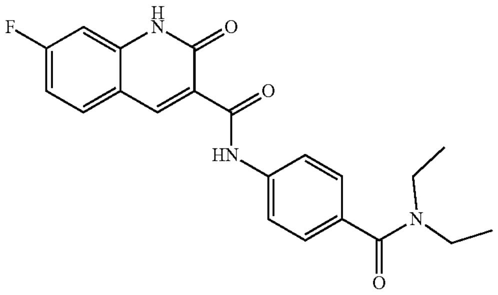 [SMILES: CCN(CC)C(=O)c1ccc(NC(=O)c2cc3ccc(F)cc3[nH]c2=O)cc1] | 381.15 | 1.45* |
| 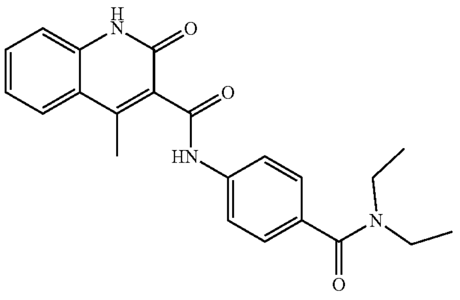 [SMILES: CCN(CC)C(=O)c1ccc(NC(=O)c2c(C)c3ccccc3[nH]c2=O)cc1] | 377.17 | 1.21* |

TABLE 1-continued
| Structure | MW | SSPN-HiBiT, fold change over vehicle |
|---|---|---|
| 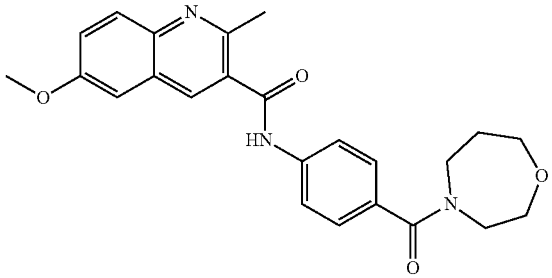 [SMILES: COc1ccc2nc(C)c(C(=O)Nc3ccc(C(=O)N4CCCOCC4)cc3)cc2c1] | 419.18 | 1.22* |
| 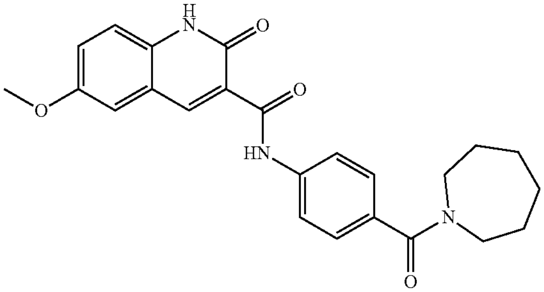 [SMILES: COc1ccc2[nH]c(=O)c(C(=O)Nc3ccc(C(=O)N4CCCCCC4)cc3)cc2c1] | 419.18 | 1.03 |
| 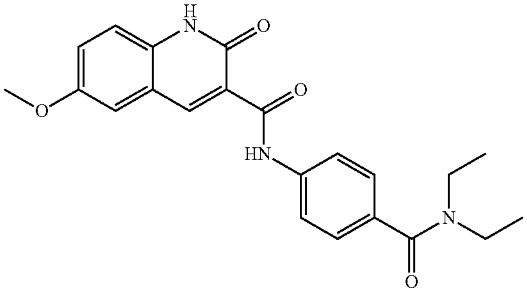 [SMILES: CCN(CC)C(=O)c1ccc(NC(=O)c2cc3cc(OC)ccc3[nH]c2=O)cc1] | 393.17 | 1.51* |
| 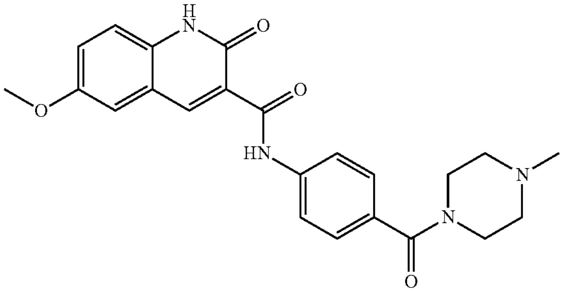 | 420.18 | 1.46* |
TABLE 2
| Structure | MW | SSPN-HiBiT, fold change over vehicle |
|---|---|---|
| 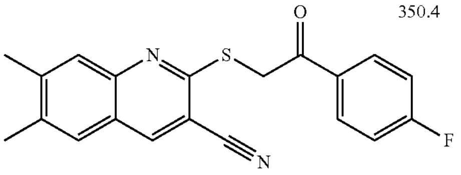 [SMILES: Cc1cc2cc(C#N)c(SCC(=O)c3ccc(F)cc3)nc2cc1C] | 350.4 | 1.48* |
TABLE 2-continued
| Structure | MW | SSPN-HiBiT, fold change over vehicle |
|---|---|---|
| 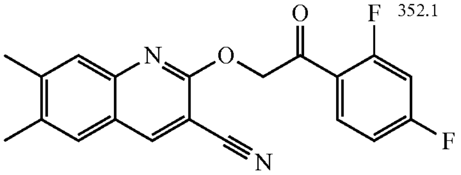 [SMILES: Cc1cc2cc(C#N)c(OCC(=O)c3ccc(F)cc3F)nc2cc1C] | 352.1 | 1.22* |

TABLE 2-continued

| Structure | MW | SSPN-HiBiT, fold change over vehicle |
|---|---|---|
| 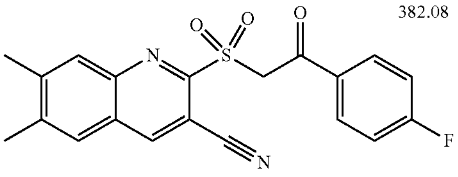 [SMILES: Cc1cc2cc(C#N)c(S(=O)(=O)CC(=O)c3ccc(F)cc3)nc2cc1C] | 382.08 | 1.23* |
| 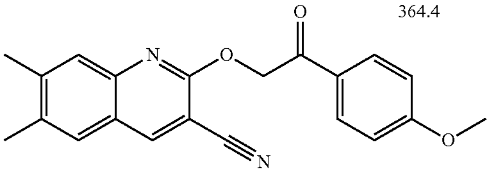 | 364.4 | 1.27* |
| 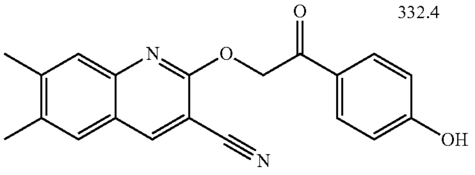 [SMILES: Cc1cc2cc(C#N)c(OCC(=O)c3ccc(O)cc3)nc2cc1C] | 332.4 | 1.21 |
| 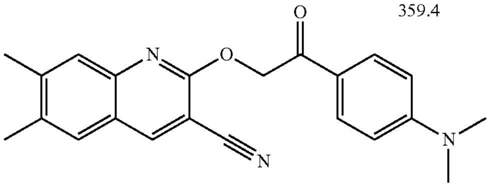 | 359.4 | 1.04* |
| 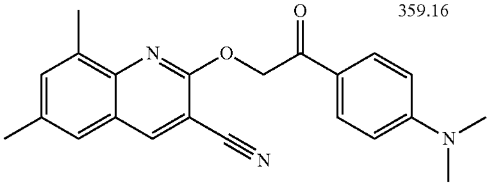 | 359.16 | 1.3* |
| 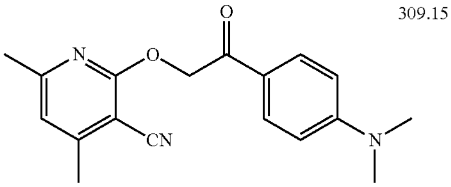 | 309.15 | 1.09* |

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A compound represented by formula (IIb) or a pharmaceutically acceptable salt thereof:

(IIb)

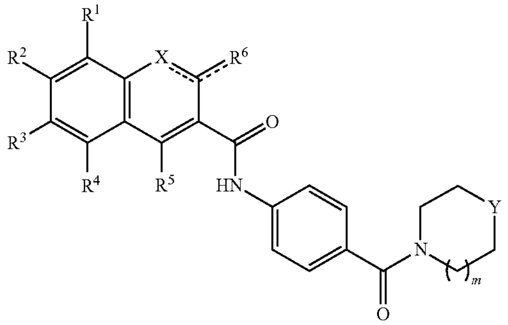

wherein

X is O, N or $NR^9$;

$R^1$, $R^2$, $R^3$, and $R^4$ are each independently H, alkyl, alkoxy, halo, nitrile, amino or aminoalkyl;

$R^5$ is H, alkoxy, halo, nitrile, amino or aminoalkyl;

$R^6$ is H, =O or alkyl;

$R^9$ is H or alkyl; and

Y is O or $NR^{10}$, $R^{10}$ is H, alkyl or acyl; and m is 1 or 2.

2. A compound selected from:

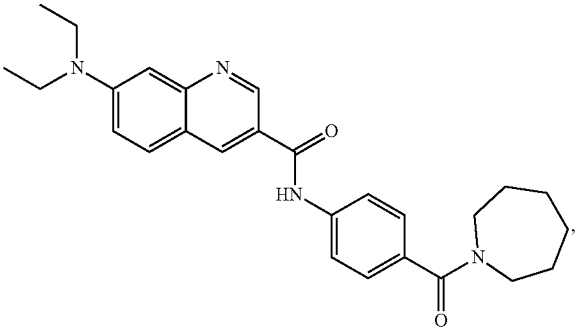,

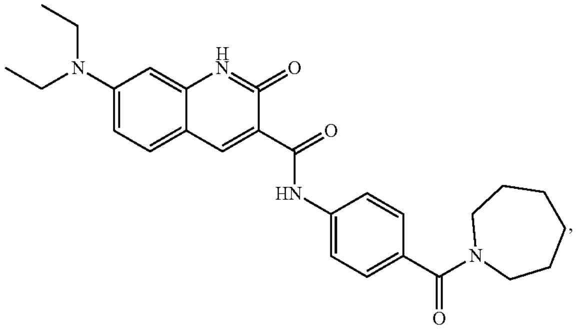,

-continued
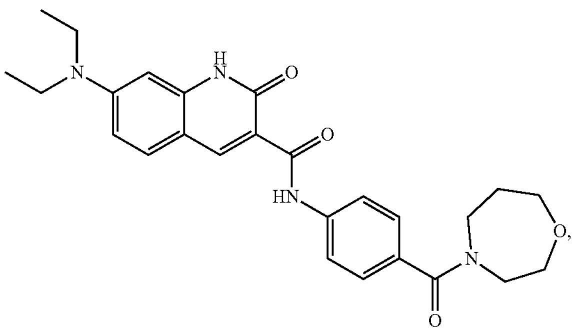
,
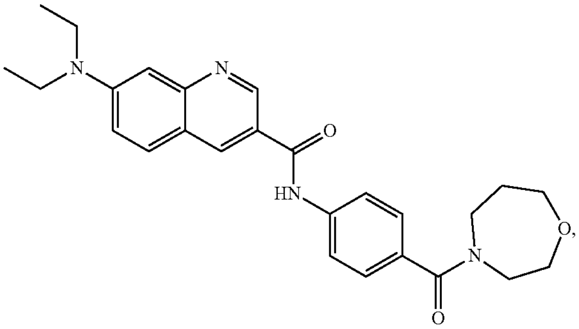
,
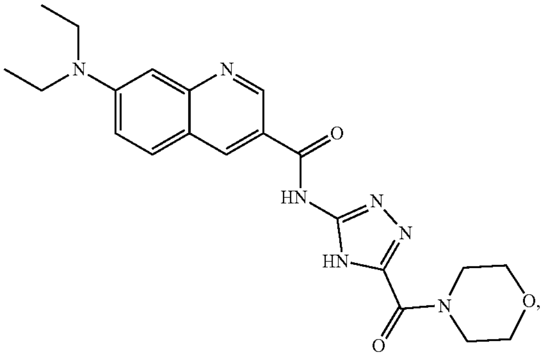
,
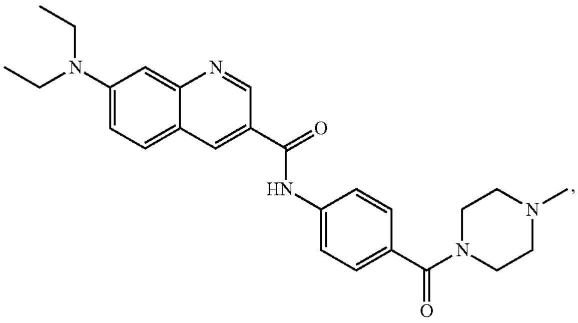
,
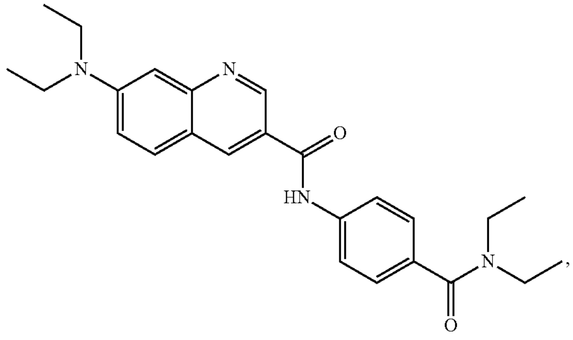
,
-continued
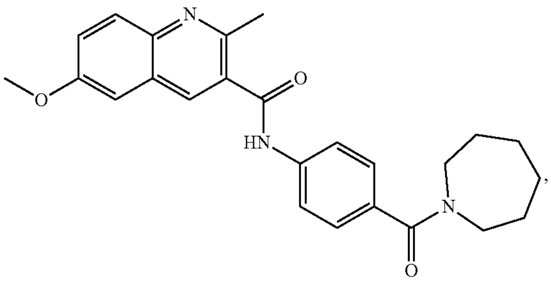
,
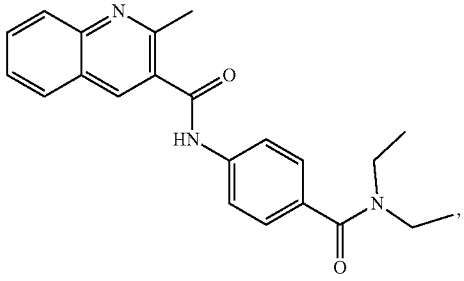
,
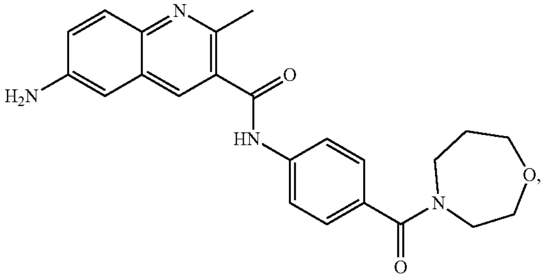
,
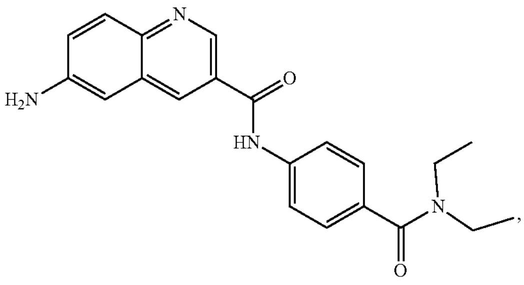
,
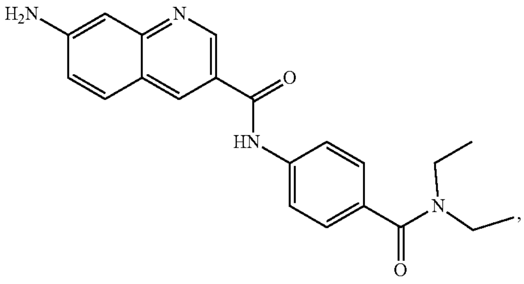
,
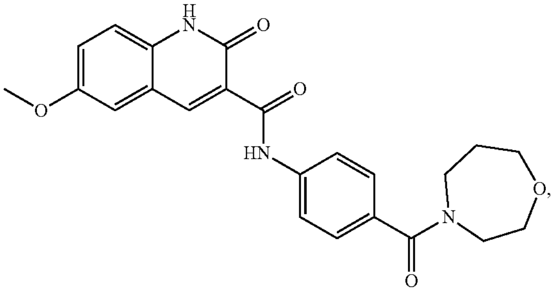
, -continued

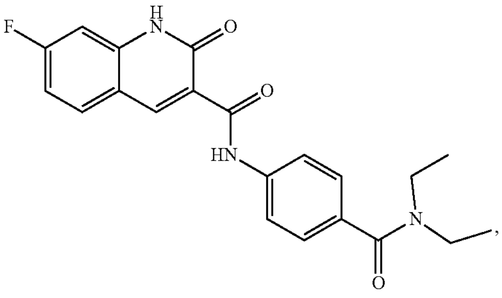

,

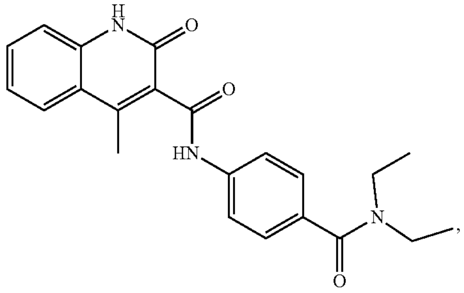

,

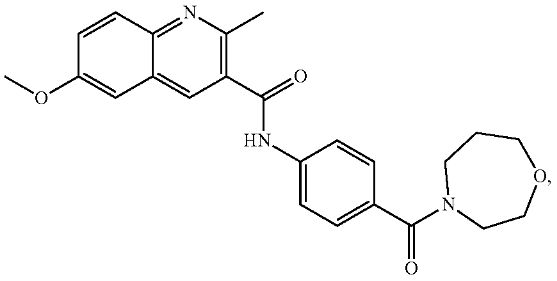

,

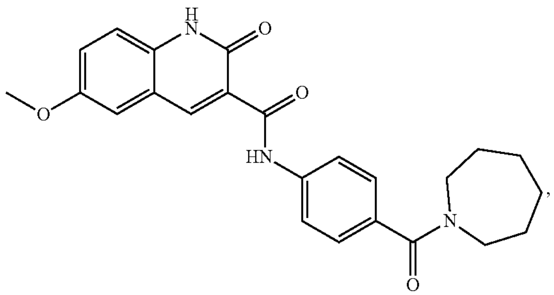

,

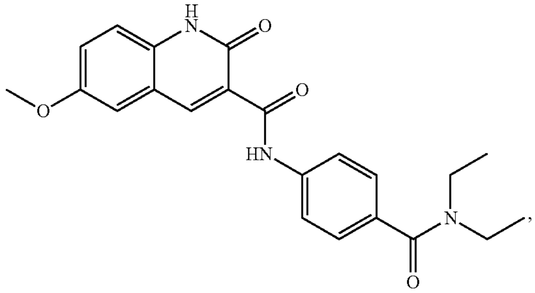

, and

-continued

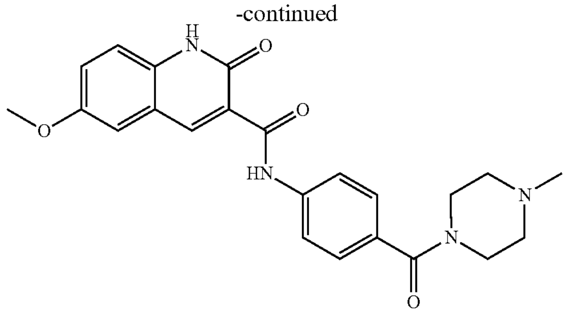

or a pharmaceutically acceptable salt thereof.

3. A pharmaceutical composition comprising a compound of claim 1, and a pharmaceutically acceptable excipient.

4. A method of treating a muscular dystrophy in a subject in need thereof, comprising administering to the subject a compound of formula (II) or a pharmaceutically acceptable salt thereof:

(II)

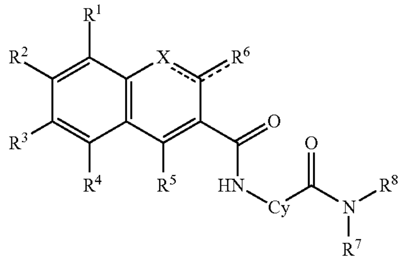

wherein

X is O, N or $NR^9$;

$R^1$, $R^2$, $R^3$, $R^4$ and $R^5$ are each independently H, alkyl, alkoxy, halo, nitrile, amino or aminoalkyl;

$R^6$ is H, =O or alkyl;

Cy is aryl or heteroaryl;

$R^7$ and $R^8$ are each independently H or alkyl, or taken together with the N atom to which they are attached form a heterocyclyl; and $R^9$ is H or alkyl.

5. The method of claim 4, wherein Cy is aryl.

6. The method of claim 5, wherein the compound is represented by formula (IIa):

(IIa)

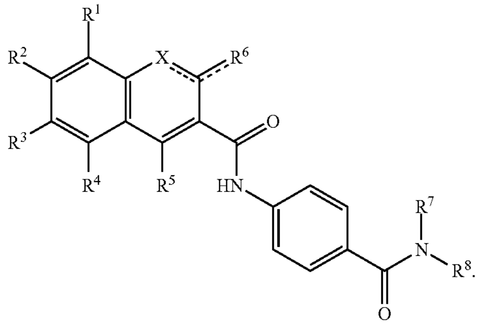

7. The method of claim 6, wherein X is N.

8. The method of claim 6, wherein the compound is represented by formula (IIb):
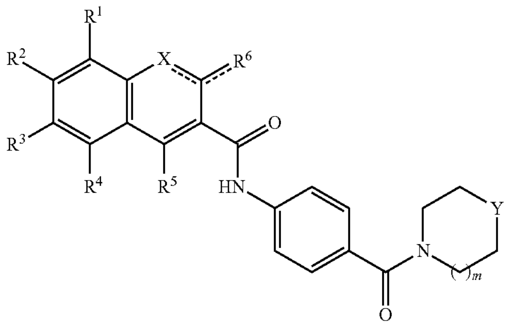
(IIb)
wherein
Y is O or $NR^{10}$,
$R^{10}$ is H, alkyl or acyl; and
m is 1 or 2.
9. The method of claim 4, wherein the compound is selected from:
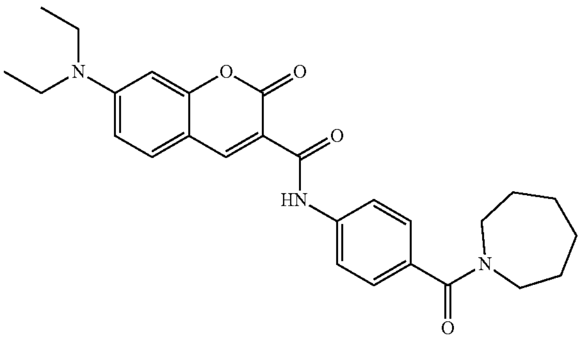
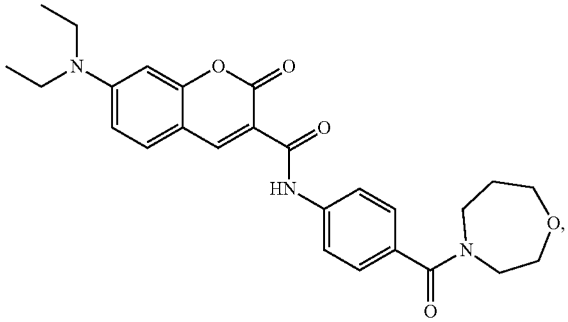
,
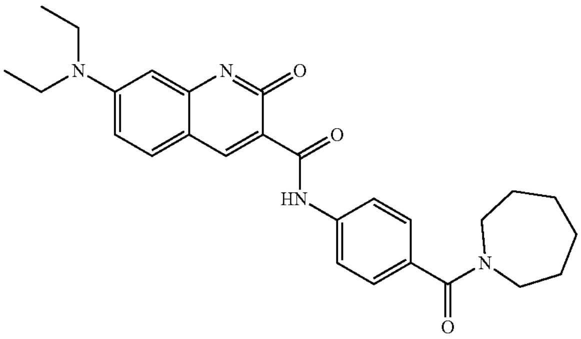
-continued
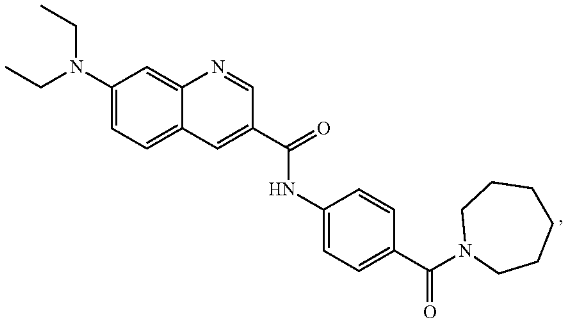
,
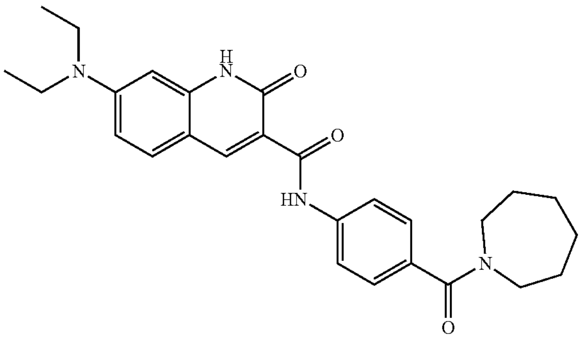
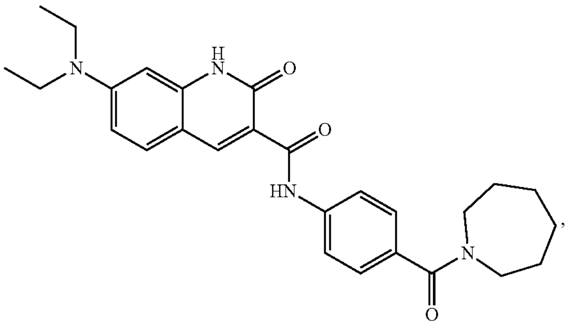
,
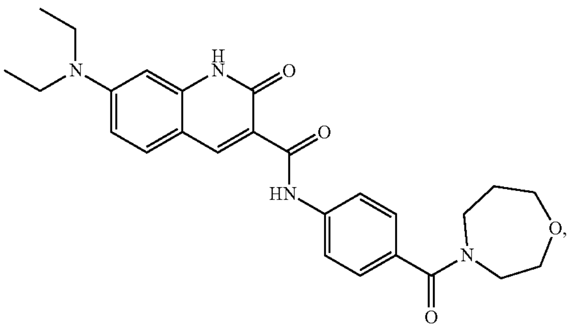
,
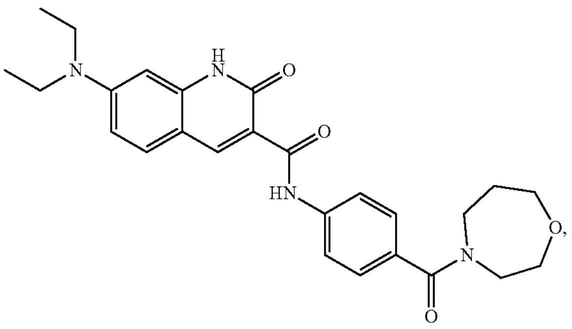
, -continued
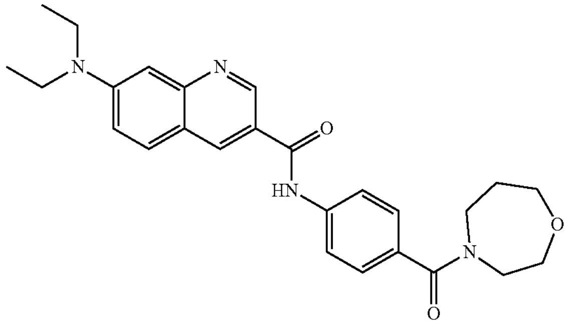
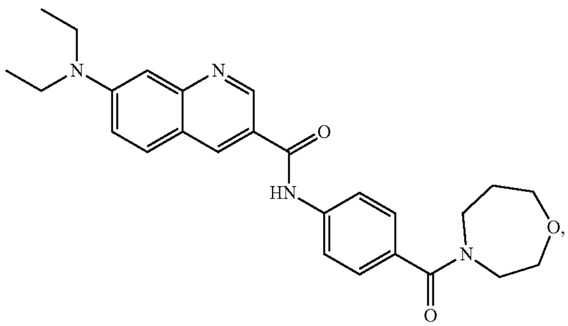
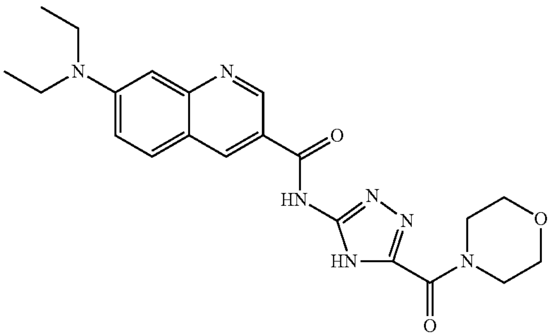
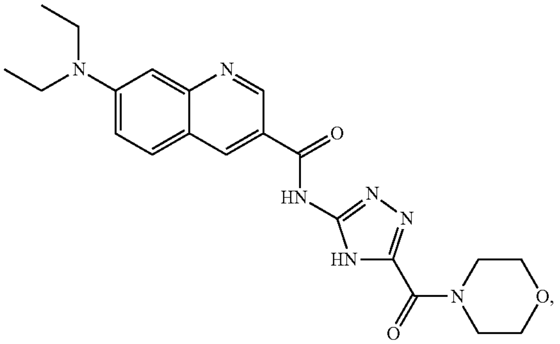
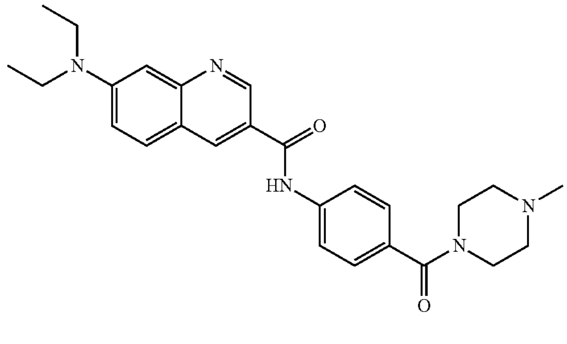
-continued
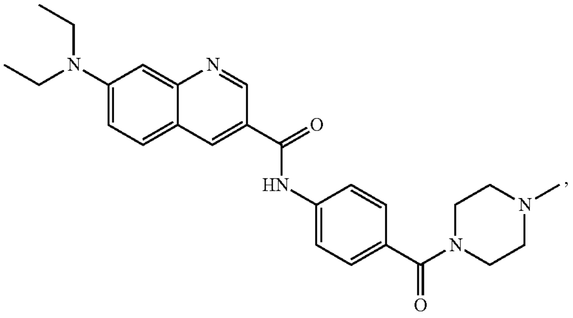
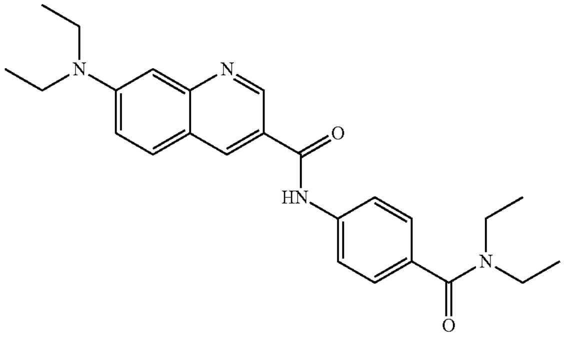
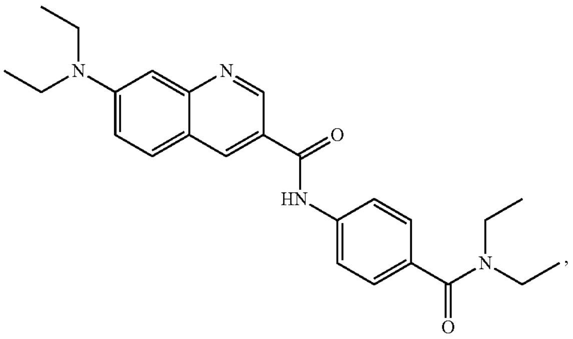
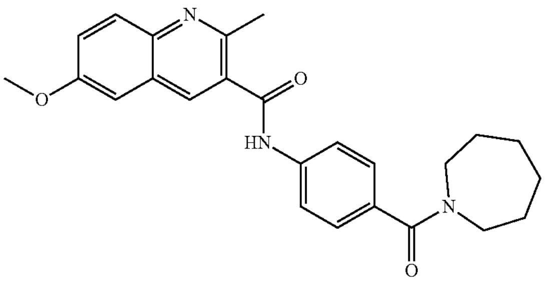
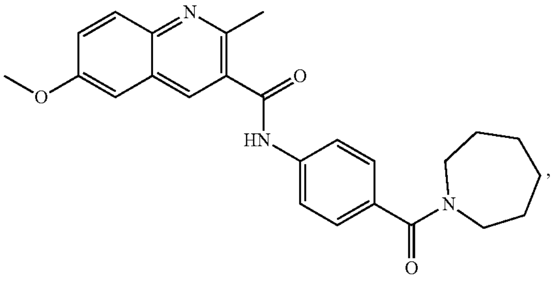

-continued
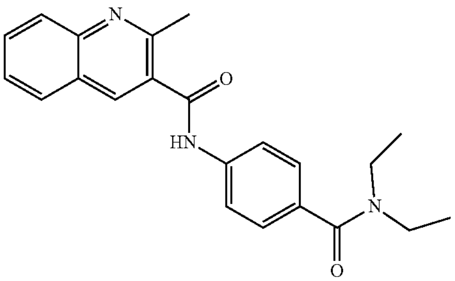
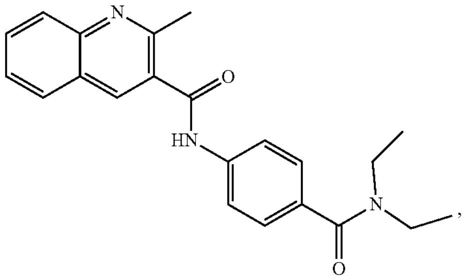
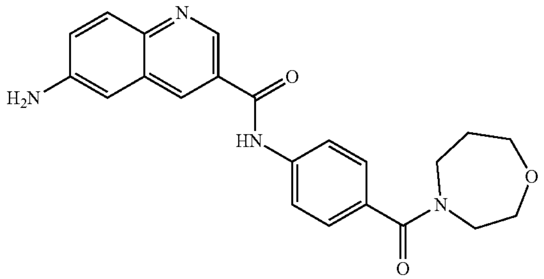
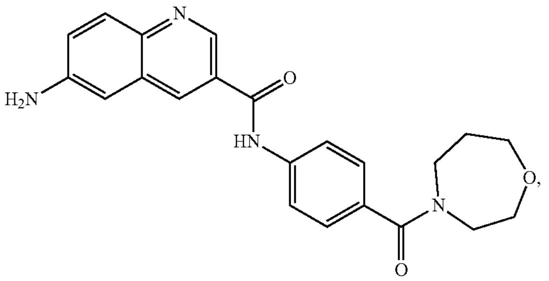
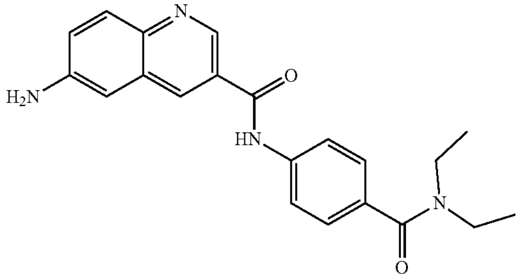
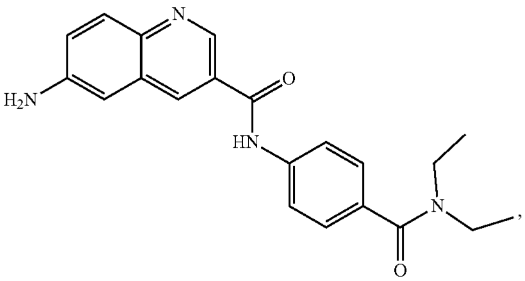
-continued
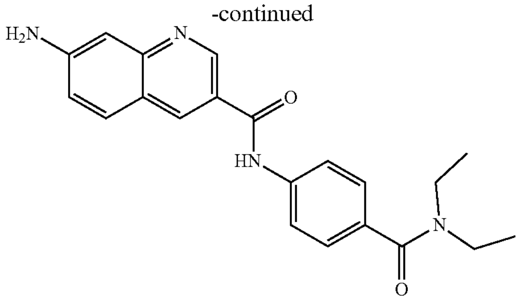
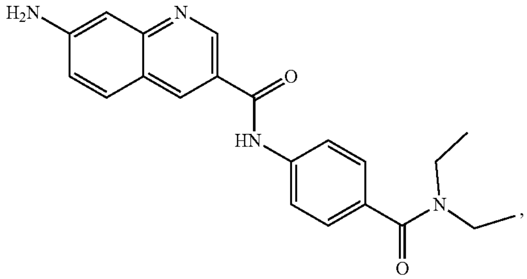
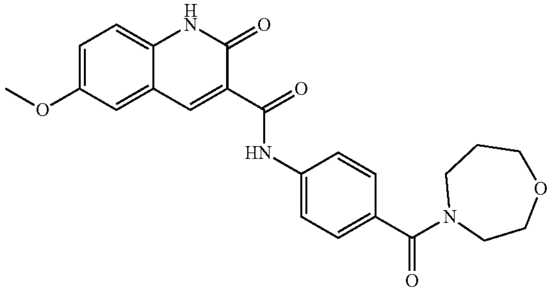
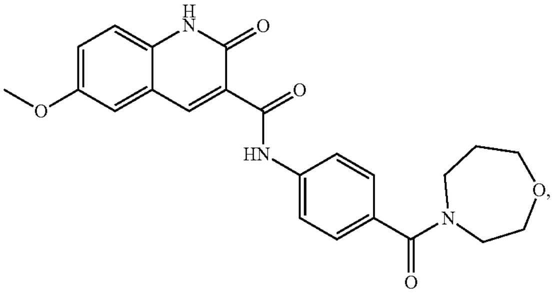
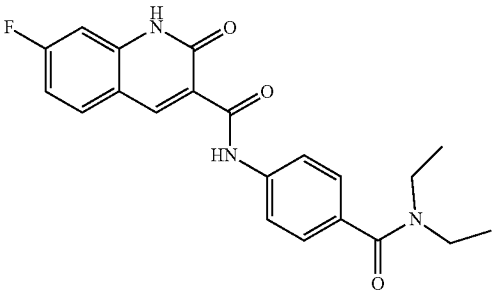
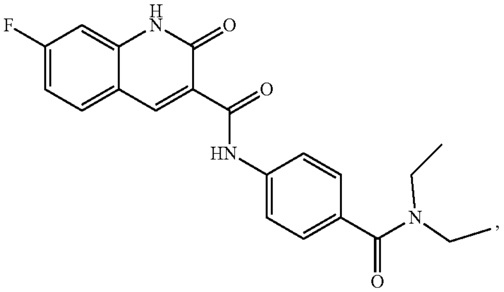

-continued
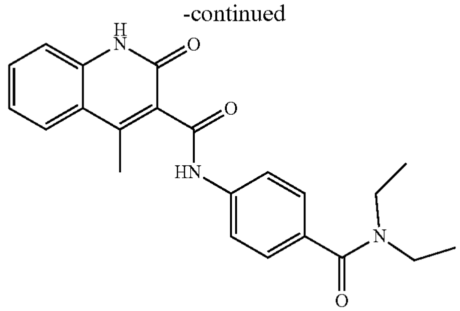
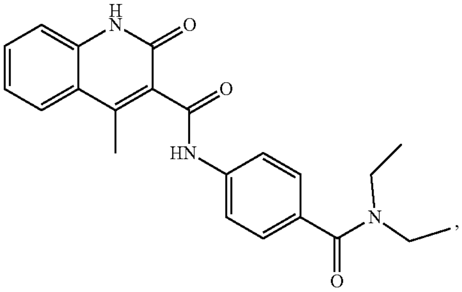
,
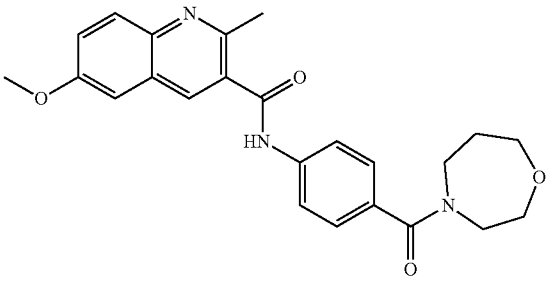
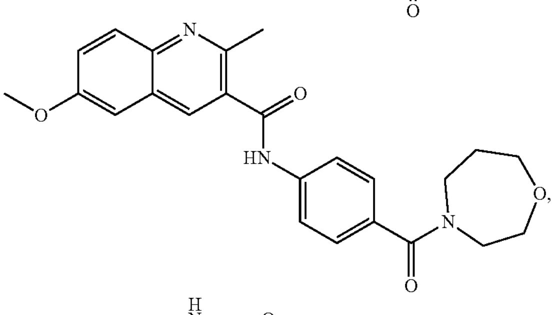
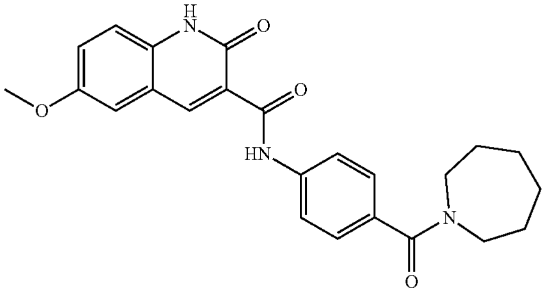
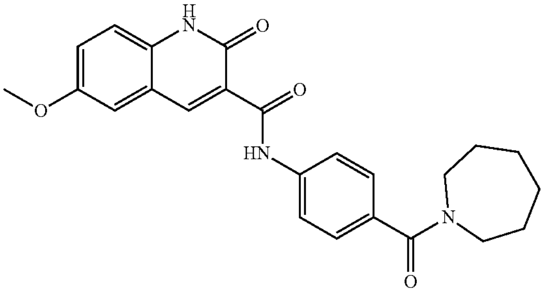
,
-continued
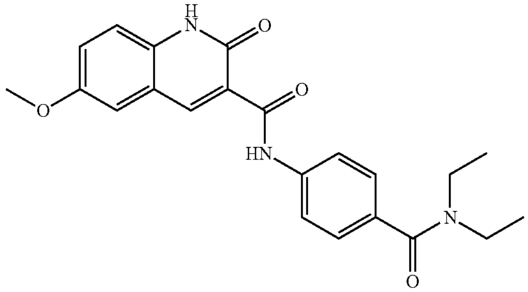
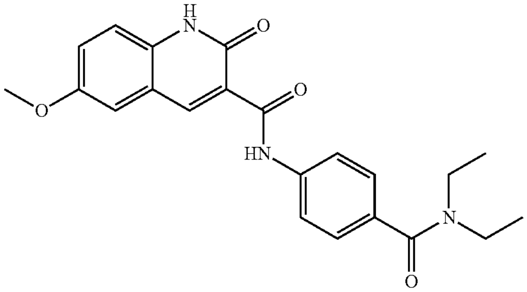
, and
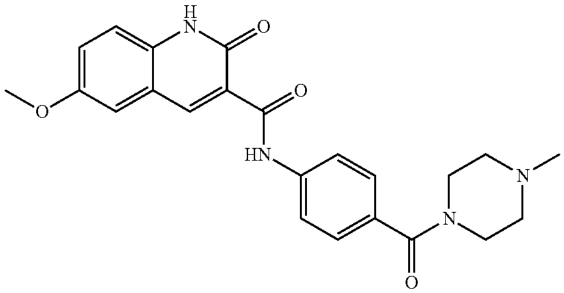
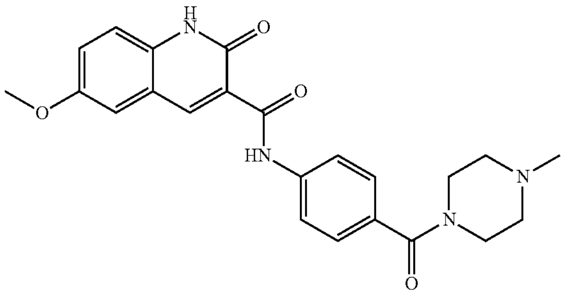
or a pharmaceutically acceptable salt thereof.
10. The method of claim 4, wherein the muscular dystrophy is Duchenne muscular dystrophy (DMD).
* * * * *